(12) United States Patent
Patel

(10) Patent No.: US 10,947,226 B2
(45) Date of Patent: Mar. 16, 2021

(54) BICYCLIC PYRIDONE LACTAMS AND METHODS OF USE THEREOF

(71) Applicant: Genentech, Inc., South San Francisco, CA (US)

(72) Inventor: Snahel Patel, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/385,353

(22) Filed: Apr. 16, 2019

(65) Prior Publication Data

US 2019/0241565 A1    Aug. 8, 2019

Related U.S. Application Data

(63) Continuation of application No. PCT/EP2017/076385, filed on Oct. 16, 2017.

(60) Provisional application No. 62/409,214, filed on Oct. 17, 2016.

(51) Int. Cl.
C07D 471/04 (2006.01)
C07D 519/00 (2006.01)
A61K 31/55 (2006.01)
A61P 13/12 (2006.01)

(52) U.S. Cl.
CPC ............ C07D 471/04 (2013.01); A61K 31/55 (2013.01); A61P 13/12 (2018.01); C07D 519/00 (2013.01)

(58) Field of Classification Search
CPC .... C07D 471/04; C07D 519/00; A61K 31/55; A61P 13/12
USPC ...................................... 540/524; 514/212.08
See application file for complete search history.

(56) References Cited

U.S. PATENT DOCUMENTS

| | | | |
|---|---|---|---|
| 5,206,234 | A | 4/1993 | Bock et al. |
| 6,350,741 | B1 | 2/2002 | Golec et al. |
| 7,057,046 | B2 | 6/2006 | Sher et al. |
| 7,425,550 | B2 | 9/2008 | Sher et al. |
| 9,815,850 | B2 | 11/2017 | Estrada et al. |
| 2004/0002495 | A1 | 1/2004 | Sher et al. |
| 2011/0038877 | A1 | 2/2011 | Way et al. |
| 2017/0008877 | A1 | 1/2017 | Patel et al. |
| 2018/0170927 | A1 | 6/2018 | Patel et al. |

FOREIGN PATENT DOCUMENTS

| | | |
|---|---|---|
| EP | 3318267 A1 | 5/2018 |
| WO | 02/20530 A1 | 3/2002 |
| WO | 03/046222 A1 | 6/2003 |
| WO | 2004/037986 A2 | 5/2004 |
| WO | 2006/031606 A2 | 3/2006 |
| WO | 2008/011190 A1 | 1/2008 |
| WO | 2009/140128 A2 | 11/2009 |
| WO | 2013/059791 A2 | 4/2013 |
| WO | 2014/009495 A1 | 1/2014 |
| WO | 2014/023708 A1 | 2/2014 |
| WO | 2014/125444 A1 | 8/2014 |
| WO | 2014/145022 A1 | 9/2014 |
| WO | 2014/170892 A1 | 10/2014 |
| WO | 2016/027253 A1 | 2/2016 |
| WO | 2017/001645 A1 | 1/2017 |
| WO | 2017/001655 A1 | 1/2017 |
| WO | 2017/001660 A1 | 1/2017 |
| WO | 2017/004500 A1 | 1/2017 |
| WO | 2017/096301 A1 | 6/2017 |
| WO | 2017/103851 A1 | 6/2017 |
| WO | 2017/109724 A1 | 6/2017 |
| WO | 2017/112815 A1 | 6/2017 |
| WO | 2017/136727 A2 | 8/2017 |
| WO | 2018/109097 A1 | 6/2018 |
| WO | 2019/204537 A1 | 10/2019 |

OTHER PUBLICATIONS

Cecil Textbook of Medicine, edited by Bennet, J.C., and Plum F., 20th edition,vol. 1, 1004-1010, 1996.*
Freshney et al.,Culture of Animal Cells, a Manual of Basic Technique, Alan R. Liss, Inc., 1983, New York, p. 4.*
Dermeret al., Bio/Technology, 1994, 12:320.*
Bertrand et al., "cIAP1 and cIAP2 facilitate cancer cell survival by functioning as E3 ligases that promote RIP1 ubiquitination," Mol. Cell 30(6):689-700 (2008).
Chen, "Ubiquitination in signaling to and activation of IKK," Immunol. Rev. 246(1):95-106 (2012).
Cho et al., "Phosphorylation-driven assembly of the RIP1-RIP3 complex regulates programmed necrosis and virus-induced inflammation," Cell 137(6):1112-1123 (2009).
De Almagro et al., "Necroptosis: Pathway deversity and characteristics," Semin. Cell Dev. Biol. 39:56-62 (2015).
Degterev et al., "Chemical inhibitor of nonapoptotic cell death with therapeutic potential for ischemic brain injury," Nat. Chem. Biol. 1(2):112-119 (2005).
Degterev et al., "Identification of RIP1 kinase as a specific cellular target of necrostatins," Nat. Chem. Biol. 4(5):313-321 (2008).

(Continued)

Primary Examiner — Venkataraman Balasubramanian
(74) Attorney, Agent, or Firm — Andre T. Krammer

(57) ABSTRACT

The invention provides novel compounds having the general formula I:

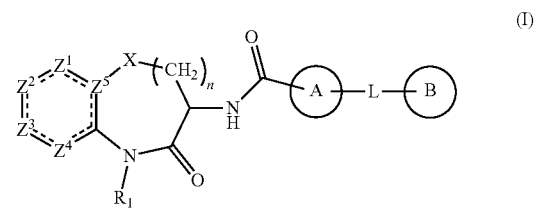

wherein $R^1$, X, $Z^1$ to $Z^5$, L, n, the A ring, and the B ring, are as described herein, pharmaceutical compositions including the compounds and methods of using the compounds.

23 Claims, No Drawings

(56) References Cited

OTHER PUBLICATIONS

Feoktistova et al., "cIAPs block Ripoptosome formation, a RIP1/caspase-8 containing intracellular cell death complex differentially regulated by cFLIP isoforms," Mol. Cell 143(3):449-463 (2011).
Hamilton et. al., "Potent and selective inhibitors of receptor-interacting protein kinase 1 that lack an aromatic back pocket group," Bioorg. Med. Chem. Lett. 29(12):1497-1501 (2019).
Harris et al., "Discovery of Small Molecule RIP1 Kinase Inhibitors for the Treatment of Pathologies Associated with Necroptosis," ACS Med. Chem. Lett. 4(12):1238-1243 (2013).
Harris et al., "Discovery of a First-in-Class Receptor Interacting Protein 1 (RIP1) Kinase Specific Clinical Candidate (GSK2982772) for the Treatment of Inflammatory Diseases," J. Med. Chem. 60(4):1247-1261 (2017).
He et al., "Receptor interacting protein kinase-3 determines cellular necrotic response to TNF-alpha," Cell 137(6):1100-1111 (2009).
Kaiser et al., "Toll-like receptor 3-mediated necrosis via TRIF, RIP3, and MLKL," J. Biol. Chem. 288(43):31268-31279 (2013).
Linkermann et al., "Necroptosis," N. Engl. J. Med. 370(5):455-465 (2014).
Najjar et al., "Structure Guided Design of Potent and Selective Ponatinib-Based Hybrid Inhibitors for RIPK1" Cell Rep. 10(11):1850-60 (2015).
Newton et al., "Activity of protein kinase RIPK3 determines whether cells die by necroptosis or apoptosis," Science 343(6177):1357-1360 (2014).
Newton, "RIPK1 and RIPK3: critical regulators of inflammation and cell death," Trends Cell Biol. 25(6):347-353 (2015).
O'Donnell et al., "Ubiquitination of RIP1 regulates an NF-kappaB-independent cell-death switch in TNF signaling," Curr. Biol. 17(5):418-424 (2007).

Sun et al., "Mixed lineage kinase domain-like protein mediates necrosis signaling downstream of RIP3 kinase," Cell 148(1-2):213-227 (2012).
Takahashi et al., "Necrostatin-1 analogues: critical issues on the specificity, activity and in vivo use in experimental disease models," Cell Death Dis. 3(11):e437 (2012).
Vanden Berghe et al., "Regulated necrosis: the expanding network of non-apoptotic cell death pathways," Nat. Rev. Mol. Cell Biol. 15(2):135-147 (2014).
Wang et al., "TNF—α induces two distinct caspase-8 activation pathways," Cell 133(4):693-703 (2008).
Zhao et al., "Mixed lineage kinase domain-like is a key receptor interacting protein 3 downstream component of TNF-induced necrosis," Proc. Natl. Acad. Sci. USA 109(14):5322-5327 (2012).
Wikipedia, Spiro compound, https://en.wikipedia.org/wiki/Spiro_compound, Jul. 30, 2018, 8 pages.
PCT International Search Report and Written Opinion for PCT/US2016/040659, dated Sep. 20, 2016, 10 pages.
PCT International Search Report and Written Opinion for PCT/EP2017/076385, dated Dec. 7, 2017, 12 pages.
PCT International Search Report and Written Opinion for PCT/EP2017/082851, dated Feb. 20, 2018, 16 pages.
PCT International Search Report and Written Opinion for PCT/US2019/028011, dated Jul. 9, 2019, 13 pages.
USPTO Non-Final Office Action, U.S. Appl. No. 15/839,788, dated Jan. 22, 2019, 8 pages.
USPTO Notice of Allowance, U.S. Appl. No. 15/839,788, dated Dec. 4, 2019, 5 pages.
USPTO Non-Final Office Action, U.S. Appl. No. 15/200,058, dated Jan. 28, 2020, 6 pages.
USPTO Final Office Action, U.S. Appl. No. 15/200,058, dated Aug. 3, 2018, 12 pages.

* cited by examiner

BICYCLIC PYRIDONE LACTAMS AND METHODS OF USE THEREOF

CROSS-REFERENCE TO RELATED APPLICATION

This application is a Continuation of International Application No. PCT/EP2017/076385 filed on Oct. 16, 2017, which claims priority to U.S. Provisional Patent Application No. 62/409,214 filed Oct. 17, 2016, the disclosures of which is incorporated herein by reference in their entirety.

FIELD OF THE INVENTION

The invention relates to organic compounds useful for therapy and/or prophylaxis in a mammal, and in particular to inhibitors of RIP1 kinase useful for treating diseases and disorders associated with inflammation, cell death and others.

BACKGROUND OF THE INVENTION

Receptor-interacting protein-1 ("RIP1") kinase is a serine/threonine protein kinase. RIP1 is a regulator of cell signaling that is involved, among other things, in the mediation of programmed cell death pathways, e.g., necroptosis. The best studied form of necroptotic cell death is initiated by TNFα (tumor necrosis factor), but necroptosis can also be induced by other members of the TNFα death ligand family (Fas and TRAIL/Apo2L), interferons, Toll-like receptors (TLRs) signaling and viral infection via the DNA sensor DAI (DNA-dependent activator of interferon regulatory factor) [1-3]. Binding of TNFα to the TNFR1 (TNF receptor 1) prompts TNFR1 trimerization and formation of an intracellular complex, Complex-I. TRADD (TNF receptor associated death domain protein) binds to the intracellular death domain of TNFR1 and recruits the protein kinase RIP1 (receptor-interacting protein 1) through the death domain present in both proteins [4]. Following initial recruitment into TNFR1-associated signaling complex, RIP1 translocates to a secondary cytoplasmatic complex, Complex-II [5-7]. Complex-II is formed by the death domain containing protein FADD (Fas-associated Protein), RIP1, caspase-8 and cFLIP. If caspase-8 is not fully activated or its activity is blocked, the protein kinase RIP3 gets recruited to the complex, forming a necrosome, which will lead to necroptotic cell death initiation [8-10]. Once the necrosome is formed, RIP1 and RIP3 engage in a series of auto and cross phosphorylation events that are essential for necroptotic cell death. Necroptosis can be completely blocked either by the kinase inactivating mutation in any of the two kinases, or chemically by RIP1 kinase inhibitors (necrostatins), or RIP3 kinase inhibitors [11-13]. Phosphorylation of RIP3 allows the binding and phosphorylation of pseudokinase MLKL (mixed lineage kinase domain-like), a key component of necroptotic cell death [14, 15].

Necroptosis has crucial pathophysiological relevance in myocardial infarction, stroke, atherosclerosis, ischemia-reperfusion injury, inflammatory bowel diseases, retinal degeneration and a number of other common clinical disorders [16]. Therefore, selective inhibitors of RIP1 kinase activity are therefore desired as a potential treatment of diseases mediated by this pathway and associated with inflammation and/or necroptotic cell death.

Inhibitors of RIP1 kinase have been previously described. The first published inhibitor of RIP1 kinase activity was necrostatin 1 (Nec-1) [17]. This initial discovery was followed by modified versions of Nec-1 with various abilities to block RIP1 kinase activity [11, 18]. Recently, additional RIP1 kinase inhibitors have been described that differ structurally from necrostatin class of compounds [19, 20, 21].

References cited above, each of which is hereby incorporated by reference in its entirety:

1) Vanden Berghe, T., Linkermann, A., Jouan-Lanhouet, S., Walczak, H. and Vandenabeele, P. (2014) Regulated necrosis: the expanding network of non-apoptotic cell death pathways. Nature reviews. Molecular cell biology. 15, 135-147.
2) Newton, K. (2015) RIPK1 and RIPK3: critical regulators of inflammation and cell death. Trends in cell biology. 25, 347-353.
3) de Almagro, M. C. and Vucic, D. (2015) Necroptosis: Pathway diversity and characteristics. Semin Cell Dev Biol. 39, 56-62.
4) Chen, Z. J. (2012) Ubiquitination in signaling to and activation of IKK. Immunological reviews. 246, 95-106.
5) O'Donnell, M. A., Legarda-Addison, D., Skountzos, P., Yeh, W. C. and Ting, A. T. (2007) Ubiquitination of RIP1 regulates an NF-kappaB-independent cell-death switch in TNF signaling. Curr Biol. 17, 418-424.
6) Feoktistova, M., Geserick, P., Kellert, B., Dimitrova, D. P., Langlais, C., Hupe, M., Cain, K., MacFarlane, M., Hacker, G. and Leverkus, M. (2011) cIAPs block Ripoptosome formation, a RIP1/caspase-8 containing intracellular cell death complex differentially regulated by cFLIP isoforms. Molecular cell. 43, 449-463.
7) Bertrand, M. J., Milutinovic, S., Dickson, K. M., Ho, W. C., Boudreault, A., Durkin, J., Gillard, J. W., Jaquith, J. B., Morris, S. J. and Barker, P. A. (2008) cIAP1 and cIAP2 facilitate cancer cell survival by functioning as E3 ligases that promote RIP1 ubiquitination. Mol Cell. 30, 689-700.
8) Wang, L., Du, F. and Wang, X. (2008) TNF-alpha induces two distinct caspase-8 activation pathways. Cell. 133, 693-703.
9) He, S., Wang, L., Miao, L., Wang, T., Du, F., Zhao, L. and Wang, X. (2009) Receptor interacting protein kinase-3 determines cellular necrotic response to TNF-alpha. Cell. 137, 1100-1111.
10) Cho, Y. S., Challa, S., Moquin, D., Genga, R., Ray, T. D., Guildford, M. and Chan, F. K. (2009) Phosphorylation-driven assembly of the RIP1-RIP3 complex regulates programmed necrosis and virus-induced inflammation. Cell. 137, 1112-1123.
11) Degterev, A., Hitomi, J., Germscheid, M., Chien, I. L., Korkina, O., Teng, X., Abbott, D., Cuny, G. D., Yuan, C., Wagner, G., Hedrick, S. M., Gerber, S. A., Lugovskoy, A. and Yuan, J. (2008) Identification of RIP1 kinase as a specific cellular target of necrostatins. Nat Chem Biol. 4, 313-321.
12) Newton, K., Dugger, D. L., Wickliffe, K. E., Kapoor, N., de Almagro, M. C., Vucic, D., Komuves, L., Ferrando, R. E., French, D. M., Webster, J., Roose-Girma, M., Warming, S. and Dixit, V. M. (2014) Activity of protein kinase RIPK3 determines whether cells die by necroptosis or apoptosis. Science. 343, 1357-1360.
13) Kaiser, W. J., Sridharan, H., Huang, C., Mandal, P., Upton, J. W., Gough, P. J., Sehon, C. A., Marquis, R. W., Bertin, J. and Mocarski, E. S. (2013) Toll-like receptor 3-mediated necrosis via TRIF, RIP3, and MLKL. The Journal of biological chemistry. 288, 31268-31279.
14) Zhao, J., Jitkaew, S., Cai, Z., Choksi, S., Li, Q., Luo, J. and Liu, Z. G. (2012) Mixed lineage kinase domain-like is a key receptor interacting protein 3 downstream component of TNF-induced necrosis. Proceedings of the National Academy of Sciences of the United States of America. 109, 5322-5327.
15) Sun, L., Wang, H., Wang, Z., He, S., Chen, S., Liao, D., Wang, L., Yan, J., Liu, W., Lei, X. and Wang, X. (2012) Mixed Lineage Kinase Domain-like Protein Mediates Necrosis Signaling Downstream of RIP3 Kinase. Cell. 148, 213-227.
16) Linkermann, A. and Green, D. R. (2014) Necroptosis. The New England journal of medicine. 370, 455-465.
17) Degterev, A., Huang, Z., Boyce, M., Li, Y., Jagtap, P., Mizushima, N., Cuny, G. D., Mitchison, T. J., Moskowitz, M. A. and Yuan, J. (2005) Chemical inhibitor of nonapoptotic cell death with therapeutic potential for ischemic brain injury. Nat Chem Biol. 1, 112-119.
18) Takahashi, N., Duprez, L., Grootjans, S., Cauwels, A., Nerinckx, W., DuHadaway, J. B., Goossens, V., Roelandt, R., Van Hauwermeiren, F., Libert, C., Declercq, W., Callewaert, N., Prendergast, G. C., Degterev, A., Yuan, J. and Vandenabeele, P. (2012) Necrostatin-1 analogues: critical issues on the specificity, activity and in vivo use in experimental disease models. Cell Death Dis. 3, e437.
19) Harris, P. A., Bandyopadhyay, D., Berger, S. B., Campobasso, N., Capriotti, C. A., Cox, J. A., Dare, L., Finger, J. N., Hoffman, S. J., Kahler, K. M., Lehr, R., Lich, J. D., to Nagilla, R., Nolte, R. T., Ouellette, M. T., Pao, C. S., Schaeffer, M. C., Smallwood, A., Sun, H. H., Swift, B. A., Totoritis, R. D., Ward, P., Marquis, R. W., Bertin, J. and Gough, P. J. (2013) Discovery of Small Molecule RIP1 Kinase Inhibitors for the Treatment of Pathologies Associated with Necroptosis. ACS medicinal chemistry letters. 4, 1238-1243.
20) Najjar, M., Suebsuwong, C., Ray, S. S., Thapa, R. J., Maki, J. L., Nogusa, S., Shah, S., Saleh, D., Gough, P. J., Bertin, J., Yuan, J., Balachandran, S., Cuny, G. D. and Degterev, A. (2015) Structure Guided Design of Potent and Selective Ponatinib-Based Hybrid Inhibitors for RIPK1. Cell Rep.
21) International Patent Publication No. WO 2014/125444.

SUMMARY OF THE INVENTION

Provided herein are compounds of formula I:

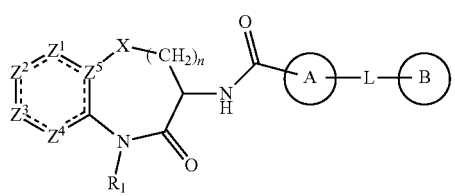

(I)

or pharmaceutically acceptable salts thereof, wherein
$R^1$ is selected from the group consisting of H, $C_1$-$C_4$ alkyl and $C_1$-$C_4$ haloalkyl;
the A ring is tetrazolyl, or a 5 or 6 membered heteroaryl having 1 to 3 heteroatoms selected from the group consisting of nitrogen, oxygen and sulfur; wherein the A ring is optionally substituted with 1 to 2 substituents selected from the group consisting of halogen, $C_1$-$C_4$ alkyl, $C_3$-$C_4$ cycloalkyl, $C_1$-$C_4$ haloalkyl, $C_1$-$C_4$ alkoxy, $C_1$-$C_4$ haloalkoxy and cyano; and wherein if a nitrogen atom in the A ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom;
the B ring is selected from the group consisting of phenyl, 5 or 6 membered heteroaryl, 3 to 7 membered cycloalkyl, and 4 to 7 membered heterocyclyl; wherein the B ring is optionally substituted with:
  (a) 1 to 4 substituents selected from the group consisting of halogen, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, cyano, phenyl, benzyl, $CH_2$—($C_3$-$C_6$ cycloalkyl), and $CH_2CH_2$—($C_3$-$C_6$ cycloalkyl); wherein if a nitrogen atom in the C ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom;
  (b) 1 to 2 substituents selected from the group consisting of $C_1$-$C_6$ alkyl, $C_1$-$C_6$ haloalkyl, $C_1$-$C_6$ alkoxy, $C_1$-$C_6$ haloalkoxy, $CH_2$-(4 to 6 membered heterocyclyl), $CH_2CH_2$-(4 to 6 membered heterocyclyl), and unsubstituted 5 or 6 membered heteroaryl; or
  (c) two adjacent substituents which together form phenyl, 5 or 6 membered heteroaryl, 4 to 6 membered heterocyclyl or $C_4$-$C_6$ cycloalkyl;
L is selected from the group consisting of a bond, O, S, NH, $NCH_3$, $(CH_2)_m$, $CH(CH_3)$, $C(CH_3)_2$, $CF_2$, $CH_2O$, $CH_2S$, $CH(OH)$, $CH_2NH$, and $CH_2N(CH_3)$, or L is absent such that the A ring and the B ring are fused;
X is selected from the group consisting of O, S, SO, $SO_2$, $CH_2$, $C(CH_3)_2$, $CF_2$ and $CHCF_3$;
each of $Z^1$ to $Z^4$ is independently selected from the group consisting of $CR^2$, $NR^3$ and C=O;
$Z^5$ is C or N;
wherein only one of $Z^1$ to $Z^4$ is C=O; and:
  (i) if $Z^1$ is C=O and $Z^5$ is N, then $Z^2$, $Z^3$, $Z^4$ are each $CR^2$ and X is $CH_2$;
  (ii) if $Z^1$ is C=O and $Z^2$ is N, then $Z^3$ and $Z^4$ are each $CR^2$ and $Z^5$ is C;
  (iii) if $Z^2$ is C=O and $Z^1$ is $NR^3$, then $Z^3$ and $Z^4$ are each $CR^2$ and $Z^5$ is C;
  (iv) if $Z^2$ is C=O and $Z^3$ is $NR^3$, then $Z^1$ and $Z^4$ are each $CR^2$ and $Z^5$ is C;
  (v) if $Z^3$ is C=O and $Z^2$ is $NR^3$, then $Z^1$ and $Z^4$ are each $CR^2$ and $Z^5$ is C;
  (vi) if $Z^3$ is C=O and $Z^4$ is $NR^3$, then $Z^1$ and $Z^2$ are each $CR^2$ and $Z^5$ is C;
  (vii) if $Z^4$ is C=O and $Z^3$ is $NR^3$, then $Z^1$ and $Z^2$ are each $CR^2$ and $Z^5$ is C;
n is 1 or 2;
$R^2$ is selected from the group consisting of H, F, $C_1$-$C_6$ alkyl, $C_1$-$C_6$ alkoxy, and $C_1$-$C_6$ haloalkyl;
$R^3$ is selected from the group consisting of H, $C_1$-$C_6$ alkyl, $C_1$-$C_6$ haloalkyl, $C_1$-$C_6$ alkoxy, $C_3$-$C_6$ cycloalkyl, —$C(R^4)_2$—$C_3$-$C_6$ cycloalkyl, 4 to 6 membered heterocyclyl, and —$C(R^4)_2$-(4 to 6 membered heterocyclyl); and
each $R^4$ is independently selected from the group consisting of H, F, $C_1$-$C_6$ alkyl, $C_1$-$C_6$ alkoxy, and $C_1$-$C_6$ haloalkyl;
provided that if the A ring is tetrazolyl, L is selected from the group consisting of $CH_2$, $CH(CH_3)$, $C(CH_3)_2$, $CF_2$; and B ring is phenyl.

In the following description, all references to formula I also include subembodiments of formula I (i.e., formulae 1a, 1b, etc.).

Also provided herein are pharmaceutical compositions comprising a compound of formula I, or a pharmaceutically acceptable salt thereof, and one or more pharmaceutically acceptable carriers or excipients. Specific embodiments include pharmaceutical compositions suitable for intravenous or oral delivery.

Also provided herein are oral formulations of a compound of formula I, or a pharmaceutically acceptable salt thereof, and one or more pharmaceutically acceptable carriers or excipients suitable for oral delivery.

Also provided herein are parenteral formulations of a compound of formula I, or a pharmaceutically acceptable salt thereof, and one or more pharmaceutically acceptable carriers or excipients suitable for parenteral delivery.

In some embodiments, provided herein are uses of a compound of formula I, or a pharmaceutically acceptable salt thereof, for the treatment of diseases and disorders. In some embodiments, the diseases and disorders to be treated are selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cisplatin-induced kidney injury, sepsis, systemic inflammatory response syndrome (SIRS), pancreatitis, psoriasis, retinitis pigmentosa, retinal degeneration, chronic kidney diseases, acute respiratory distress syndrome (ARDS), chronic obstructive pulmonary disease (COPD).

In some embodiments, the disease or disorder to be treated is selected from the group consisting of inflammatory bowel diseases (including Crohn's disease and ulcerative colitis), psoriasis, retinal detachment, retinitis pigmentosa, macular degeneration, pancreatitis, atopic dermatitis, arthritis (including rheumatoid arthritis, osteoarthritis, spondylarthritis, gout, systemic onset juvenile idiopathic arthritis (SoJIA), psoriatic arthritis), systemic lupus erythematosus (SLE), Sjogren's syndrome, systemic scleroderma, antiphospholipid syndrome (APS), vasculitis, liver damage/diseases (non-alcohol steatohepatitis, alcohol steatohepatitis, autoimmune hepatitis autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury (AKI)), Celiac disease, autoimmune idiopathic thrombocytopenic purpura, transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), spinal muscular atropy (SMA), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), periodontitis, NEMO-deficiency syndrome (F-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2, Gangliosidosis, Alpha-mannosidosis, Aspartylglucosaminuria, Cholesteryl Ester storage disease, Chronic Hexosaminidase A Deficiency, Cystinosis, Danon disease, Fabry disease, Farber disease, Fucosidosis, Galac-
tosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease).

In some embodiments, the diseases and disorders to be treated are selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cisplatin-induced kidney injury, sepsis, systemic inflammatory response syndrome (SIRS), pancreatitis, psoriasis, retinitis pigmentosa and retinal degeneration.

In some embodiments, provided herein are methods for the treatment or prevention of a disease or disorder with a therapeutically effective amount of a compound of formula I, or a pharmaceutically acceptable salt thereof, wherein the disease or disorder is associated with inflammation and/or necroptosis. In some embodiments said disease or disorder is selected from the specific diseases and disorders recited herein.

In some embodiments, provided herein are methods of inhibiting RIP1 kinase activity by contacting a cell with a compound of formula I or a pharmaceutically acceptable salt thereof.

DETAILED DESCRIPTION OF THE INVENTION

Definitions

As provided herein, all chemical formulae and generic chemical structures should be interpreted to provide proper valence and chemically stable bonds between atoms as understood by one of ordinary skill in the art. Where appropriate, substituents may be bonded to more than one adjacent atom (e.g., alkyl includes methylene where two bonds are present).

In the chemical formulae provided herein, "halogen" or "halo' refers to fluorine, chlorine, and bromine (i.e., F, Cl, Br).

Alkyl, unless otherwise specifically defined, refers to an optionally substituted, straight-chain or branched $C_1$-$C_{12}$ alkyl group. In some embodiments, alkyl refers to a $C_1$-$C_6$ alkyl group. Exemplary alkyl groups include methyl, ethyl, propyl, iso-propyl, n-butyl, iso-butyl, tert-butyl, sec-butyl, n-pentyl, n-hexyl, n-heptyl, and n-oxtyl. Substituted alkyl groups provided herein are substituted by one or more substituents selected from the group consisting of halogen, cyano, trifluoromethyl, methoxy, ethoxy, difluoromethoxy, trifluoromethoxy, $C_3$-$C_6$ cycloalkyl, phenyl, OH, $CO_2H$, $CO_2(C_1$-$C_4$ alkyl), $NH_2$, $NH(C_1$-$C_4$ alkyl), $N(C_1$-$C_4$ alkyl)$_2$, $NH(C=O)C_1$-$C_4$ alkyl, $(C=O)NH(C_1$-$C_4$ alkyl), $(C=O)N(C_1$-$C_4$ alkyl)$_2$, $S(C_1$-$C_4$ alkyl), $SO(C_1$-$C_4$ alkyl), $SO_2(C_1$-$C_4$ alkyl), $SO_2NH(C_1$-$C_4$ alkyl), $SO_2N(C_1$-$C_4$ alkyl)$_2$, and $NHSO_2(C_1$-$C_4$ alkyl). In some embodiments, the substituted alkyl group has 1 or 2 substituents. In some embodiments, the alkyl group is unsubstituted.

Cycloalkyl, unless otherwise specifically defined, refers to an optionally substituted $C_3$-$C_{12}$ cycloalkyl group and includes fused, spirocyclic, and bridged bicyclic groups, wherein the substituents are selected from the group consisting of halogen, cyano, trifluoromethyl, methoxy, ethoxy, difluoromethoxy, trifluoromethoxy, $C_3$-$C_6$ cycloalkyl, phenyl, OH, $CO_2H$, $CO_2(C_1$-$C_4$ alkyl), $NH_2$, $NH(C_1$-$C_4$ alkyl), $N(C_1$-$C_4$ alkyl)$_2$, $NH(C=O)C_1$-$C_4$ alkyl, $(C=O)NH(C_1$-$C_4$ alkyl), $(C=O)N(C_1$-$C_4$ alkyl)$_2$, $S(C_1$-$C_4$ alkyl), $SO(C_1$-$C_4$ alkyl), $SO_2(C_1$-$C_4$ alkyl), $SO_2NH(C_1$-$C_4$ alkyl), $SO_2N(C_1$-$C_4$ alkyl)$_2$, and $NHSO_2(C_1$-$C_4$ alkyl). In some embodiments, cycloalkyl refers to a $C_3$-$C_6$ cycloalkyl group. In some embodiments, the $C_3$-$C_6$ cycloalkyl group is optionally substituted with 1 to three halogen atoms. In some embodiments, the $C_3$-$C_6$ cycloalkyl group is optionally substituted with 1 to three fluorine atoms. Exemplary $C_3$-$C_6$ cycloalkyl groups include cyclopropyl, cyclobutyl, cyclopentyl and cyclohexyl. Exemplary $C_3$-$C_{12}$ cycloalkyl groups further include bicyclo[3.1.0]hexyl, bicyclo[2.1.1]hexyl, cycloheptyl, bicycle[4.1.0]heptyl, spiro[4.2]heptyl, cyclooctyl, spiro[4.3]octyl, spiro[5.2]octyl, bicyclo[2.2.]heptanyl, bicycle[2.2.2]octanyl, adamantanyl, decalinyl, and spiro[5.4]decanyl. Where appropriate, cycloalkyl groups may be fused to other groups such that more than one chemical bond exists between the cycloalkyl group and another ring system (e.g., the C ring of formula I). In some embodiments, the cycloalkyl group is unsubstituted.

Haloalkyl, unless otherwise specifically defined, refers to a straight-chain or branched $C_1$-$C_{12}$ alkyl group, wherein one or more hydrogen atoms are replaced by a halogen. In some embodiments, haloalkyl refers to a $C_1$-$C_6$ haloalkyl group. In some embodiments, 1 to 3 hydrogen atoms of the haloalkyl group are replaced by a halogen. In some embodiments, every hydrogen atom of the haloalkyl group is replaced by a halogen (e.g, trifluoromethyl). In some embodiments, the haloalkyl is as defined herein wherein the halogen in each instance is fluorine. Exemplary haloalkyl groups include fluoromethyl, difluoromethyl, trifluromethyl, trifluoroethyl, and pentafluoroethyl.

Alkoxy, unless otherwise specifically defined, refers to a straight-chain or branched $C_1$-$C_{12}$ alkyl group, wherein one or more oxygen atoms are present, in each instance between two carbon atoms. In some embodiments, alkoxy refers to a $C_1$-$C_6$ alkoxy group. In some embodiments, $C_1$-$C_6$ alkoxy groups provided herein have one oxygen atom. Exemplary alkoxy groups include methoxy, ethoxy, $CH_2OCH_3$, $CH_2CH_2OCH_3$, $CH_2OCH_2CH_3$, $CH_2CH_2OCH_2CH_3$, $CH_2OCH_2CH_2CH_3$, $CH_2CH_2CH_2OCH_3$, $CH_2OCH(CH_3)_2$, $CH_2OC(CH_3)_3$, $CH(CH_3)OCH_3$, $CH_2CH(CH_3)OCH_3$, $CH(CH_3)OCH_2CH_3$, $CH_2OCH_2OCH_3$, $CH_2CH_2OCH_2CH_2OCH_3$, and $CH_2OCH_2OCH_2OCH_3$.

Cycloalkoxy, unless otherwise specifically defined, refers to a $C_4$-$C_{10}$ or a $C_4$-$C_6$ alkoxy group as defined above wherein the group is cyclic and contains one oxygen atom. Exemplary cycloalkoxy groups include oxetanyl, tetrahydrofuranyl, and tetrahydropyranyl.

Haloalkoxy, unless otherwise specifically defined, refers to a $C_1$-$C_6$ haloalkyl group as defined above, wherein one or two oxygen atoms are present, in each instance between two carbon atoms. In some embodiments, $C_1$-$C_6$ haloalkoxy groups provided herein have one oxygen atom. Exemplary haloalkoxy groups include $OCF_3$, $OCHF_2$ and $CH_2OCF_3$.

Thioalkyl, unless otherwise specifically defined, refers to a $C_1$-$C_{12}$ or a $C_1$-$C_6$ alkoxy group as defined above wherein the oxygen atom is replaced by a sulfur atom. In some embodiments, thioalkyl groups may include sulfur atoms substituted by one or two oxygen atoms (i.e., alkylsulfones and alkylsulfoxides). Exemplary thioalkyl groups are those exemplified in the definition of alkoxy above, wherein each oxygen atom is replaced by a sulfur atom in each instance.

Thiocycloalkyl, unless otherwise specifically defined, refers to a $C_4$-$C_{10}$ or a $C_4$-$C_6$ thioalkyl group as defined above wherein the group is cyclic and contains one sulfur atom. In some embodiments, the sulfur atom of the thiocycloalkyl group is substituted by one or two oxygen atoms (i.e., a cyclic sulfone or sulfoxide). Exemplary thiocycloalkyl groups include thietanyl, thiolanyl, thianyl, 1,1-dioxothiolanyl, and 1,1-dioxothianyl.

Heterocyclyl, unless otherwise specifically defined, refers to a single saturated or partially unsaturated 4 to 8 membered ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems have from 7 to 12 atoms and are further described below. Thus, the term includes single saturated or partially unsaturated rings (e.g., 3, 4, 5, 6, 7 or 8 membered rings) from about 1 to 7 carbon atoms and from about 1 to 4 heteroatoms selected from the group consisting of oxygen, nitrogen and sulfur in the ring. The ring may be C-branched (i.e., substituted by $C_1$-$C_4$ alkyl). The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system. It is also to be understood that the point of attachment for a heterocycle or heterocycle multiple condensed ring system can be at any suitable atom of the heterocyclyl group including a carbon atom and a nitrogen atom. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one N-methylpiperidine, imidazolidine, pyrazolidine, butyrolactam, valerolactam, imidazolidinone, hydantoin, dioxolane, phthalimide, 1,4-dioxane, thiomorpholine, thiomorpholine-S-oxide, thiomorpholine-S,S-oxide, pyran, 3-pyrroline, thiopyran, pyrone, tetrhydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo[2.2.2]octane and pyrrolidin-2-one.

In some embodiments, the heterocyclyl is a $C_4$-$C_{10}$ heterocyclyl having 1 to 3 heteroatoms selected from the group consisting of nitrogen, oxygen and sulfur. In some embodiments, the heterocyclyl group is neither bicyclic nor spirocyclic. In some embodiments, the heterocyclyl is a $C_5$-$C_6$ heterocyclyl having 1 to 3 heteroatoms, wherein at least 2 are nitrogen if 3 heteroatoms are present.

Aryl, unless otherwise specifically defined, refers to a single all carbon aromatic ring or a multiple condensed all carbon ring system wherein at least one of the rings is aromatic and wherein the aryl group has 6 to 20 carbon atoms, 6 to 14 carbon atoms, 6 to 12 carbon atoms, or 6 to 10 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Exemplary aryl groups include phenyl, indenyl, naphthyl, 1,2, 3,4-tetrahydronaphthyl, anthracenyl, and the like.

Heteroaryl, unless otherwise specifically defined, refers to a 5 to 6 membered aromatic ring that has at least one atom other than carbon in the ring, wherein the atom is selected from the group consisting of oxygen, nitrogen and sulfur; "heteroaryl" also includes multiple condensed ring systems having 8 to 16 atoms that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2 or 3 rings) wherein a heteroaryl group, as defined above, is condensed with one or more rings selected from heteroaryls (to form for example a naphthyridinyl such as 1,8-naphthyridinyl), heterocycles, (to form for example a 1,2,3,4-tetrahydronaphthyridinyl such as 1,2, 3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has 1 to 15 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system. It is also to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclo-penta[1,2-c]pyrazole.

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line " $\sim\!\!\sim\!\!\sim$ " that intersects a bond in a chemical structure indicates the point of attachment of the bond that the wavy bond intersects in the chemical structure to the remainder of a molecule.

As used herein, the term "C-linked" means that the group that the term describes is attached the remainder of the molecule through a ring carbon atom.

As used herein, the term "N-linked" means that the group that the term describes is attached to the remainder of the molecule through a ring nitrogen atom.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 97% the absolute stereoisomer depicted. In another embodiment, the compound may be at least 98% the absolute stereoisomer depicted. In another embodiment, the compound may be at least 99% the absolute stereoisomer depicted.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4th edition, Wiley-Interscience, New York, 2006.

As used herein, the term "mammal" includes, but is not limited to, humans, mice, rats, guinea pigs, monkeys, dogs, cats, horses, cows, pigs, and sheep.

As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-$((C_{1-6})$alkanoyloxy)ethyl, 1-methyl-1-$((C_{1-6})$alkanoyloxy)ethyl, $(C_{1-6})$alkoxycarbonyloxymethyl, N—$(C_{1-6})$ alkoxycarbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})$alkyl$)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^3H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" or "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

Inhibitors of RIP1 Kinase

The present invention provides novel compounds having the general formula I:

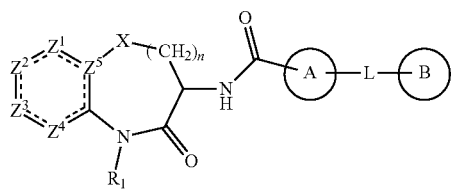

(I)

or pharmaceutically acceptable salts thereof, wherein $R^1$ is selected from the group consisting of H, $C_1$-$C_4$ alkyl and $C_1$-$C_4$ haloalkyl;

the A ring is tetrazolyl or a 5 or 6 membered heteroaryl having 1 to 3 heteroatoms selected from the group consisting of nitrogen, oxygen and sulfur; wherein the A ring is optionally substituted with 1 to 2 substituents selected from the group consisting of halogen, $C_1$-$C_4$ alkyl, $C_3$-$C_4$ cycloalkyl, $C_1$-$C_4$ haloalkyl, $C_1$-$C_4$ alkoxy, $C_1$-$C_4$ haloalkoxy and cyano; and wherein if a nitrogen atom in the A ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom;

the B ring is selected from the group consisting of phenyl, 5 or 6 membered heteroaryl, 3 to 7 membered cycloalkyl, and 4 to 7 membered heterocyclyl; wherein the B ring is optionally substituted with:

(a) 1 to 4 substituents selected from the group consisting of halogen, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, cyano, phenyl, benzyl, $CH_2$—($C_3$-$C_6$ cycloalkyl), and $CH_2CH_2$—($C_3$-$C_6$ cycloalkyl); wherein if a nitrogen atom in the C ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom;

(b) 1 to 2 substituents selected from the group consisting of $C_1$-$C_6$ alkyl, $C_1$-$C_6$ haloalkyl, $C_1$-$C_6$ alkoxy, $C_1$-$C_6$ haloalkoxy, $CH_2$-(4 to 6 membered heterocyclyl), $CH_2CH_2$-(4 to 6 membered heterocyclyl), and unsubstituted 5 or 6 membered heteroaryl; or (c) two adjacent substituents which together form phenyl, 5 or 6 membered heteroaryl, 4 to 6 membered heterocyclyl or $C_4$-$C_6$ cycloalkyl;

L is selected from the group consisting of a bond, O, S, NH, $NCH_3$, $(CH_2)_m$, $CH(CH_3)$, $C(CH_3)_2$, $CF_2$, $CH_2O$, $CH_2S$, $CH(OH)$, $CH_2NH$, and $CH_2N(CH_3)$, or L is absent such that the A ring and the B ring are fused;

X is selected from the group consisting of O, S, SO, $SO_2$, $CH_2$, $C(CH_3)_2$, $CF_2$ and $CHCF_3$;

each of $Z^1$ to $Z^4$ is independently selected from the group consisting of $CR^2$, $NR^3$ and C=O;

$Z^5$ is C or N;

wherein only one of $Z^1$ to $Z^4$ is C=O; and:

(i) if $Z^1$ is C=O and $Z^5$ is N, then $Z^2$, $Z^3$, $Z^4$ are each $CR^2$ and X is $CH_2$;

(ii) if $Z^1$ is C=O and $Z^2$ is N, then $Z^3$ and $Z^4$ are each $CR^2$ and $Z^5$ is C;

(iii) if $Z^2$ is C=O and $Z^1$ is $NR^3$, then $Z^3$ and $Z^4$ are each $CR^2$ and $Z^5$ is C;

(iv) if $Z^2$ is C=O and $Z^3$ is $NR^3$, then $Z^1$ and $Z^4$ are each $CR^2$ and $Z^5$ is C;

(v) if $Z^3$ is C=O and $Z^2$ is $NR^3$, then $Z^1$ and $Z^4$ are each $CR^2$ and $Z^5$ is C;

(vi) if $Z^3$ is C=O and $Z^4$ is $NR^3$, then $Z^1$ and $Z^2$ are each $CR^2$ and $Z^5$ is C;

(vii) if $Z^4$ is C=O and $Z^3$ is $NR^3$, then $Z^1$ and $Z^2$ are each $CR^2$ and $Z^5$ is C;

n is 1 or 2;

$R^2$ is selected from the group consisting of H, F, $C_1$-$C_6$ alkyl, $C_1$-$C_6$ alkoxy, and $C_1$-$C_6$ haloalkyl;

$R^3$ is selected from the group consisting of H, $C_1$-$C_6$ alkyl, $C_1$-$C_6$ haloalkyl, $C_1$-$C_6$ alkoxy, $C_3$-$C_6$ cycloalkyl, —$C(R^4)_2$—$C_3$-$C_6$ cycloalkyl, 4 to 6 membered heterocyclyl, and —$C(R^4)_2$-(4 to 6 membered heterocyclyl); and each $R^4$ is independently selected from the group consisting of H, F, $C_1$-$C_6$ alkyl, $C_1$-$C_6$ alkoxy, and $C_1$-$C_6$ haloalkyl;

provided that if the A ring is tetrazolyl, L is selected from the group consisting of $CH_2$, $CH(CH_3)$, $C(CH_3)_2$, $CF_2$; and B ring is phenyl.

Also provided herein are compounds of Formula (I), having the formulae:

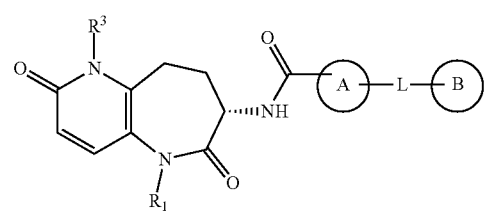

(Ia)

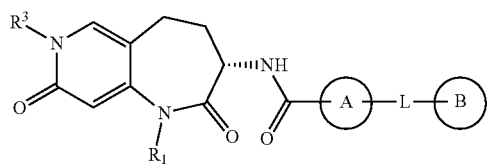

(Ib)

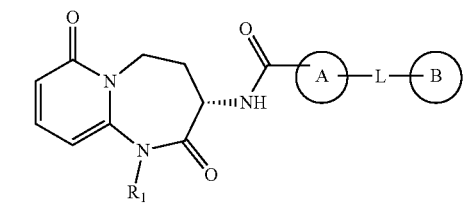

(Ic)

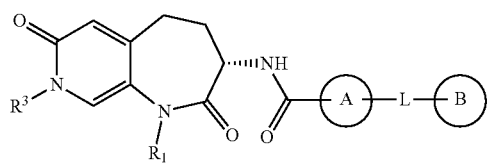

(Id)

wherein $R^1$, $R^3$, $R^4$, ring A, ring B and L are as defined herein.

In some embodiments, $R^1$ is selected from the group consisting of H, methyl, ethyl and isopropyl. In some embodiments, $R^1$ is H. In other embodiments, $R^1$ is methyl.

In some embodiments, $R^3$ is selected from the group consisting of H, $C_1$-$C_6$ alkyl, $C_1$-$C_6$ haloalkyl, $C_3$-$C_6$ cycloalkyl, —$CH_2$—$C_3$-$C_6$ cycloalkyl, 4 to 6 membered heterocyclyl, and $CH_2$-(4 to 6 membered heterocyclyl). In some embodiments, $R^3$ is selected from the group consisting of H, methyl, ethyl, and —$CH_2$-cyclopropyl. In some embodiments, $R^3$ is H. In other embodiments, $R^3$ is methyl.

In some embodiments, each $R^4$ is independently selected from the group consisting of H, F, methyl, mono-, di- and tri-fluoromethyl. In some embodiments, each $R^4$ is H In some embodiments, X is $CH_2$. In some embodiments, X is $CF_2$. In some embodiments, X is O.

In some embodiments, L is $(CH_2)_m$ and m is 1 or 2. In some embodiments, L is $(CH_2)_m$ and m is 1. In other embodiments, L is absent such that the A ring and the B ring are fused.

In some embodiments, n is 1.

In some embodiments, the A ring is a 5 or 6 membered heteroaryl having from 1 to 3 nitrogen atoms in the ring. In other embodiments, the A ring is a 5 or 6 membered heteroaryl having from 1 to 2 nitrogen atoms and from 0 to 1 oxygen or sulfur atoms in the ring. In some embodiments, the A ring is selected from the group consisting of furanyl, pyrroyl, thiopheneyl, pyrazolyl, imidazolyl, oxazolyl, isoxazolyl, thiazolyl, isothiazolyl and triazolyl. In some embodiments, the A ring is pyrazolyl. In some embodiments, the A ring is imidazolyl. In some embodiments, the A ring is oxazolyl. In some embodiments, the A ring is thiazolyl. In some embodiments, the A ring is triazolyl. In some embodiments, the A ring is oxadiazolyl. In some embodiments, the A ring is pyridinyl or pyrimidinyl. In some embodiments of this paragraph, the A ring is unsubstituted.

In some embodiments wherein L is present, the B ring is phenyl substituted by 1 or 2 substituents selected from the group consisting of halogen, $C_1$-$C_4$ alkyl, and $C_1$-$C_4$ alkoxy. In other embodiments wherein L is present, the B ring is mono- or di-fluoro substituted phenyl. In other embodiments wherein L is present, the B ring is unsubstituted phenyl.

In some embodiments, L is $CH_2$, the A ring is triazolyl, and the B ring is substituted or unsubstituted phenyl. In some embodiments, L is $CH_2$, the A ring is triazolyl, and the B ring is unsubstituted phenyl. In some embodiments, L is $CH_2$, the A ring is triazolyl, and the B ring is mono- or di-fluoro substituted phenyl In some embodiments wherein L is absent such that the A and B rings are fused, the A ring is a 5 or 6 membered heteroaryl having from 1 to 3 nitrogen atoms in the ring, and the B ring is a 5 to 7 membered heterocyclyl containing 0 to 1 heteroatoms selected from the group consisting of nitrogen, oxygen and sulfur. In other embodiments wherein L is absent such that the A and B rings are fused, the A ring is a 5 or 6 membered heteroaryl having from 1 to 3 nitrogen atoms in the ring, and the B ring is a 5 to 7 membered cycloalkyl. In other embodiments wherein L is absent such that the A and B rings are fused, the A ring is triazolyl and the B ring is a 5 to 7 membered cycloalkyl. In some embodiments of this paragraph, the B ring is substituted by phenyl, said phenyl being optionally substituted by halogen, $C_1$-$C_4$ alkyl, or $C_1$-$C_4$ alkoxy. In some embodiments of this paragraph, the B ring is unsubstituted.

In some embodiments, provided herein is a compound of formula I, Ia, Ib, Ic or Id, wherein

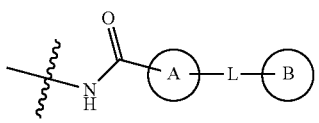

is selected from the group consisting of:

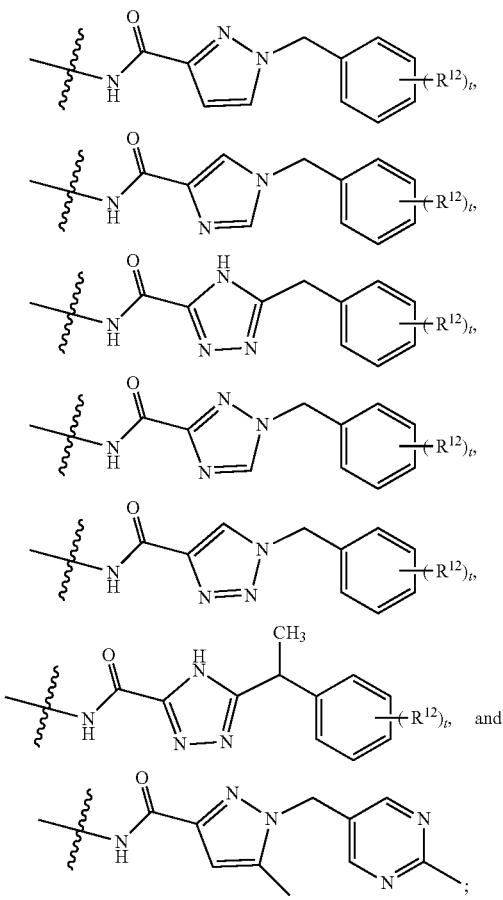

wherein $R^{12}$ is selected from the group consisting of halogen and methyl; and t is 0, 1 or 2.

In some embodiments, $R^{12}$ is fluoro and t is 1 or 2. In some embodiments, t is 0.

In some embodiments, provided herein is a compound of formula I, Ia, Ib, Ic or Id, wherein

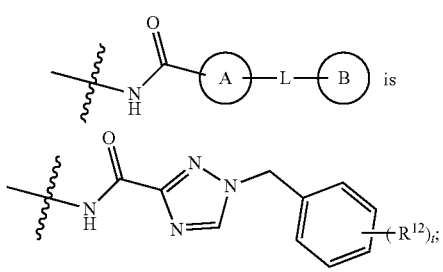

wherein $R^{12}$ and t are as defined above. In some embodiments, each $R^{12}$ is selected from fluoro and chloro. In some embodiments, each $R^{12}$ is F and t is 1 or 2.

In some embodiments, provided herein is a compound of formula I, Ia, Ib, Ic or Id, wherein

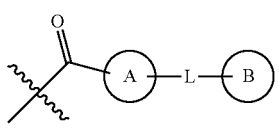

is selected from the group consisting of:

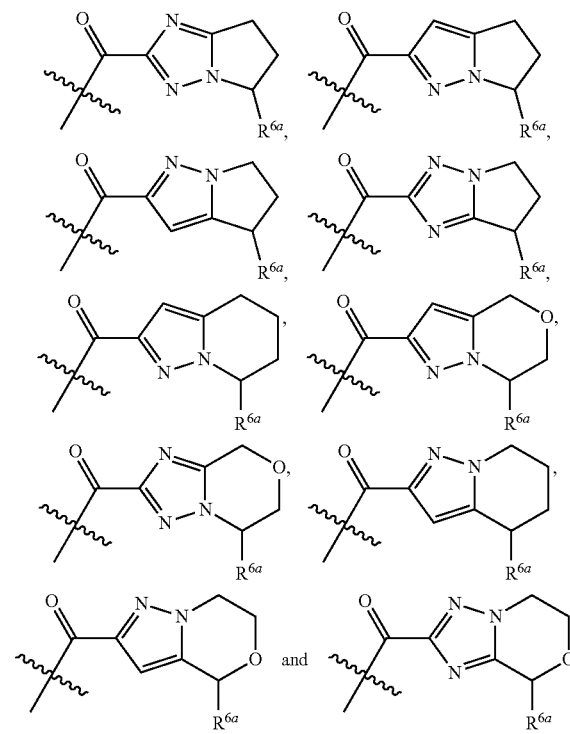

wherein $R^{6a}$ is selected from the group consisting of H, $C_1$-$C_6$ alkyl, $C_3$-$C_6$ cycloalkyl, $C_1$-$C_6$ haloalkyl, phenyl and fluorophenyl. In some embodiments, $R^{6a}$ is phenyl. In some embodiments, $R^{6a}$ is mono- or di-fluorophenyl.

In some embodiments, provided herein is a compound of formula I, Ia, Ib, Ic or Id, wherein

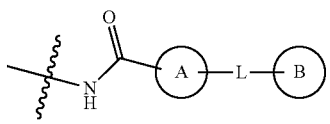

is selected from the group consisting of:

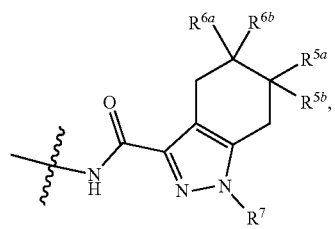

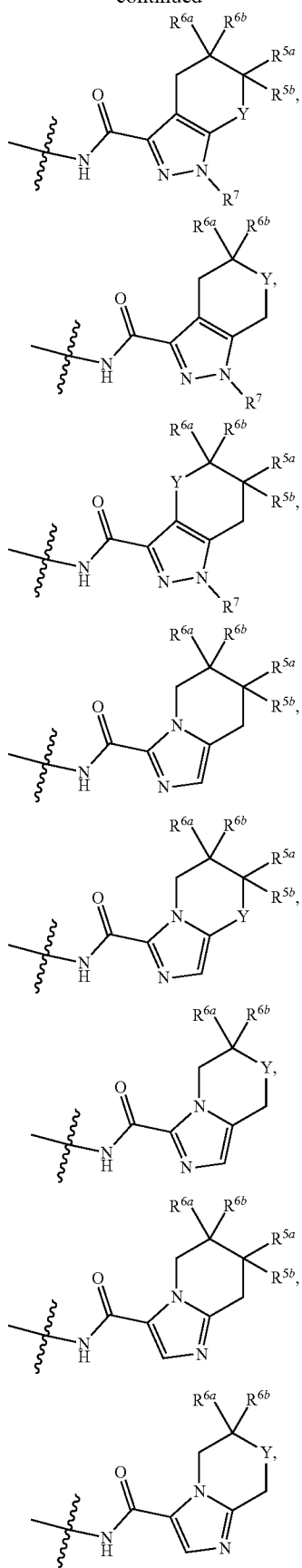

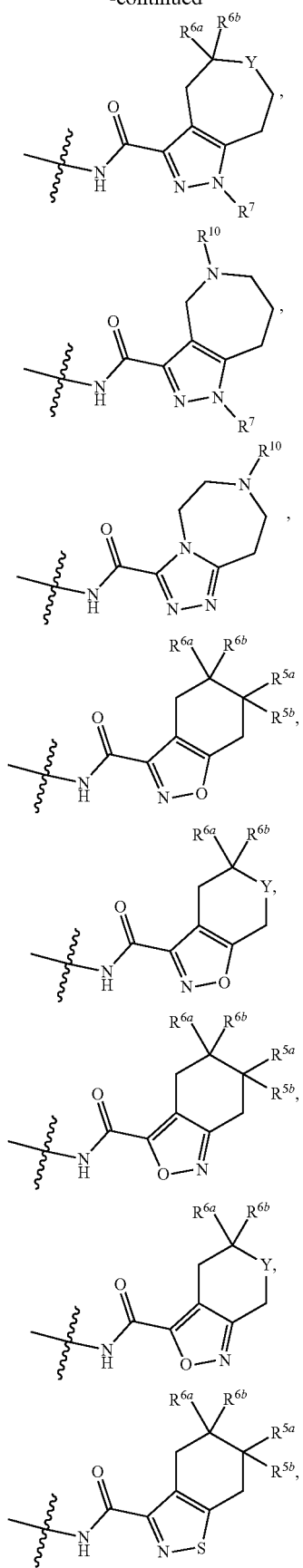
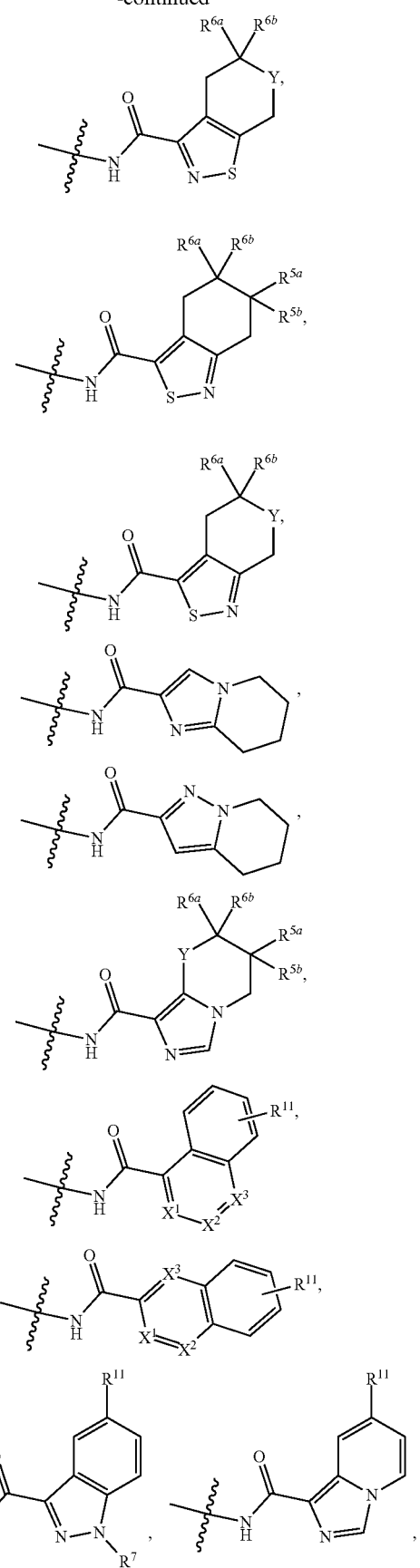

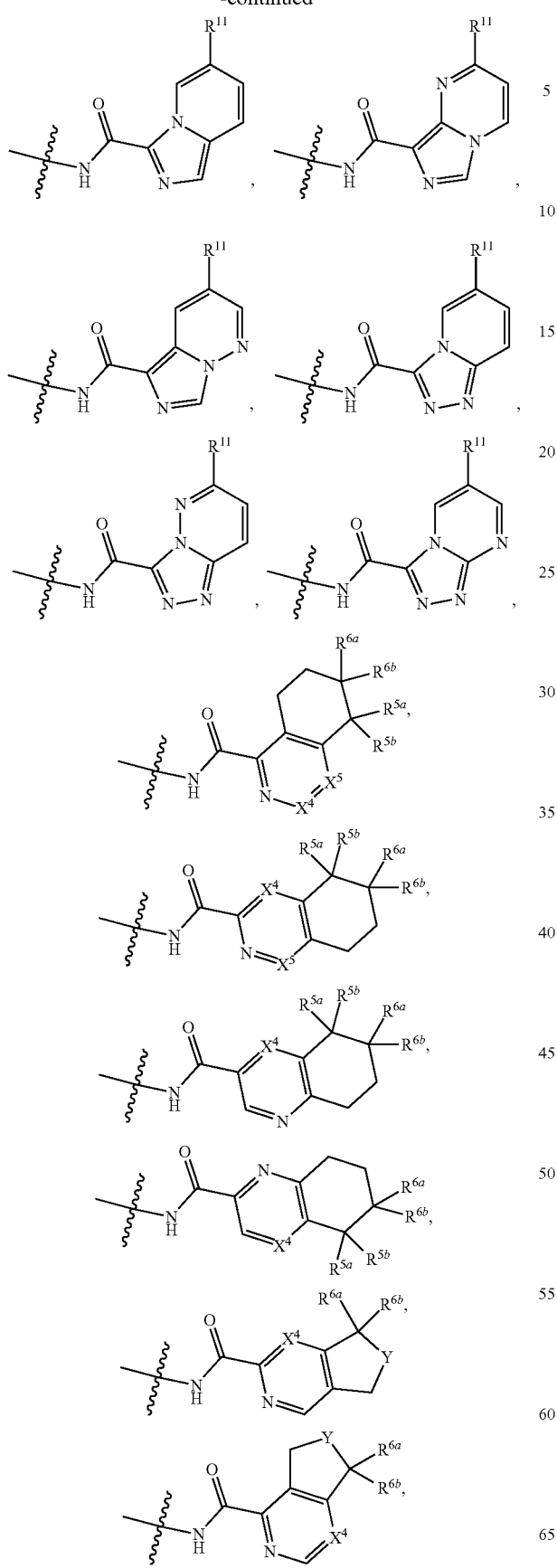
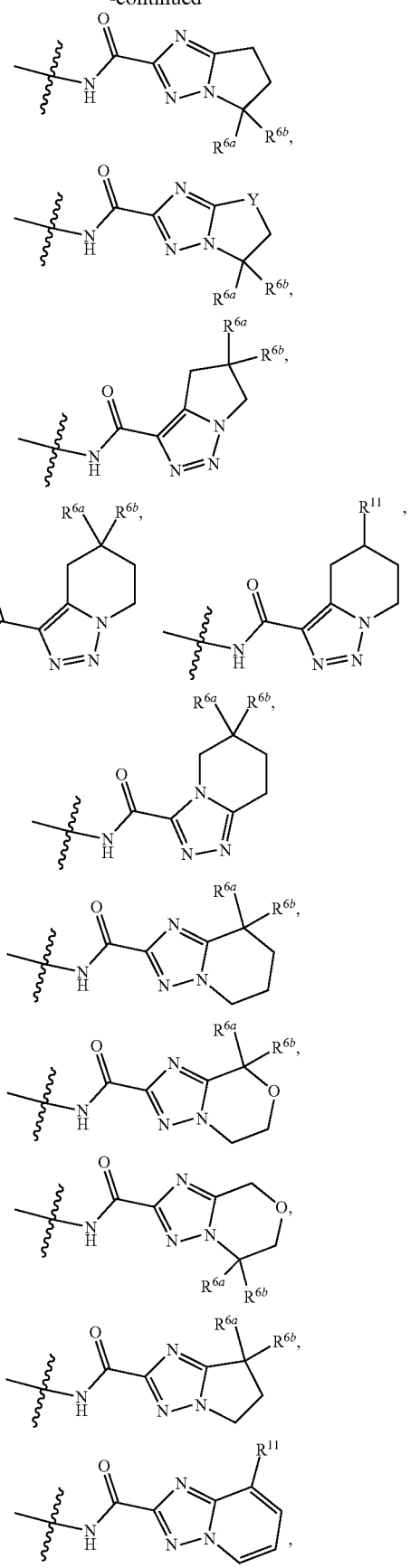

-continued
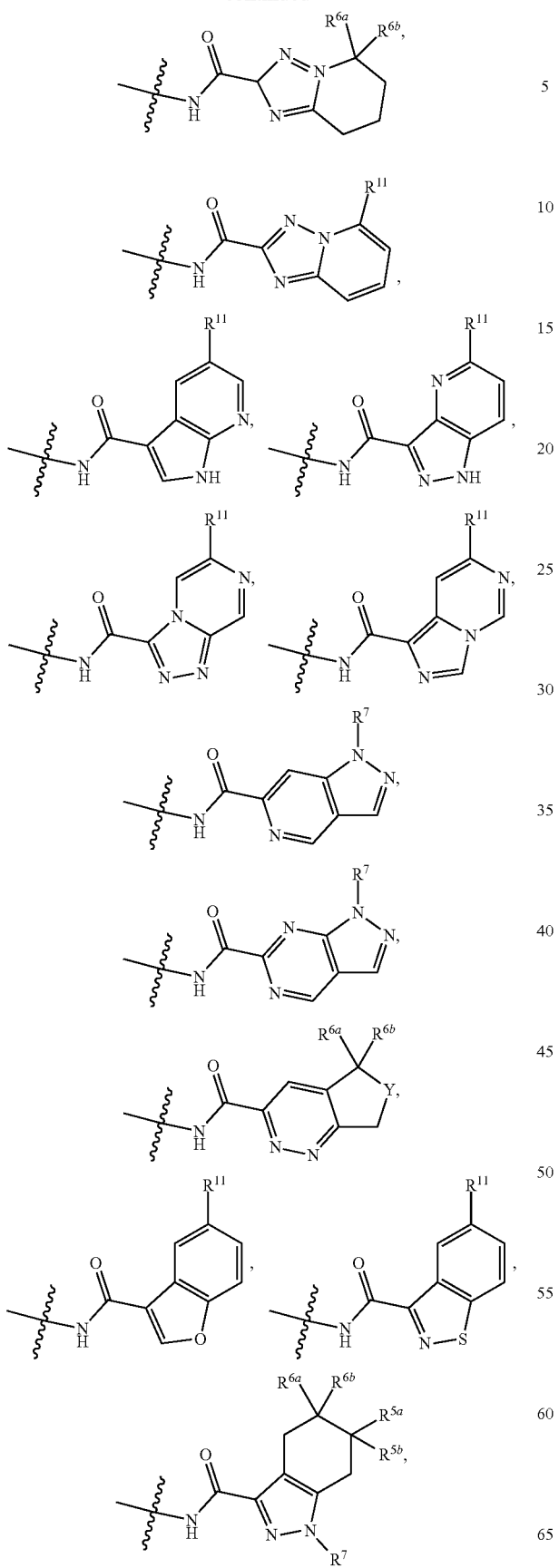
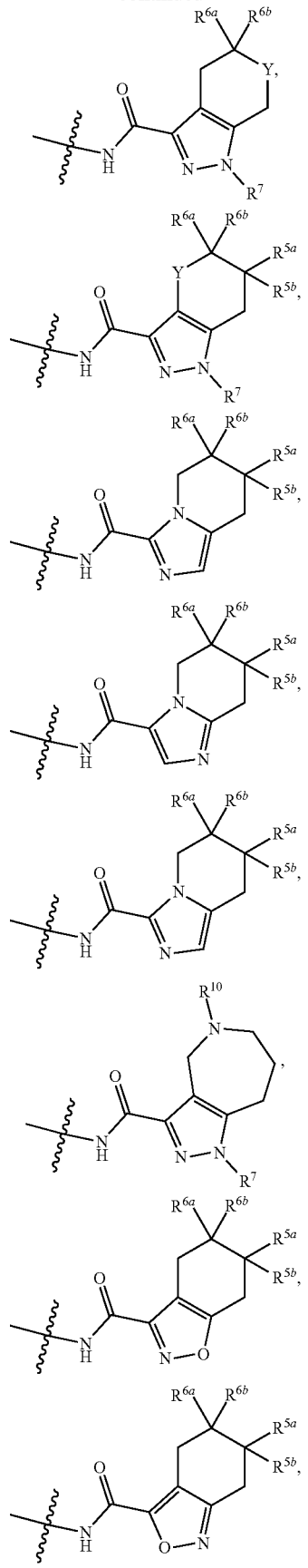

-continued

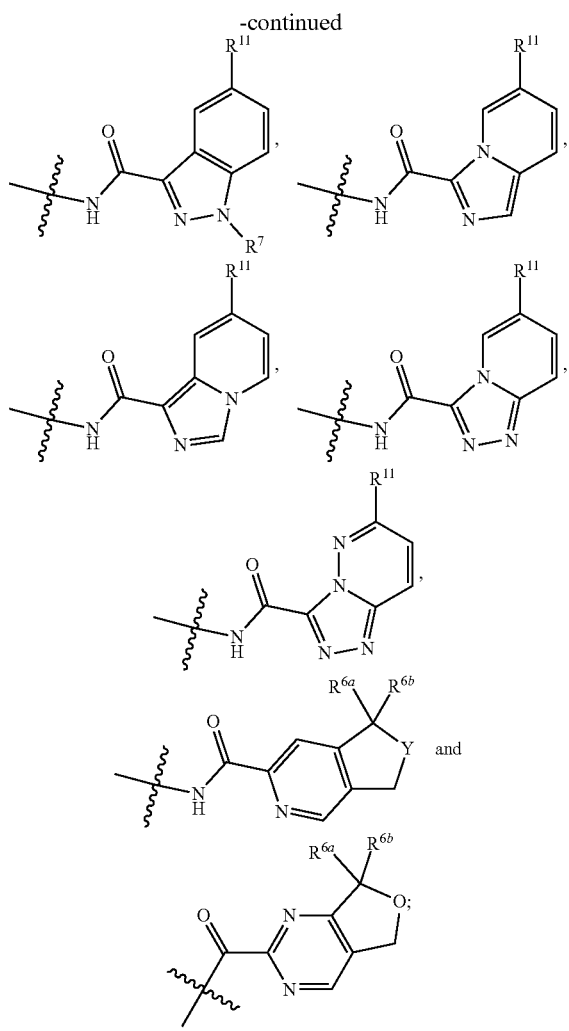

wherein
Y is selected from the group consisting of O, S, SO and SO$_2$;
X$^1$, X$^2$ and X$^3$ are each independently N or CH, wherein 1 or 2 of X$^1$, X$^2$ and X$^3$ is N;
X$^4$ and X$^5$ are each independently N or CH;
R$^{5a}$ and R$^{5b}$, are each independently selected from the group consisting of H, C$_1$-C$_6$ alkyl, C$_3$-C$_6$ cycloalkyl, C$_1$-C$_6$ haloalkyl, C$_1$-C$_6$ alkoxy, C$_1$-C$_6$ haloalkoxy, phenyl, benzyl, —CH$_2$(C$_3$-C$_6$ cycloalkyl); and 5 or 6 membered heteroaryl; wherein R$^{5a}$ and R$^{5b}$ together with the carbon to which they are attached may form a 3 to 5 membered cycloalkyl optionally substituted by one or two fluoro, or a 4 to 5 membered cycloalkoxy;
R$^{6a}$ and R$^{6b}$ are each independently selected from the group consisting of H, C$_1$-C$_6$ alkyl, C$_3$-C$_6$ cycloalkyl, C$_1$-C$_6$ haloalkyl, C$_1$-C$_6$ alkoxy, C$_1$-C$_6$ haloalkoxy, phenyl, halophenyl, benzyl, —CH$_2$(C$_3$-C$_6$ cycloalkyl), and 5 or 6 membered heteroaryl; wherein R$^{6a}$ and R$^{6b}$ together with the carbon to which they are attached may form a 3 to 5 membered cycloalkyl optionally substituted by one or two fluoro, or a 4 to 5 membered cycloalkoxy;
wherein when R$^{5a}$ and R$^{6a}$ are each H, R$^{5b}$ and R$^{6b}$ may together form a 3 or 4 membered cycloalkyl;
and wherein only two of R$^{5a}$, R$^{5b}$, R$^{6a}$ and R$^{6b}$ may be other than H in each instance;

R$^7$ is selected from the group consisting of H, unsubstituted C$_1$-C$_4$ alkyl, C$_3$-C$_6$ cycloalkyl, and C$_4$-C$_6$ cycloalkoxy;
R$^{10}$ is selected from the group consisting of H, C$_1$-C$_6$ alkyl, C$_3$-C$_6$ cycloalkyl, C$_1$-C$_6$ haloalkyl, phenyl, and benzyl; and
R$^{11}$ is selected from the group consisting of H, halogen, cyano, C$_1$-C$_4$ alkyl, and C$_1$-C$_4$ haloalkyl.
In some embodiments, Y is O.
In some embodiments, R$^{5a}$ and R$^{5b}$ are each H.
In some embodiments, R$^{5a}$ and R$^{5b}$ are each H; and R$^{6a}$ and R$^{6b}$ are each independently C$_1$-C$_4$ alkyl. In some embodiments, R$^{5a}$ and R$^{5b}$ are each H; R$^{6a}$ is H; and R$^{6b}$ is C$_1$-C$_4$ alkyl, C$_1$-C$_4$ haloalkyl or phenyl. In some embodiments, R$^{5a}$ and R$^{5b}$ are each H; R$^{6a}$ is H; and R$^{6b}$ is C$_1$-C$_4$ alkyl or C$_1$-C$_4$ haloalkyl. In some embodiments, R$^{5a}$ and R$^{5b}$ are each H; R$^{6a}$ is methyl; and R$^{6b}$ is C$_1$-C$_4$ alkyl or C$_3$-C$_4$ cycloalkyl. In some embodiments, R$^{5a}$ and R$^{5b}$ are each H; R$^{6a}$ is methyl; and R$^{6b}$ is phenyl.
In some embodiments, R$^{5a}$ and R$^{6a}$ are each H, and R$^{5b}$ and R$^{6b}$ together form cyclopropyl or cyclobutyl; and Y is O.
In some embodiments, R$^7$ is H or methyl.
In some embodiments, R$^{10}$ is selected from the group consisting of H, C$_1$-C$_4$ alkyl, C$_3$-C$_4$ cycloalkyl, phenyl, and benzyl.
In some embodiments, R$^{11}$ is selected from the group consisting of H, halogen, methyl, and trifluromethyl.
In some embodiments, provided herein is a compound of formula I, Ia, Ib, Ic or Id, wherein

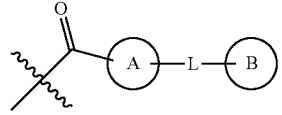

is selected from the group consisting of:

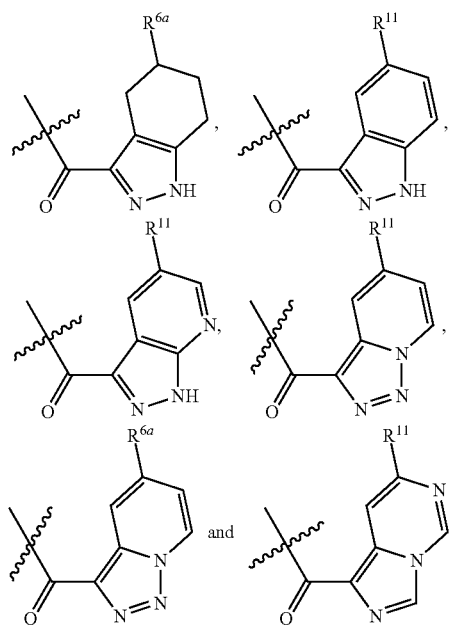

wherein R$^{6a}$ and R$^{11}$ are as defined above. In some embodiments, R$^{6a}$ is C$_1$-C$_6$ alkyl, C$_3$-C$_6$ cycloalkyl, C$_1$-C$_6$ haloalkyl, phenyl or halophenyl. In some embodiments, $R^{11}$ is $C_1$-$C_6$ alkyl, $C_3$-$C_6$ cycloalkyl, $C_1$-$C_6$ haloalkyl or phenyl.

Also provided herein are embodiments corresponding to each of those described above, wherein each substituent is unsubstituted unless explicitly provided in the embodiment.

In another embodiment, provided herein is a compound selected from the compounds of Table 1 below.

In one embodiment, provided herein is a compound selected from the group consisting of:
(S)-1-benzyl-N-(1,5-dimethyl-2,6-dioxo-2,5,6,7,8,9-hexahydro-1H-pyrido[3,2-b]azepin-7-yl)-1H-1,2,4-triazole-3-carboxamide;
(S)—N-(1,5-dimethyl-2,6-dioxo-2,5,6,7,8,9-hexahydro-1H-pyrido[3,2-b]azepin-7-yl)-1-(2-fluorobenzyl)-1H-1,2,4-triazole-3-carboxamide;
1-benzyl-N-[(3S)-1-methyl-2,7-dioxo-4,5-dihydro-3H-pyrido[1,2-a][1,3]diazepin-3-yl]-1,2,4-triazole-3-carboxamide;
1-[(2-fluorophenyl)methyl]-N-[(3S)-1-methyl-2,7-dioxo-4,5-dihydro-3H-pyrido[1,2-a][1,3]diazepin-3-yl]-1,2,4-triazole-3-carboxamide;
1-benzyl-N-[(3S)-1,7-dimethyl-2,8-dioxo-4,5-dihydro-3H-pyrido[4,3-b]azepin-3-yl]-1,2,4-triazole-3-carboxamide;
1-[(2-fluorophenyl)methyl]-N-[(3S)-1,7-dimethyl-2,8-dioxo-4,5-dihydro-3H-pyrido[4,3-b]azepin-3-yl]-1,2,4-triazole-3-carboxamide;
(S)-1-benzyl-N-(1,8-dimethyl-2,7-dioxo-2,3,4,5,7,8-hexahydro-1H-pyrido[3,4-b]azepin-3-yl)-1H-1,2,4-triazole-3-carboxamide;
(S)—N-(1,8-dimethyl-2,7-dioxo-2,3,4,5,7,8-hexahydro-1H-pyrido[3,4-b]azepin-3-yl)-1-(2-fluorobenzyl)-1H-1,2,4-triazole-3-carboxamide;
(S)—N—((S)-1,8-dimethyl-2,7-dioxo-2,3,4,5,7,8-hexahydro-1H-pyrido[3,4-b]azepin-3-yl)-5-(2-fluorophenyl)-6,7-dihydro-5H-pyrrolo[1,2-b][1,2,4]triazole-2-carboxamide; and
(5S)-5-(2-fluorophenyl)-N-[(3S)-1,7-dimethyl-2,8-dioxo-4,5-dihydro-3H-pyrido[4,3-b]azepin-3-yl]-6,7-dihydro-5H-pyrrolo[1,2-b][1,2,4]triazole-2-carboxamide.

Also provided herein is a method for the treatment or prophylaxis of a disease or disorder in a human, the method comprising administration to the human of an effective amount of a compound provided herein, wherein the disease or disorder is selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cisplatin-induced kidney injury, sepsis, systemic inflammatory response syndrome (SIRS), pancreatitis, psoriasis, retinitis pigmentosa, retinal degeneration, chronic kidney diseases, acute respiratory distress syndrome (ARDS), chronic obstructive pulmonary disease (COPD).

Also provided herein is a method for the treatment of a disease or disorder in a human, the method comprising administration to the human of an effective treatment amount of a compound provided herein, wherein the disease or disorder is selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cisplatin-induced kidney injury, sepsis, systemic inflammatory response syndrome (SIRS), pancreatitis, psoriasis, retinitis pigmentosa, retinal degeneration, chronic kidney diseases, acute respiratory distress syndrome (ARDS), chronic obstructive pulmonary disease (COPD).

Pharmaceutical Compositions and Administration

Provided herein are pharmaceutical compositions or medicaments containing the compounds of the invention (or stereoisomers, geometric isomers, tautomers, solvates, metabolites, isotopes, pharmaceutically acceptable salts, or prodrugs thereof), and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. In some embodiments, the "effective amount" of the compound to be administered will be governed by such considerations, and is the minimum amount necessary to inhibit RIP1 kinase activity in order to provide a therapeutic effect in the mammal being treated. In addition, such an effective amount may be below the amount that is toxic to normal cells, or the mammal as a whole.

In one example, the pharmaceutically effective amount of the compound of the invention administered intravenously or parenterally will be in the per dose range of about 0.1 to 100 mg/kg, alternatively about 0.1 to 20 mg/kg of patient body weight per day, or alternatively about 0.3 to 15 mg/kg/day.

In another embodiment, oral unit dosage forms, such as tablets and capsules, preferably contain from about 1 to about 1000 mg (e.g., 1 mg, 5 mg, 10 mg, 15 mg, 20 mg, 25 mg, 30 mg, 40 mg, 50 mg, 100 mg, 200 mg, 250 mg, 400 mg, 500 mg, 600 mg, 700 mg, 800 mg, 900 mg, or 1000 mg) of the compound of the invention. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

In some embodiments, a low dose of the compound of the invention is administered in order to provide therapeutic benefit while minimizing or preventing adverse effects.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration. In specific embodiments, the compound of formula I is administered orally. In other specific embodiments, the compound of formula I is administered intravenously.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of formula I or an embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philidelphia, Pa.

Sustained-release preparations of a compound of the invention (e.g., compound of formula I or an embodiment thereof) can be prepared. Suitable examples of sustained-release preparations include semipermeable matrices of solid hydrophobic polymers containing a compound of formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

In one example, compounds of formula I or an embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I (or an embodiment thereof) is formulated in an acetate buffer, at pH 5. In another embodiment, the compounds of formula I or an embodiment thereof are sterile. The compound may be stored, for example, as a solid or amorphous composition, as a lyophilized formulation or as an aqueous solution.

An example of a suitable oral dosage form provided herein is a tablet containing about 1 to about 500 mg (e.g., about 1 mg, 5 mg, 10 mg, 25 mg, 30 mg, 50 mg, 80 mg, 100 mg, 150 mg, 250 mg, 300 mg and 500 mg) of the compound of the invention compounded with suitable amounts of anhydrous lactose, sodium croscarmellose, polyvinylpyrrolidone (PVP) K30, and magnesium stearate. The powdered ingredients are first mixed together and then mixed with a solution of the PVP. The resulting composition can be dried, granulated, mixed with the magnesium stearate and compressed to tablet form using conventional equipment.

Formulations of a compound of the invention (e.g., compound of formula I or an embodiment thereof) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described.

An embodiment, therefore, includes a pharmaceutical composition comprising a compound of formula I, or pharmaceutically acceptable salt thereof. In a further embodiment includes a pharmaceutical composition comprising a compound of formula I, or a pharmaceutically acceptable salt thereof, together with a pharmaceutically acceptable carrier or excipient.

When the binding target is located in the brain, certain embodiments of the invention provide for a compound of formula I (or an embodiment thereof) to traverse the blood-brain barrier. In these embodiments, the compounds provided herein exhibit sufficient brain penetration as potential therapeutics in neurological diseases. In some embodiments, brain penetration is assessed by evaluating free brain/plasma ratio (B/P) as measured in vivo pharmacokinetic studies in rodents or by other methods known to persons skilled in the art (see, e.g., Liu, X. et al., J. Pharmacol. Exp. Therap., 325:349-56, 2008).

Certain neurological diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods. Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford.

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I (or an embodiment thereof) across the blood-brain barrier include, but are not limited to, encapsulating the a compound of formula I or I-I (or an embodiment thereof) in liposomes that are coupled to antibody binding fragments that bind to receptors on the vascular endothelium of the blood-brain barrier (see, e.g., U.S. Patent Publication No. 2002/0025313), and coating a compound of formula I (or an embodiment thereof) in low-density lipoprotein particles (see, e.g., U.S. Patent Publication No. 2004/0204354) or apolipoprotein E (see, e.g., U.S. Patent Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Publication Nos. 2002/0065259, 2003/0162695, and 2005/0124533); activating potassium channels (see, e.g., U.S. Patent Publication No. 2005/0089473), inhibiting ABC drug transporters (see, e.g., U.S. Patent Publication No. 2003/0073713); coating a compound of formula I or I-I (or an embodiment thereof) with a transferrin and modulating activity of the one or more transferrin receptors (see, e.g., U.S. Patent Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Indications and Methods of Treatment

The compounds of the invention inhibit RIP1 kinase activity. Accordingly, the compounds of the invention are useful for the treatment of diseases and disorders mediated by this pathway and associated with inflammation and/or necroptotic cell death. Compounds of the invention are therefore useful for the treatment or prevention of a disease or disorder selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cysplatin-induced kidney injury, sepsis, systemic inflammatory response syndrome (SIRS), pancreatitis, psoriasis, retinitis pigmentosa, retinal degeneration, chronic kidney diseases, acute respiratory distress syndrome (ARDS), and chronic obstructive pulmonary disease (COPD).

In another embodiment, compounds of the invention are useful for the treatment of one or more symptoms of the above diseases and disorders. In some embodiments, the disease or disorder is an irritable bowel disorder. In some embodiments, the disease or disorder is irritable bowel syndrome (IBS), Crohn's disease, or ulcerative colitis. In some embodiments, the disease or disorder is an ischemia-reperfusion injury of kidneys, liver and lungs. In some embodiments, the disease or disorder is a chronic kidney disease. In some embodiments, the disease or disorder is acute respiratory distress syndrome (ARDS). In some embodiments, the disease or disorder is chronic obstructive pulmonary disease (COPD).

In some embodiments, the disease or disorder to be treated is selected from the group consisting of inflammatory bowel diseases (including Crohn's disease and ulcerative colitis), psoriasis, retinal detachment, retinitis pigmentosa, macular degeneration, pancreatitis, atopic dermatitis, arthritis (including rheumatoid arthritis, osteoarthritis, spondylarthritis, gout, systemic onset juvenile idiopathic arthritis (SoJIA), psoriatic arthritis), systemic lupus erythematosus (SLE), Sjogren's syndrome, systemic scleroderma, anti-phospholipid syndrome (APS), vasculitis, liver damage/diseases (non-alcohol steatohepatitis, alcohol steatohepatitis, autoimmune hepatitis autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury (AKI)), Celiac disease, autoimmune idiopathic thrombocytopenic purpura, transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), spinal muscular atropy (SMA), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), periodontitis, NEMO-deficiency syndrome (F-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2, Gangliosidosis, Alpha-mannosidosis, Aspartylglucosaminuria, Cholesteryl Ester storage disease, Chronic Hexosaminidase A Deficiency, Cystinosis, Danon disease, Fabry disease, Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease).

Also provided herein is the use of a compound of the invention in therapy. In some embodiments, provided herein is the use of a compound of the invention for the treatment or prevention of the above diseases and disorders. Also provided herein is the use of a compound of the invention in the manufacture of a medicament for the treatment or prevention of the above diseases and disorders.

Also provided herein is a method of treating a disease or disorder in a mammal in need of such treatment, said disease or disorder being selected from the group consisting of irritable bowel disorders (IBD), irritable bowel syndrome (IBS), Crohn's disease, ulcerative colitis, myocardial infarction, stroke, traumatic brain injury, atherosclerosis, ischemia reperfusion injury of kidneys, liver and lungs, cysplatin-induced kidney injury, sepsis, systemic inflammatory response syndrome (SIRS), pancreatitis, psoriasis, retinitis pigmentosa, retinal degeneration, chronic kidney diseases, acute respiratory distress syndrome (ARDS), and chronic obstructive pulmonary disease (COPD), wherein the method comprises administering to said mammal a therapeutically effective amount of a compound of formula I, or a pharmaceutically acceptable salt thereof.

Also provided herein is a method of treating a symptom of a disease or disorder in a mammal in need of such treatment, said disease or disorder being selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cysplatin-induced kidney injury, sepsis, systemic inflammatory response syndrome (SIRS), pancreatitis, psoriasis, retinitis pigmentosa, retinal degeneration, chronic kidney diseases, acute respiratory distress syndrome (ARDS), and chronic obstructive pulmonary disease (COPD), wherein the method comprises administering to said mammal a therapeutically effective amount of a compound of formula I, or a pharmaceutically acceptable salt thereof.

Also provided herein is a method of treating a disease or disorder in a mammal in need of such treatment, said disease or disorder being selected from the group consisting of irritable bowel disorders (IBD), irritable bowel syndrome (IBS), Crohn's disease, and ulcerative colitis, wherein the method comprises orally administering to said mammal a therapeutically effective amount of a compound of formula I, or a pharmaceutically acceptable salt thereof, as an orally acceptable pharmaceutical composition.

Combination Therapy

Compounds of the invention may be combined with one or more other compounds of the invention or one or more other therapeutic agent as any combination thereof, in the treatment of the diseases and disorders provided herein. For example, a compound of the invention may be administered simultaneously, sequentially or separately in combination with other therapeutic agents known to be useful for the treatment of a disease or disorder selected from those recited above.

In some embodiments, a compound provided herein may be combined with another therapeutically active agent as recited in WO 2016/027253, the contents of which are hereby incorporated by reference in their entirety. In such embodiments, the compound that inhibits RIP1 kinase in the combinations recited in WO 2016/027253 is replaced by a compound of formula I of the present disclosure.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

EXAMPLES

The invention will be more fully understood by reference to the following examples. They should not, however, be construed as limiting the scope of the invention.

These examples serve to provide guidance to a skilled artisan to prepare and use the compounds, compositions and methods of the invention. While particular embodiment of the present invention are described, the skilled artisan will appreciate that various changes and modifications can be made without departing from the spirit and scope of the inventions.

The chemical reactions in the examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, for example, by appropriately protecting interfering group, by utilizing other suitable reagents known in the art, for example, by appropriately protecting interfering groups by utilizing other suitable reagents known in the art other than those described, and/or by making routine modifications of reaction conditions.

In the examples below, unless otherwise indicated all temperatures are set forth in degrees Celsius. Commercially available reagents were purchased from suppliers such as Aldrich Chemical Company, Lancaster, TCI or Maybridge and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. $^1$H NMR spectra were obtained in deuterated $CDCl_3$, $d_6$-DMSO, $CH_3OD$ or $d_6$-acetone solvent solutions (reported in ppm) using or trimethylsilane (TMS) or residual non-deuterated solvent peaks as the reference standard. When peak multiplicities are reported, the following abbreviates are used: s (singlet), d (doublet), t (triplet), q (quartet), m (multiplet, br (broadened), dd (doublet of doublets), dt (doublet of triplets). Coupling constants, when given, are reported in Hz (Hertz).

In the examples below, LCMS methods were performed for 10 or 30 minutes according to the following conditions:

Agilent 10 min LCMS Method: Experiments performed on an Agilent 1290 UHPLC coupled with Agilent MSD (6140) mass spectrometer using ESI as ionization source. The LC separation was using a Phenomenex XB-C18, 1.7 mm, 50×2.1 mm column with a 0.4 ml/minute flow rate. Solvent A is water with 0.1% FA and solvent B is acetonitrile with 0.1% FA. The gradient consisted with 2-98% solvent B over 7 min and hold 98% B for 1.5 min following equilibration for 1.5 min. LC column temperature is 40° C. UV absorbance was collected at 220 nm and 254 nm and mass spec full scan was applied to all experiment.

Agilent 30 min LCMS Method: Experiments performed on an Agilent 1100 HPLC coupled with Agilent MSD mass spectrometer using ESI as ionization source. The LC separation was using an Agilent Eclipse XDB-C18, 3.5 mm, 100×3.0 mm column with a 0.7 ml/minute flow rate. Solvent A is water with 0.1% FA and solvent B is acetonitrile with 0.1% FA. The gradient consisted with 2-98% solvent B over 25.5 min and hold 98% B for 2.5 min following equilibration for 1.5 min. UV absorbance were collected at 220 nm and 254 nm and mass spec full scan was applied to all experiment.

All abbreviations used to describe reagents, reaction conditions or equipment are intended to be consistent with the definitions set forth in the following list of Abbreviations. The chemical names of discrete compounds of the invention were typically obtained using the structure naming feature of ChemDraw naming program.

Abbreviations
ACN Acetonitrile
Boc tert-Butoxycarbonyl
DMF N,N-Dimethylformamide
DMSO Dimethyl sulfoxide
HPLC High Pressure Liquid Chromatography
LCMS Liquid Chromatography Mass Spectrometry
RP Reverse phase
RT or $R_T$ Retention time
SEM 2-(Trimethylsilyl)ethoxymethyl
THF Tetrahydrofuran

Example 1

Synthetic Method #1

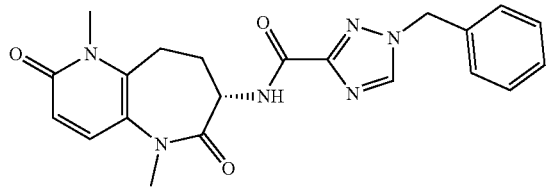

1-benzyl-N-[(7S)-1,5-dimethyl-2,6-dioxo-8,9-di-hydro-7H-pyrido[3,2-b]azepin-7-yl]-1,2,4-triazole-3-carboxamide and 1-benzyl-N-[(7R)-1,5-dimethyl-2,6-dioxo-8,9-dihydro-7H-pyrido[3,2-b]azepin-7-yl]-1,2,4-triazole-3-carboxamide

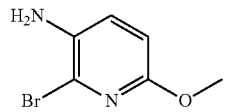

Step 1: 2-bromo-6-methoxy-pyridin-3-amine

To a solution of 2-bromo-6-methoxy-3-nitro-pyridine (15.0 g, 64.37 mmol) in ethanol (100 mL) and water (100 mL) was added iron (18.0 g, 321.86 mmol) and ammonium chloride (17.2 g, 321.86 mmol) under $N_2$ atmosphere. After addition, the mixture was stirred at 60° C. for 5 h and then filtered. The filtrate was diluted with water (200 mL) and extracted with dichloromethane (3×200 mL). The combined organic layers were washed with water (100 mL), brine (100 mL), dried over anhydrous magnesium sulfate and concentrated under reduced pressure. The residue was purified by column chromatography (silica gel, 100-200 mesh, 0 to 10% ethyl acetate in petroleum ether) to give 2-bromo-6-methoxy-pyridin-3-amine (12.0 g, 92%) as a yellow oil. $^1$H NMR (400 MHz, $CDCl_3$) δ 7.04 (d, J=8.4 Hz, 1H), 6.58 (d, J=8.4 Hz, 1H), 3.86 (s, 3H), 3.72 (br. s, 2H).

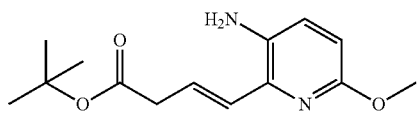 [SMILES: COc1ccc(N)c(/C=C/CC(=O)OC(C)(C)C)n1]

Step 2: tert-butyl (E)-4-(3-amino-6-methoxy-2-pyridyl)but-3-enoate

A mixture of 3-amino-2-bromo-6-methoxy pyridine (4.0 g, 19.7 mmol), tert-butyl 3-butenoate (8.4 g, 59.1 mmol), sodium bicarbonate (5.0 g, 59.1 mmol) dicyclohexyl-[2-(2,4,6-triisopropyl-3-phenyl-phenyl)phenyl]phosphane dichloropalladium (253 mg, 0.2 mmol) in N,N-dimethylformamide (100 mL) was heated at 110° C. for 12 h under $N_2$ atmosphere. After cooling, the mixture was filtered. The filtrate was diluted with water (40 mL) and extracted with ethyl acetate (3×30 mL). The combined organic layers were washed with water (10 mL), brine (10 mL), dried over anhydrous magnesium sulfate and concentrated under reduced pressure. The residue was purified by column chromatography (silica gel, 100-200 mesh, 0 to 10% ethyl acetate in petroleum ether) to give tert-butyl (E)-4-(3-amino-6-methoxy-2-pyridyl)but-3-enoate (2.6 g, 50%) as a yellow oil, used in the next step without further purification.

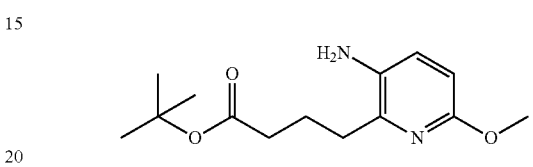

Step 3: tert-butyl 4-(3-amino-6-methoxy-2-pyridyl)butanoate

A mixture of tert-butyl (E)-4-(3-amino-6-methoxy-2-pyridyl)but-3-enoate (2.6 g, 9.84 mmol) and palladium (10% on carbon, 3.1 g, 2.95 mmol) in ethyl acetate (100 mL) was hydrogenated (15 psi) at 25° C. for 2 h. The mixture was filtered and the filtrate was concentrated under reduced pressure to give crude tert-butyl 4-(3-amino-6-methoxy-2-pyridyl)butanoate (2.5 g, 95%) as a yellow oil, used in the next step without further purification.

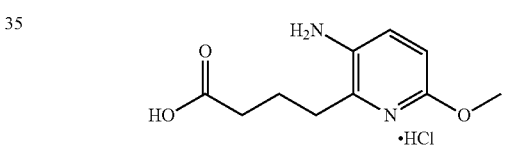

Step 4: 4-(3-amino-6-methoxy-2-pyridyl)butanoic Acid Hydrochloride

To a solution of tert-butyl 4-(3-amino-6-methoxy-2-pyridyl)butanoate (2.5 g, 9.39 mmol) in 1,4-dioxane (20 mL) and water (10 mL) was added HCl (4.0 M in 1,4-dioxane, 20 mL, 80.0 mmol). The mixture was stirred at 25° C. for 12 h and concentrated under reduced pressure to give crude 4-(3-amino-6-methoxy-2-pyridyl)butanoic acid hydrochloride (2.3 g, 99%) as a yellow oil, used in the next step without further purification.

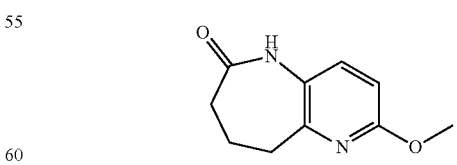

Step 5: 2-methoxy-5,7,8,9-tetrahydropyrido[3,2-b]azepin-6-one

A mixture of 4-(3-amino-6-methoxy-2-pyridyl) butanoic acid hydrochloride (2.3 g, 9.32 mmol), 1-[bis(dimethyl-amino)methylene]-1H-1,2,3-triazolo[4,5-b]pyridinium-3-oxide hexafluorophosphate (5.3 g, 13.99 mmol) and N,N-diisopropylethylamine (3.6 g, 27.97 mmol) in N,N-dimethylformamide (50 mL) was stirred at 25° C. for 3 h. The solvent was removed under reduced pressure and the residue was purified by column chromatography (silica gel, 100-200 mesh, 0 to 50% ethyl acetate in petroleum ether) to give 2-methoxy-5,7,8,9-tetrahydropyrido[3,2-b]azepin-6-one (1.2 g, 67%) as a yellow solid. ¹H NMR (400 MHz, CDCl₃) δ 7.51 (br. s, 1H), 7.20 (d, J=8.4 Hz, 1H), 6.62 (d, J=8.4 Hz, 1H), 3.93 (s, 3H), 2.96-2.93 (m, 2H), 2.40-2.32 (m, 4H).

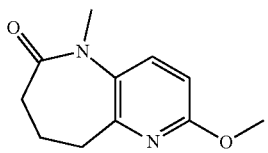

Step 6: 2-methoxy-5-methyl-8,9-dihydro-7H-pyrido[3,2-b]azepin-6-one

To a solution of 2-methoxy-5,7,8,9-tetrahydropyrido[3,2-b]azepin-6-one (1.2 g, 6.24 mmol) in N,N-dimethylformamide (30 mL) was added cesium carbonate (4.1 g, 12.49 mmol) and iodomethane (0.9 g, 6.24 mmol). The mixture was stirred at 25° C. for 2 h and then quenched by addition of water (40 mL). The resulting mixture was extracted with ethyl acetate (3×30 mL). The combined organic layers were washed with water (10 mL), brine (10 mL), dried over anhydrous magnesium sulfate and concentrated under reduced pressure to afford crude 2-methoxy-5-methyl-8,9-dihydro-7H-pyrido[3,2-b]azepin-6-one (1.2 g, 93%) as a yellow solid. Used in the next step without further purification.

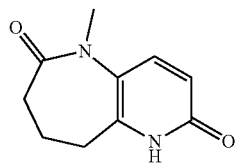

Step 7: 5-methyl-1,7,8,9-tetrahydropyrido[3,2-b]azepine-2,6-dione

To a solution of 2-methoxy-5-methyl-8,9-dihydro-7H-pyrido[3,2-b]azepin-6-one (1.05 g, 5.09 mmol) in acetonitrile (30 mL) was added potassium iodide (1.69 g, 10.18 mmol) and chlorotrimethylsilane (0.79 mL, 10.18 mmol). The mixture was stirred at 60° C. for 3 h, cooled and quenched by addition of water (30 mL). The solution was washed with ethyl acetate (2×10 mL) and concentrated under reduced pressure. The residue was added into a mixture of methanol and dichloromethane (20 mL, 10:1) and stirred for 30 mins. The mixture was filtered and the filtrate was concentrated under reduced pressure to give the crude 5-methyl-1,7,8,9-tetrahydropyrido[3,2-b]azepine-2,6-dione (0.9 g, 92%) as a yellow solid, used in the next step without further purification.

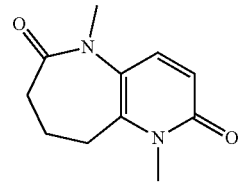

Step 8: 1,5-dimethyl-8,9-dihydro-7H-pyrido[3,2-b]azepine-2,6-dione

A mixture of 5-methyl-1,7,8,9-tetrahydropyrido[3,2-b]azepine-2,6-dione (0.85 g, 4.42 mmol) and cesium carbonate (2.88 g, 8.84 mmol) in N,N-dimethylformamide (20 mL) was added iodomethane (0.75 g, 5.31 mmol). The mixture was stirred at 25° C. for 12 h and then quenched by addition of water (30 mL). The resulting solution was and washed with ethyl acetate (2×10 mL) to remove the regio-isomer (2-methoxy-5-methyl-8,9-dihydro-7H-pyrido[3,2-b]azepin-6-one). The aqueous layer was concentrated under reduced pressure. The residue was added into a mixture of methanol and dichloromethane (30 mL, 10:1) and stirred for 30 min. The mixture was filtered and the filtrate was concentrated under reduced pressure to give the crude 1,5-dimethyl-8,9-dihydro-7H-pyrido[3,2-b]azepine-2,6-dione (900 mg, 98.7%) as a yellow solid. Used in the next step without further purification.

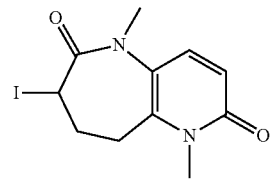 [SMILES: CN1C(=O)C(I)CCc2c1ccc(=O)n2C]

Step 9: 7-iodo-1,5-dimethyl-8,9-dihydro-7H-pyrido[3,2-b]azepine-2,6-dione

To a stirred solution of 1,5-dimethyl-8,9-dihydro-7H-pyrido[3,2-b]azepine-2,6-dione (900 mg, 4.36 mmol) in dichloromethane (100 mL) was added N¹,N¹,N²,N²-tetramethylethane-1,2-diamine (6.08 g, 52.37 mmol) and iodotrimethylsilane (10.50 g, 52.37 mmol) at −15° C. The mixture was stirred at −15° C. for 1.5 h, iodine (6.65 g, 26.18 mmol) was added. The mixture was stirred for another 3 h and then quenched by addition of aqueous sodium thiosulfate (50%, 100 mL). The resulting mixture was extracted with dichloromethane (3×80 mL). The combined organic layers were washed with brine (50 mL), dried over sodium sulfate and concentrated under reduced pressure. The residue was purified by column chromatography (silica gel, 100-200 mesh, 0 to 10% methanol in dichloromethane) to afford 7-iodo-1,5-dimethyl-8,9-dihydro-7H-pyrido[3,2-b]azepine-2,6-dione (850 mg, 59%) as a yellow solid, used as is in the next step.

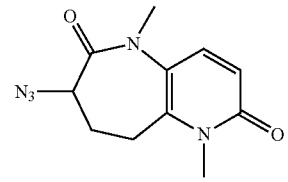 [SMILES: CN1C(=O)C(N=[N+]=[N-])CCc2c1ccc(=O)n2C]

Step 10: 7-azido-1,5-dimethyl-8,9-dihydro-7H-pyrido[3,2-b]azepine-2,6-dione

A mixture of 7-iodo-1,5-dimethyl-8,9-dihydro-7H-pyrido[3,2-b]azepine-2,6-dione (850 mg, 2.56 mmol) and sodium azide (332.7 mg, 5.12 mmol) in N,N-dimethylformamide (15 mL) was stirred at 25° C. for 12 h. The reaction mixture was filtered and the filtrate was concentrated under reduced pressure to give crude 7-azido-1,5-dimethyl-8,9-dihydro-7H-pyrido[3,2-b]azepine-2,6-dione (610 mg, 96%,), used in the next step without further purification. LCMS $R_T$=1.258 min, m/z=248.1 [M+H]$^+$. LCMS (0 to 60% acetonitrile in water+0.05% ammonium hydroxide over 3 mins) retention time 1.258 min, ESI+ found [M+H]=248.1.

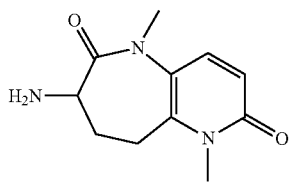 [SMILES: CN1C(=O)C(N)CCc2c1ccc(=O)n2C]

Step 11: 7-amino-1,5-dimethyl-8,9-dihydro-7H-pyrido[3,2-b]azepine-2,6-dione

To a solution of 7-azido-1,5-dimethyl-8,9-dihydro-7H-pyrido[3,2-b]azepine-2,6-dione (610 mg, 2.47 mmol) in tetrahydrofuran (10 mL) and water (2 mL) was added 80% polymer-bound triphenylphosphine (1.94 g). The reaction mixture was stirred at 25° C. for 12 h and filtered. The filtrate was concentrated under reduced pressure to afford 7-amino-1,5-dimethyl-8,9-dihydro-7H-pyrido[3,2-b]azepine-2,6-dione (500 mg 92%) as a yellow oil. LCMS $R_T$=0.988 min, m/z=222.1 [M+H]$^+$. LCMS (0 to 60% acetonitrile in water+0.05% ammonium hydroxide over 3 mins) retention time 0.988 min, ESI+ found [M+H]=222.1.

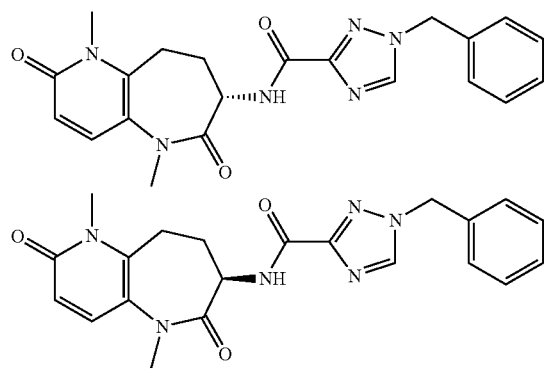

Step 12: 1-benzyl-N-[(7S)-1,5-dimethyl-2,6-dioxo-8,9-dihydro-7H-pyrido[3,2-b]azepin-7-yl]-1,2,4-triazole-3-carboxamide and 1-benzyl-N-[(7R)-1,5-dimethyl-2,6-dioxo-8,9-dihydro-7H-pyrido[3,2-b]azepin-7-yl]-1,2,4-triazole-3-carboxamide A mixture of 7-amino-1,5-dimethyl-8,9-dihydro-7H-pyrido[3,2-b]azepine-2,6-dione (20 mg, 0.09 mmol), 1-(3-dimethylaminopropyl)-3-ethylcarbodiimidehydrochloride (26 mg, 0.14 mmol), 1-hydroxybenzotriazole (18.3 mg, 0.14 mmol) and 1-benzyl-1,2,4-triazole-3-carboxylic acid (22 mg, 0.11 mmol) in N,N-dimethylformamide (1 mL) was stirred at 25° C. for 12 h. The mixture was concentrated under reduced pressure. The residue was purified by RP-HPLC (acetonitrile 20-50%/0.05% ammonium hydroxide in water) to afford the racemic material (30 mg), which was separated by chiral SFC to give arbitrarily assigned:

1-benzyl-N-[(7R)-1,5-dimethyl-2,6-dioxo-8,9-dihydro-7H-pyrido[3,2-b]azepin-7-yl]-1,2,4-triazole-3-carboxamide (Peak 1, retention time 2.38 min) (8.1 mg, 25%) as white solids. $^1$H NMR (400 MHz, CD$_3$OD) δ 8.56 (s, 1H), 7.58 (d, J=10.0 Hz, 1H), 7.36-7.34 (m, 5H), 6.57 (d, J=9.2 Hz, 1H), 5.47 (s, 2H), 4.67-4.62 (m, 1H), 3.68 (s, 3H), 3.29 (s, 3H), 3.06-3.05 (m, 1H), 2.88-2.84 (m, 1H), 2.75-2.72 (m, 1H), 2.27-2.22 (m, 1H). LCMS $R_T$=0.695 min, m/z=407.1 [M+H]$^+$. LCMS (5 to 95% acetonitrile in water+0.03% trifluoacetic acid over 1.5 mins) retention time 0.695 min, ESI+ found [M+H]=407.1.

1-benzyl-N-[(7S)-1,5-dimethyl-2,6-dioxo-8,9-dihydro-7H-pyrido[3,2-b]azepin-7-yl]-1,2,4-triazole-3-carboxamide (Peak 2, retention time 3.639 min) (5.3 mg, 17%) as white solids. $^1$H NMR (400 MHz, CD$_3$OD) δ 8.56 (s, 1H), 7.58 (d, J=9.6 Hz, 1H), 7.37-7.33 (m, 5H), 6.57 (d, J=10.0 Hz, 1H), 5.47 (s, 2H), 4.67-4.62 (m, 1H), 3.68 (s, 3H), 3.29 (s, 3H), 3.10-3.05 (m, 1H), 2.88-2.86 (m, 1H), 2.75-2.72 (m, 1H), 2.27-2.22 (m, 1H). LCMS $R_T$=1.202 min, m/z=407.2 [M+H]$^+$. LCMS (10 to 80% acetonitrile in water+0.05% ammonium hydroxide over 3 mins) retention time 1.202 min, ESI+ found [M+H]=407.2.

SFC condition: Column: Chiralpak AD-3 100×4.6 mm I.D., 3 um Mobile phase: A: CO2 B: methanol (0.05% DEA) Gradient: from 5% to 40% of B in 5 min and hold 40% for 2.5 min, then 5% of B for 2.5 min Flow rate: 2.8 mL/min Column temp.: 40° C.

Example 2

Method #2

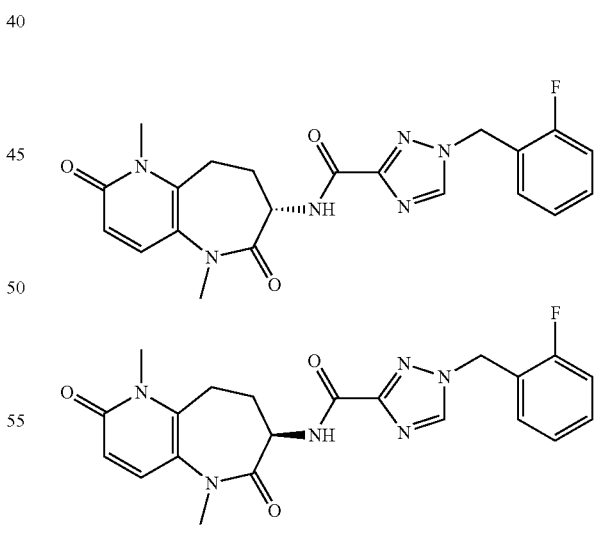

1-[(2-fluorophenyl)methyl]-N-[(7R)-1,5-dimethyl-2,6-dioxo-8,9-dihydro-7H-pyrido[3,2-b]azepin-7-yl]-1,2,4-triazole-3-carboxamide Amide coupling was prepared in a similar fashion to Method #1. The crude was purified by purified by RP-HPLC (acetonitrile 13-43%/0.05% ammonium hydroxide in water) to afford the racemic material (40 mg), which was subsequently separated by chiral SFC to give arbitrarily assigned:

1-[(2-fluorophenyl)methyl]-N-[(7R)-1,5-dimethyl-2,6-dioxo-8,9-dihydro-7H-pyrido[3,2-b]azepin-7-yl]-1,2,4-triazole-3-carboxamide (Peak 1, retention time 2.186 min) (12.6 mg, 31.2%) as white solid. $^1$H NMR (400 MHz, CD$_3$OD) δ 8.58 (s, 1H), 7.58 (d, J=9.6 Hz, 1H), 7.40-7.38 (m, 2H), 7.22-7.15 (m, 2H), 6.57 (d, J=9.6 Hz, 1H), 5.55 (s, 2H), 4.66-4.62 (m, 1H), 3.68 (s, 3H), 3.28 (s, 3H), 3.08-3.04 (m, 1H), 2.88-2.84 (m, 1H), 2.74-2.71 (m, 1H), 2.23-2.22 (m, 1H). LCMS R$_T$=0.702 min, m/z=425.1 [M+H]$^+$. LCMS (5 to 95% acetonitrile in water+0.03% trifluoacetic acid over 1.5 mins) retention time 0.702 min, ESI+ found [M+H]=425.1.

1-[(2-fluorophenyl)methyl]-N-[(7S)-1,5-dimethyl-2,6-dioxo-8,9-dihydro-7H-pyrido[3,2-b]azepin-7-yl]-1,2,4-triazole-3-carboxamide (Peak 2, retention time 3.079 min) (12.3 mg, 30.4%) as white solid. $^1$H NMR (400 MHz, CD$_3$OD) δ 8.58 (s, 1H), 7.58 (d, J=10.0 Hz, 1H), 7.40-7.36 (m, 2H), 7.22-7.15 (m, 2H), 6.57 (d, J=9.6 Hz, 1H), 5.55 (s, 2H), 4.66-4.62 (m, 1H), 3.68 (s, 3H), 3.28 (s, 3H), 3.08-3.04 (m, 1H), 2.88-2.84 (m, 1H), 2.74-2.71 (m, 1H), 2.24-2.21 (m, 1H). LCMS R$_T$=0.710 min, m/z=425.0 [M+H]$^+$. LCMS (5 to 95% acetonitrile in water+0.03% trifluoacetic acid over 1.5 mins) retention time 0.710 min, ESI+ found [M+H]=425.0.

SFC condition: Column: Chiralpak AD-3 100×4.6 mm I.D., 3 um Mobile phase: A: CO2 B: methanol (0.05% DEA) Gradient: from 5% to 40% of B in 5 min and hold 40% for 2.5 min, then 5% of B for 2.5 min Flow rate: 2.8 mL/min Column temp.: 40° C.

Example 3

Method #3

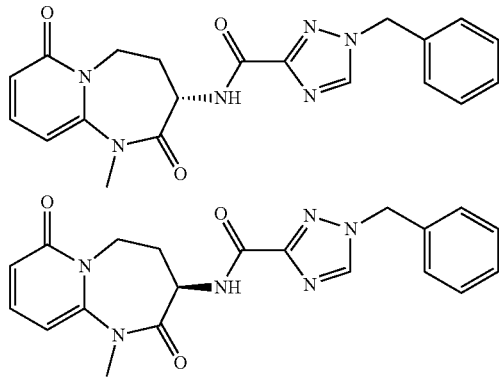

1-benzyl-N-[(3S)-1-methyl-2,7-dioxo-4,5-dihydro-3H-pyrido[1,2-a][1,3]diazepin-3-yl]-1,2,4-triazole-3-carboxamide and 1-benzyl-N-[(3R)-1-methyl-2,7-dioxo-4,5-dihydro-3H-pyrido[1,2-a][1,3]diazepin-3-yl]-1,2,4-triazole-3-carboxamide

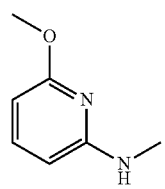

Step 1: 6-methoxy-N-methylpyridin-2-amine

A mixture of 2-chloro-6-methoxypyridine (12.0 g, 85.6 mmol) and aqueous methanamine (40%, 24 mL) was stirred at 170° C. in sealed tube for 7 h. After cooled, the mixture was diluted with water (50 mL) and then extracted with dichloromethane (3×50 mL). The combined organic layers were washed with water (100 mL), brine (100 mL), dried over anhydrous magnesium sulfate and concentrated under reduced pressure. The residue was purified by column chromatography (silica gel, 100-200 mesh, 0 to 5% methanol in dichloromethane) to afford 6-methoxy-N-methylpyridin-2-amine (2.7 g, 31%) as a light yellow oil. $^1$H NMR (400 MHz, CDCl$_3$) δ 7.37 (t, J=8.0 Hz, 1H), 6.04 (d, J=8.0 Hz, 1H), 5.94 (d, J=7.8 Hz, 1H), 4.39 (br. s, 1H), 3.86 (s, 3H), 2.90 (s, 3H).

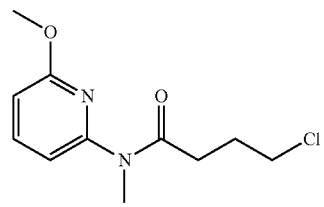 [SMILES: COc1cccc(N(C)C(=O)CCCCl)n1]

Step 2: 4-chloro-N-(6-methoxypyridin-2-yl)-N-methylbutanamide

To a stirred solution of 2-methoxy-6-methylaminopyridine (2.5 g, 18.1 mmol) in dichloromethane (30 mL) was slowly added triethylamine (5.5 g, 54.3 mmol), followed by 4-chlorobutanoyl chloride (3.1 g, 21.7 mmol). After addition, the reaction mixture was stirred at 25° C. for 2 h, and slowly quenched by addition of saturated aqueous sodium bicarbonate (30 mL). The resulting mixture was extracted with dichloromethane (2×50 mL). The combined organic layers were washed with water (100 mL), brine (100 mL), dried over anhydrous magnesium sulfate and concentrated under reduced pressure. The residue was purified by column chromatography (silica gel, 100-200 mesh, 0 to 5% methanol in dichloromethane) to afford the title compound 4-chloro-N-(6-methoxy-2-pyridyl)-N-methyl-butanamide (3.1 g, 71%) as a yellow oil. LCMS R$_T$=0.696 min, m/z=242.8 [M+H]$^+$. LCMS (5 to 95% acetonitrile in water+0.03% trifluoroacetic acid over 1.5 mins) retention time 0.696 min, ESI+ found [M+H]=242.8.

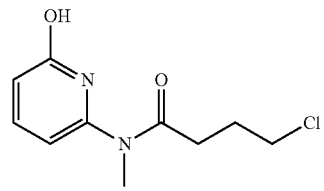

Step 3: 4-chloro-N-(6-hydroxypyridin-2-yl)-N-methylbutanamide

To a suspension of 4-chloro-n-(6-methoxy-2-pyridyl)-n-methyl-butanamide (2.4 g, 9.9 mmol) and potassium iodide (4.9 g, 29.7 mmol) in acetonitrile (30 mL) was slowly added chlorotrimethylsilane (3.2 g, 29.7 mmol) at 25° C. After addition, the mixture was heated at 80° C. for 2 h and then slowly quenched by addition of saturated aqueous sodium bicarbonate (30 mL). The resulting mixture was extracted with dichloromethane (2×50 mL). The combined organic layers were washed with water (100 mL), brine (100 mL), dried over anhydrous magnesium sulfate and concentrated under reduced pressure. The residue was purified by column chromatography (silica gel, 100-200 mesh, 0 to 5% methanol in dichloromethane) to afford 4-chloro-N-(6-hydroxy-2-pyridyl)-N-methyl-butanamide (1.8 g, 80%) as a yellow oil. LCMS $R_T$=1.356 min, m/z=229.1 [M+H]$^+$. LCMS (0 to 60% acetonitrile in water+0.03% trifluoroacetic acid over 3.0 mins) retention time 1.356 min, ESI+ found [M+H]=229.1.

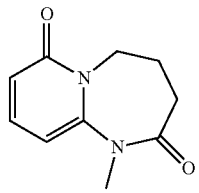

Step 4: 1-methyl-4,5-dihydropyrido[1,2-a][1,3]diaz-epine-2,7(1H,3H)-dione

To a solution of 4-chloro-N-(6-hydroxy-2-pyridyl)-N-methyl-butanamide (1.6 g, 7.0 mmol) in N,N-dimethylformamide (20 mL) was added cesium carbonate (4.6 g, 14.2 mmol). The mixture was stirred at 25° C. for 12 h and then filtered. The filtrate was concentrated to dryness under reduce pressure. The residue was purified by column chromatography (silica gel, 100-200 mesh, 0 to 5% methanol in dichloromethane) to afford 1-methyl-4,5-dihydro-3H-pyrido[1,2-a][1,3]diazepine-2,7-dione (0.9 g, 59%) as a yellow solid. $^1$H NMR (400 MHz, DMSO-d$_6$) δ 7.47 (dd, J=7.6, 8.8 Hz, 1H), 6.31 (d, J=9.2 Hz, 1H), 6.26 (d, J=8.4 Hz, 1H), 4.79 (br. s, 1H), 3.33-3.30 (m, 1H), 3.21 (s, 3H), 2.30-2.27 (m, 2H), 2.03-2.01 (m, 2H). LCMS $R_T$=1.171 min, m/z=193.0 [M+H]+. LCMS (0 to 60% acetonitrile in water+0.03% trifluoroacetic acid over 3.0 mins) retention time 1.171 min, ESI+ found [M+H]=193.0.

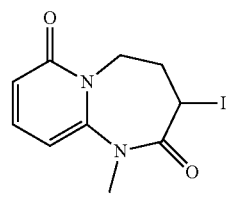

Step 5: 3-iodo-1-methyl-4,5-dihydropyrido[1,2-a][1,3]diazepine-2,7(1H,3H)-dione

To a solution of 1-methyl-4,5-dihydro-3H-pyrido[1,2-a][1,3]diazepine-2,7-dione (550 mg, 2.9 mmol) in dichloromethane (20 mL) was treated with N$^1$,N$^1$,N$^2$,N$^2$-tetramethylethane-1,2-diamine (3.3 g, 28.6 mmol) at −15° C. under nitrogen atmosphere, followed by addition iodotrimethylsilane (4 mL). The reaction mixture was stirred at −15° C. for 1.5 h and to subsequently iodine (2.2 g, 8.6 mmol) was added. The reaction mixture was stirred at 35° C. for 6 h, and slowly quenched by addition of aqueous saturated sodium thiosulfate (50 mL). The resulting mixture was filtered and the filtrate was extracted with dichloromethane (2×50 mL). The combined organic layers were washed with water (50 mL), brine (50 mL) and dried with anhydrous magnesium sulfate and concentrated under reduced pressure. The residue was purified by column chromatography (silica gel, 100-200 mesh, 0 to 5% methanol in dichloromethane) to afford 3-iodo-1-methyl-4,5-dihydro-3H-pyrido[1,2-a][1,3]diazepine-2,7-dione (310 mg, 34%) as a light yellow oil, used as is in the next step.

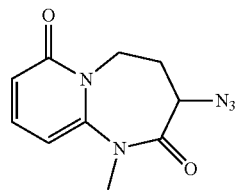 [SMILES: CN1C(=O)C(N=[N+]=[N-])CCn2c1cccc2=O]

Step 6: 3-azido-1-methyl-4,5-dihydropyrido[1,2-a][1,3]diazepine-2,7(1H,3H)-dione A mixture of 3-iodo-1-methyl-4,5-dihydro-3H-pyrido[1,2-a][1,3]diazepine-2,7-dione (310 mg, 1.0 mmol) and sodium azide (276 mg, 4.3 mmol) in N,N-dimethylformamide (10 mL) was stirred at 25° C. for 12 h. The reaction mixture was quenched by addition of 10% aqueous sodium hydroxide (15 mL) solution and extracted with ethyl acetate (3×30 mL). The combined organic layers were washed with brine (2×20 mL) and concentrated under reduced pressure to afford crude 3-azido-1-methyl-4,5-dihydro-3H-pyrido[1,2-a][1,3]diazepine-2,7-dione (200 mg, 88%) as a yellow oil. LCMS $R_T$=1.23 min, m/z=234.2 [M+H]$^1$. LCMS (0 to 60% acetonitrile in water+0.03% trifluoroacetic acid over 3.0 mins) retention time 1.23 min, ESI+ found [M+H]=234.2.

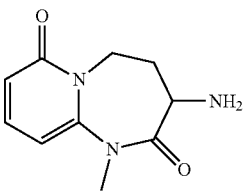

Step 7: 3-amino-1-methyl-4,5-dihydropyrido[1,2-a][1,3]diazepine-2,7(1H,3H)-dione To a solution of 3-azido-1-methyl-4,5-dihydro-3H-pyrido[1,2-a][1,3]diazepine-2,7-dione (200 mg, 0.9 mmol) in tetrahydrofuran (10 mL) and water (2 mL) was added 80% polymer-bound triphenylphosphine (1.27 g, 4.8 mmol). The reaction mixture was stirred at 25° C. for 12 h and then filtered. The filtrate was concentrated under reduced pressure to afford crude 3-amino-1-methyl-4,5-dihydro-3H-pyrido[1,2-a][1,3]diazepine-2,7-dione (160 mg, 90%) as a light yellow oil, used as is in the next step.

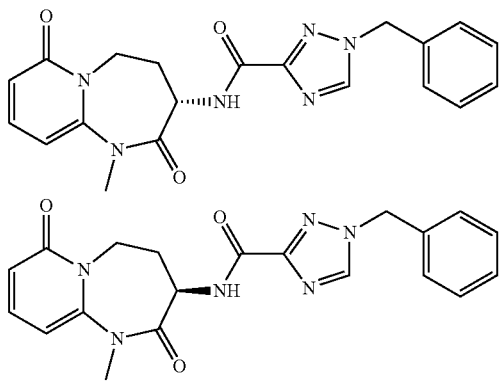

Step 8: 1-benzyl-N-[(3S)-1-methyl-2,7-dioxo-4,5-dihydro-3H-pyrido[1,2-a][1,3]diazepin-3-yl]-1,2,4-triazole-3-carboxamide and 1-benzyl-N-[(3R)-1-methyl-2,7-dioxo-4,5-dihydro-3H-pyrido[1,2-a][1,3]diazepin-3-yl]-1,2,4-triazole-3-carboxamide A mixture of 1-benzyl-1H-1,2,4-triazole-3-carboxylic acid (32 mg, 0.16 mmol), 1-(3-dimethylaminopropyl)-3-ethylcarbodiimidehydrochloride (28 mg, 0.14 mmol), 3-amino-1-methyl-4,5-dihydro-3h-pyrido[1,2-a][1,3]diazepine-2,7-dione (25 mg, 0.12 mmol) and 1-hydroxybenzotriazole (20 mg, 0.14 mmol) in N,N-dimethylformamide (3 mL) was stirred at 25° C. for 12 h. The mixture was concentrated to dryness under reduce pressure. The resulting residue was purified by reverse phase chromatography (acetonitrile 10-40%/0.05% ammonia hydroxide in water) to afford 1-benzyl-N-(1-methyl-2,7-dioxo-1,2,3,4,5,7-hexahydropyrido[1,2-a][1,3]diazepin-3-yl)-1H-1,2,4-triazole-3-carboxamide (30 mg, 63%) as a white solid. The racemic material was further purified by SFC to give arbitrarily assigned:

1-benzyl-N-[(3S)-1-methyl-2,7-dioxo-4,5-dihydro-3H-pyrido[1,2-a][1,3]diazepin-3-yl]-1,2,4-triazole-3-carboxamide (Peak 1, retention time=5.180 min) (12 mg, 40%) as white solids. $^1$H NMR (400 MHz, CD$_3$OD) δ 8.57 (s, 1H), 7.64-7.56 (m, 1H), 7.47-7.25 (m, 5H), 6.53 (d, J=9.2 Hz, 1H), 6.46 (d, J=7.2 Hz, 1H), 5.47 (s, 2H), 5.07-5.03 (m, 1H), 4.61-4.55 (m, 1H), 3.71-3.63 (m, 1H), 3.39 (s, 3H), 2.68-2.60 (m, 1H), 2.19-2.12 (m, 1H). LC-MS R$_T$=1.177 min, m/z=393.2 [M+H]$^+$. LCMS (10 to 80% acetonitrile in water+0.03% ammonium bicarbonate over 3.0 mins) retention time 1.177 min, ESI+ found [M+H]=393.2.

1-benzyl-N-[(3R)-1-methyl-2,7-dioxo-4,5-dihydro-3H-pyrido[1,2-a][1,3]diazepin-3-yl]-1,2,4-triazole-3-carboxamide. (Peak 2, retention time=6.616 min) (8 mg, 26%) as white solids. $^1$H NMR (400 MHz, CD$_3$OD) δ 8.56 (s, 1H), 7.63-7.57 (m, 1H), 7.43-7.25 (m, 5H), 6.52 (d, J=9.2 Hz, 1H), 6.45 (d, J=7.2 Hz, 1H), 5.47 (s, 2H), 5.06-5.01 (m, 1H), 4.59-4.56 (m, 1H), 3.69-3.62 (m, 1H), 3.39 (s, 3H), 2.68-2.60 (m, 1H), 2.19-2.12 (m, 1H). LC-MS R$_T$=1.179 min, m/z=393.1 [M+H]$^+$. LCMS (10 to 80% acetonitrile in water+0.03% ammonium bicarbonate over 3.0 mins) retention time 1.179 min, ESI+ found [M+H]=393.1.

SFC condition: column: chiralcel OD-3 100×4.6 mm I.D., 3 um mobile phase: A: CO$_2$; B: ethanol (0.05% DEA) gradient: hold 5% for 1.0 min, then from 5% to 40% of B in 4.5 min and hold 40% for 2.5 min, then 5% of B for 1.0 min. Flow rate: 2.8 mL/min. Column temperature: 40° C.

Example 4

Method #4

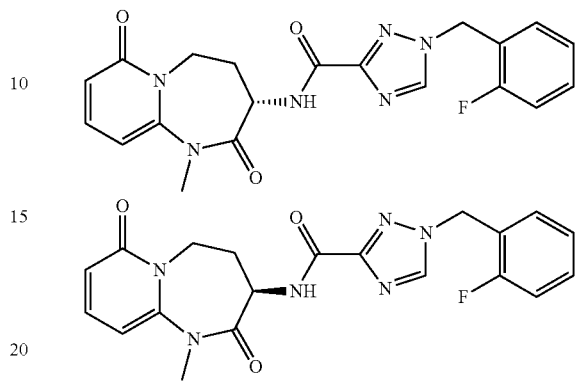

1-[(2-fluorophenyl)methyl]-N-[(3S)-1-methyl-2,7-dioxo-4,5-dihydro-3H-pyrido[1,2-a][1,3]diazepin-3-yl]-1,2,4-triazole-3-carboxamide Amide coupling was prepared in a similar fashion to Method #3. The crude was purified by purified by RP-HPLC (acetonitrile 10-40%/0.05% ammonia hydroxide in water) 1-[(2-fluorophenyl)methyl]-N-(1-methyl-2,7-dioxo-1,2,3,4,5,7-hexahydropyrido[1,2-a][1,3]diazepin-3-yl)-1H-1,2,4-triazole-3-carboxamide (40 mg, 51%) as a white solid. The racemic material was further purified by SFC to give arbitrarily assigned:

1-[(2-fluorophenyl)methyl]-N-[(3S)-1-methyl-2,7-dioxo-4,5-dihydro-3H-pyrido[1,2-a][1,3]diazepin-3-yl]-1,2,4-triazole-3-carboxamide (Peak 1, retention time=4.710 min) (14 mg, 35%) as a white solid. $^1$H NMR (400 MHz, CD$_3$OD) δ 8.58 (s, 1H), 7.62-7.57 (m, 1H), 7.44-7.34 (m, 2H), 7.22-7.12 (m, 2H), 6.52 (d, J=9.2 Hz, 1H), 6.45 (d, J=7.6 Hz, 1H), 5.55 (s, 2H), 5.06-5.01 (m, 1H), 4.60-4.55 (m, 1H), 3.69-3.62 (m, 1H), 3.39 (s, 3H), 2.67-2.59 (m, 1H), 2.19-2.11 (m, 1H). LC-MS R$_T$=1.201 min, m/z=411.1 [M+H]$^+$. LCMS (10 to 80% acetonitrile in water+0.03% ammonium bicarbonate over 3.0 mins) retention time 1.201 min, ESI+ found [M+H]=411.1.

1-[(2-fluorophenyl)methyl]-N-[(3R)-1-methyl-2,7-dioxo-4,5-dihydro-3H-pyrido[1,2-a][1,3]diazepin-3-yl]-1,2,4-triazole-3-carboxamide (Peak 2, retention time=5.765 min) (11 mg, 27%) as a white solid. $^1$H NMR (400 MHz, CD$_3$OD) δ 8.57 (s, 1H), 7.62-7.57 (m, 1H), 7.44-7.34 (m, 2H), 7.22-7.12 (m, 2H), 6.52 (d, J=8.4 Hz, 1H), 6.45 (d, J=6.8 Hz, 1H), 5.55 (s, 2H), 5.06-5.01 (m, 1H), 4.60-4.55 (m, 1H), 3.69-3.62 (m, 1H), 3.38 (s, 3H), 2.67-2.60 (m, 1H), 2.19-2.11 (m, 1H). LC-MS R$_T$=1.201 min, m/z=411.1 [M+H]$^+$. LCMS (10 to 80% acetonitrile in water+0.03% ammonium bicarbonate over 3.0 mins) retention time 1.201 min, ESI+ found [M+H]= 411.1.

SFC (Column: Chiralcel AD-3 100×4.6 mm I.D., 3 um Mobile phase: A: CO$_2$ B: ethanol (0.05% diethyl acetate), Gradient: from 5% to 40% of B in 4.5 min and hold 40% for 2.5 min, then 5% of B for 1 min, Flow rate: 2.8 mL/min Column temperature: 40° C.

Example 5

Method #5

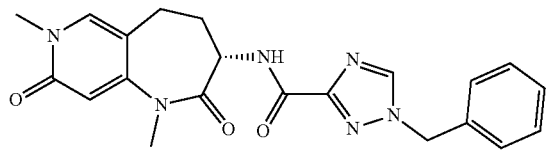 [SMILES: CN1C(=O)[C@@H](NC(=O)c2ncn(Cc3ccccc3)n2)CCc2cn(C)c(=O)cc21]

1-benzyl-N-[(3S)-1,7-dimethyl-2,8-dioxo-4,5-dihydro-3H-pyrido[4,3-b]azepin-3-yl]-1,2,4-triazole-3-carboxamide

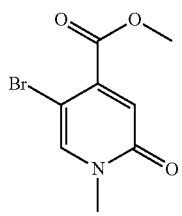

Step 1: methyl 5-bromo-1-methyl-2-oxo-1,2-dihydropyridine-4-carboxylate

To a solution of methyl 5-bromo-2-hydroxy-pyridine-4-carboxylate (2.32 g, 10.00 mmol) in N,N-dimethylformamide (50 mL) was added iodomethane (2.13 g, 15.00 mmol) and cesium carbonate (6.52 g, 20.00 mmol). The reaction mixture was stirred at 25° C. for 6 h and diluted with water (50 mL). The mixture was extracted with ethyl acetate (3×50 mL). The combined organic layers were washed with water (30 mL), brine (30 mL), dried over anhydrous magnesium sulfate and concentrated under reduced pressure to afford crude methyl 5-bromo-1-methyl-2-oxo-pyridine-4-carboxylate (2.30 g, 94%) as a yellow solid, used in the next step without further purification. $^1$H NMR (400 MHz, CD$_3$OD) δ 8.04 (s, 1H), 6.81 (s, 1H), 3.91 (s, 3H), 3.56 (s, 3H).

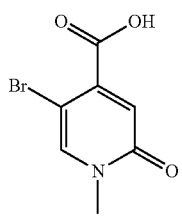

Step 2: 5-bromo-1-methyl-2-oxo-pyridine-4-carboxylic Acid

To a solution of methyl 5-bromo-1-methyl-2-oxo-pyridine-4-carboxylate (2.30 g, 9.35 mmol) in tetrahydrofuran (20 mL)/water (20 mL) was added lithium hydroxide monohydrate (1.96 g, 46.74 mmol). The reaction mixture was stirred at 25° C. for 3 h and then concentrated under reduced pressure. The residue was adjusted to pH=5 by addition of hydrochloric acid (3 M, 10 mL). The solid product was collected by filtration and dried under reduced pressure to afford crude 5-bromo-1-methyl-2-oxo-pyridine-4-carboxylic acid (2.00 g, 92%) as yellow solids. Used in the next step without further purification

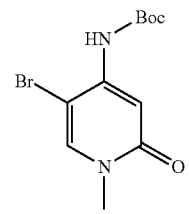

Step 3: tert-butyl N-(5-bromo-1-methyl-2-oxo-4-pyridyl)carbamate

To a solution of 5-bromo-1-methyl-2-oxo-pyridine-4-carboxylic acid (2.00 g, 8.62 mmol) in tert-Butanol (50 mL) was added triethylamine (1.31 g, 12.93 mmol) and diphenylphosphoryl azide (2.85 g, 10.34 mmol). The reaction mixture was heated at 80° C. for 16 h and then concentrated under reduced pressure. The residue was purified by column chromatography (silica gel, 100-200 mesh, 0 to 80% ethyl acetate in petroleum ether) to afford tert-butyl N-(5-bromo-1-methyl-2-oxo-4-pyridyl) carbamate (2.00 g, 77%) as yellow solids.

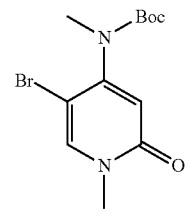

Step 4: tert-butyl N-(5-bromo-1-methyl-2-oxo-4-pyridyl)-N-methyl-carbamate

To a solution of tert-butyl N-(5-bromo-1-methyl-2-oxo-4-pyridyl)carbamate (1.60 g, 5.28 mmol) in N,N-dimethylformamide (30 mL) was added cesium carbonate (3.44 g, 10.56 mmol) and iodomethane (2.11 g, 14.87 mmol). The reaction mixture was stirred at 25° C. for 2 h and then diluted with water (30 mL). The mixture was extracted with ethyl acetate (3×40 mL). The combined organic layers were washed with water (30 mL), brine (30 mL), dried over anhydrous magnesium sulfate and concentrated under reduced pressure to afford crude tert-butyl N-(5-bromo-1-methyl-2-oxo-4-pyridyl)-N-methyl-carbamate (1.30 g, 78%) as yellow oil, used as is in the next step.

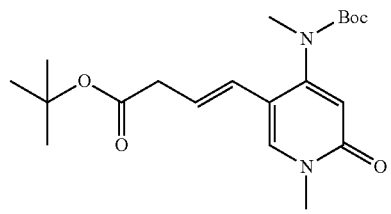 [SMILES: CN(C(=O)OC(C)(C)C)c1cc(=O)n(C)cc1/C=C/CC(=O)OC(C)(C)C]

Step 5: tert-butyl (E)-4-[4-[tert-butoxycarbonyl (methyl)amino]-1-methyl-6-oxo-3-pyridyl]but-3-enoate A mixture of tert-butyl N-(5-bromo-1-methyl-2-oxo-4-pyridyl)-N-methyl-carbamate (1.30 g, 4.10 mmol), sodium bicarbonate (1.03 g, 12.30 mmol), tert-butyl but-3-enoate (1.75 g, 12.30 mmol) and dicyclohexyl-[2-(2,4,6-triisopropyl-3-phenyl-phenyl)phenyl]phosphane dichloropalladium (263 mg, 0.20 mmol) in N,N-dimethylformamide (20 mL) was heated at 110° C. for 12 h under nitrogen. After cooling, the mixture was diluted water (40 mL) and extracted with ethyl acetate (3×30 mL). The combined organic layers were washed with water (30 mL), brine (30 mL), dried over anhydrous magnesium sulfate and concentrated under reduced pressure. The residue was purified by column chromatography (silica gel, 100-200 mesh, 0 to 20% ethyl acetate in petroleum ether) to afford tert-butyl (E)-4-[4-[tert-butoxycarbonyl(methyl)amino]-1-methyl-6-oxo-3-pyridyl]but-3-enoate (1.00 g, 65%) as yellow oil, used as in the next step without further purification.

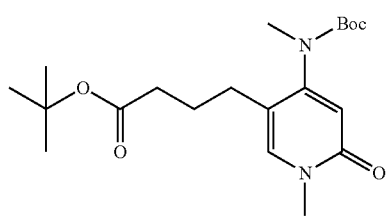 [SMILES: CN(C(=O)OC(C)(C)C)c1cc(=O)n(C)cc1CCCC(=O)OC(C)(C)C]

Step 6: tert-butyl 4-[4-[tert-butoxycarbonyl(methyl) amino]-1-methyl-6-oxo-3-pyridyl]butanoate A mixture of tert-butyl (E)-4-[4-[tert-butoxycarbonyl (methyl)amino]-1-methyl-6-oxo-3-pyridyl]but-3-enoate (1.00 g, 2.64 mmol) and palladium (10% on carbon, 562 mg, 0.53 mmol) in ethyl acetate (50 mL) was hydrogenated (15 psi) at 25° C. for 2 h and subsequently filtered. The filtrate was concentrated under reduced pressure to afford crude tert-butyl 4-[4-[tert-butoxycarbonyl(methyl)amino]-1-methyl-6-oxo-3-pyridyl]butanoate (1.00 g, 100%) as yellow oil.

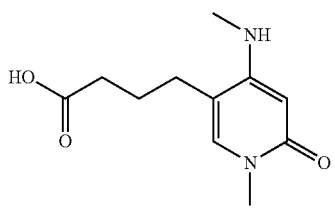 [SMILES: CNc1cc(=O)n(C)cc1CCCC(=O)O]

Step 7: 4-[1-methyl-4-(methylamino)-6-oxo-3-pyridyl]butanoic Acid

To a solution of tert-butyl 4-[4-[tert-butoxycarbonyl (methyl)amino]-1-methyl-6-oxo-3-pyridyl]butanoate (1.00 g, 2.63 mmol) in 1,4-dioxane (20 mL) was added hydrochloric acid (4.0 N in dioxane, 30 mL, 120.0 mmol). The reaction mixture was stirred at 25° C. for 2 h and concentrated under reduced pressure to afford crude 4-[1-methyl-4-(methylamino)-6-oxo-3-pyridyl]butanoic acid (550 mg, 93%) as a yellow oil, use in the next step without further purification.

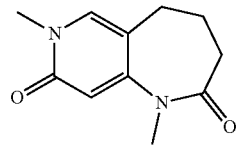

Step 8: 1,7-dimethyl-4,5-dihydro-3H-pyrido[4,3-b] azepine-2,8-dione

A mixture of 1-(3-dimethylaminopropyl)-3-ethylcarbodiimidehydrochloride (705 mg, 3.68 mmol) and 4-[1-methyl-4-(methylamino)-6-oxo-3-pyridyl]butanoic acid (550 mg, 2.45 mmol) in N,N-dimethylformamide (20 mL) was stirred at 25° C. for 2 h and concentrated under reduced pressure. The residue was purified by column chromatography (silica gel, 100-200 mesh, 0 to 5% methanol in dichloromethane) to afford 1,7-dimethyl-4,5-dihydro-3H-pyrido[4,3-b]azepine-2,8-dione (200 mg, 40%) as white solids, used in the next step without further purification.

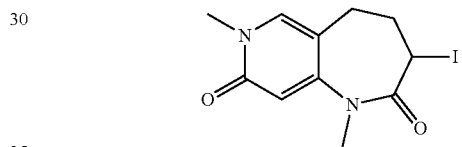

Step 9: 3-iodo-1,7-dimethyl-4,5-dihydro-3H-pyrido [4,3-b]azepine-2,8-dione

To a solution of 1,7-dimethyl-4,5-dihydro-3H-pyrido[4, 3-b]azepine-2,8-dione (180 mg, 0.88 mmol) in dichloromethane (20 mL) was added $N^1,N^1,N^2,N^2$-tetramethylethane-1,2-diamine (406 mg, 3.49 mmol), followed by iodotrimethylsilane (699 mg, 3.49 mmol) at −15° C. After addition, the mixture was stirred at −15° C. for 1 h, and iodine (332 mg, 1.31 mmol) was added. The mixture was stirred at −15° C. for another 2 h and quenched by addition of aqueous sodium thiosulfate (50%, 20 mL). The mixture was extracted with dichloromethane (3×20 mL). The combined organic layers were washed with water (20 mL), brine (20 mL), dried over anhydrous sodium sulfate and concentrated under reduced pressure. The residue was purified by column chromatography (silica gel, 100-200 mesh, 0 to 10% methanol in dichloromethane) to afford 3-iodo-1,7-dimethyl-4,5-dihydro-3H-pyrido[4,3-b]azepine-2,8-dione (160 mg, 55%) as a white solid. Used in the next step as is.

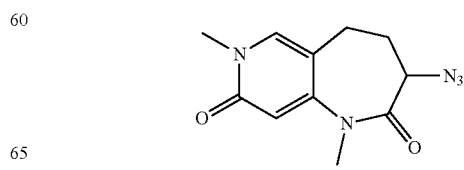

Step 10: 3-azido-1,7-dimethyl-4,5-dihydro-3H-pyrido[4,3-b]azepine-2,8-dione

To a solution of 3-iodo-1,7-dimethyl-4,5-dihydro-3H-pyrido[4,3-b]azepine-2,8-dione (160 mg, 0.48 mmol) in N,N-dimethylformamide (5 mL) was added sodium azide (63 mg, 0.96 mmol). The reaction mixture was stirred at 25° C. for 16 h and then diluted with water (20 mL). The resulting mixture was extracted with dichloromethane (3×20 mL). The combined organic layers were washed with water (20 mL), brine (20 mL), dried over anhydrous sodium sulfate and concentrated under reduced pressure to afford crude 3-azido-1,7-dimethyl-4,5-dihydro-3H-pyrido[4,3-b]azepine-2,8-dione (110 mg, 92%) as yellow oil, used in the next step without further purification.

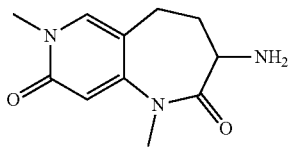 [SMILES: CN1C(=O)C(N)CCc2cn(C)c(=O)cc21]

Step 11: 3-amino-1,7-dimethyl-4,5-dihydro-3H-pyrido[4,3-b]azepine-2,8-dione

To a solution of 3-azido-1,7-dimethyl-4,5-dihydro-3H-pyrido[4,3-b]azepine-2,8-dione (110 mg, 0.44 mmol) in tetrahydrofuran (5 mL) and water (1 mL) was added 80% polymer-bound triphenylphosphine (233 mg). The reaction mixture was stirred at 25° C. for 2 h and then filtered. The filtrate was concentrated under reduced pressure to afford 3-amino-1,7-dimethyl-4,5-dihydro-3H-pyrido[4,3-b]azepine-2,8-dione (95 mg, 97%) as a white solid, use in the next step without further purification.

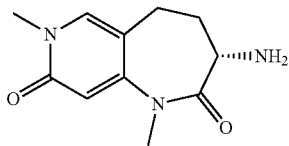 [SMILES: CN1C(=O)[C@@H](N)CCc2cn(C)c(=O)cc21]

Step 12: (S)-3-amino-1,7-dimethyl-4,5-dihydro-1H-pyrido[4,3-b]azepine-2,8(3H,7H)-dione 3-amino-1,7-dimethyl-4,5-dihydro-3H-pyrido[4,3-b]azepine-2,8-dione (95 mg, 0.43 mmol) was separated by chiral SFC to give arbitrarily assigned:
(S)-3-amino-1,7-dimethyl-4,5-dihydro-1H-pyrido[4,3-b]azepine-2,8(3H,7H)-dione (peak 1, retention time=4.105 min, 45 mg, 47%) and (R)-3-amino-1,7-dimethyl-4,5-dihydro-1H-pyrido[4,3-b]azepine-2,8(3H,7H)-dione (peak 2, retention time=5.841 min, 45 mg, 47%), both as yellow oil.

SFC conditions: Column: Lux Cellulose-2 150×4.6 mm I.D., 3 µm Mobile phase: 40% of Methanol (0.05% DEA) in $CO_2$ Flow rate: 2.5 mL/min Column temperature: 40° C.

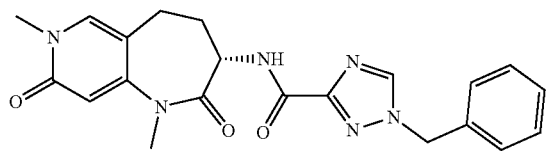 [SMILES: CN1C(=O)[C@@H](NC(=O)c2ncn(Cc3ccccc3)n2)CCc2cn(C)c(=O)cc21]

Step 13: 1-benzyl-N-[(3S)-1,7-dimethyl-2,8-dioxo-4,5-dihydro-3H-pyrido[4,3-b]azepin-3-yl]-1,2,4-triazole-3-carboxamide A mixture of (3S)-3-amino-1,7-dimethyl-4,5-dihydro-3H-pyrido [4,3-b]azepine-2,8-dione (15 mg, 0.07 mmol), 1-hydroxybenzotriazole (11 mg, 0.08 mmol), 1-(3-dimethylaminopropyl)-3-ethylcarbodiimidehydrochloride (16 mg, 0.08 mmol) and 1-benzyl-1,2,4-triazole-3-carboxylic acid (17 mg, 0.08 mmol) in N,N-dimethylformamide (3 mL) was stirred at 25° C. for 2 h. The solvent was removed under reduced pressure. The residue was purified by HPLC reverse phase chromatography (acetonitrile 17-47%/0.05% $NH_4OH$ in water) to afford arbitrarily assigned 1-benzyl-N-[(3S)-1,7-dimethyl-2,8-dioxo-4,5-dihydro-3H-pyrido[4,3-b]azepin-3-yl]-1,2,4-triazole-3-carboxamide (16.6 mg, 60%) as a white solid. $^1$H NMR (400 MHz, $CD_3OD$) δ 8.57 (s, 1H), 7.63 (s, 1H), 7.38-7.32 (m, 5H), 6.46 (s, 1H), 5.47 (s, 2H), 4.64-4.59 (m, 1H), 3.57 (s, 3H), 3.36 (s, 3H), 2.67-2.61 (m, 2H), 2.45-2.41 (m, 1H), 2.10-2.06 (m, 1H). LCMS $R_T$=0.582 min, m/z=407.1 [M+H]$^+$. LCMS (5 to 95% acetonitrile in water+0.1% formic acid over 1.5 mins) retention time 0.582 min, ESI+ found [M+H]=407.1.

Example 6

Method #6

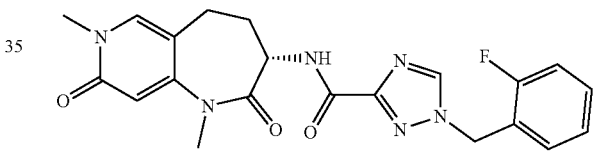

1-[(2-fluorophenyl)methyl]-N-[(3S)-1,7-dimethyl-2,8-dioxo-4,5-dihydro-3H-pyrido[4,3-b]azepin-3-yl]-1,2,4-triazole-3-carboxamide A mixture of (3S)-3-amino-1,7-dimethyl-4,5-dihydro-3H-pyrido[4,3-b]azepine-2,8-dione (15 mg, 0.07 mmol), 1-hydroxybenzotriazole (11 mg, 0.08 mmol), 1-(3-dimethylaminopropyl)-3-ethylcarbodiimidehydrochloride (16 mg, 0.08 mmol) and 1-[(2-fluorophenyl)methyl]-1,2,4-triazole-3-carboxylic acid (18 mg, 0.08 mmol) in N,N-dimethylformamide (3 mL) was stirred at 25° C. for 2 h. The solvent was removed under reduced pressure. The residue was purified by reverse phase chromatography (acetonitrile 16-46%/ 0.05% $NH_4OH$ in water) to afford arbitrarily assigned 1-[(2-fluorophenyl)methyl]-N-[(3S)-1,7-dimethyl-2,8-dioxo-4,5-dihydro-3H-pyrido[4,3-b]azepin-3-yl]-1,2,4-triazole-3-carboxamide (16.5 mg, 57%) as a white solid. $^1$H NMR (400 MHz, $CD_3OD$) δ 8.58 (s, 1H), 7.63 (s, 1H), 7.41-7.36 (m, 2H), 7.22-7.15 (m, 2H), 6.46 (s, 1H), 5.55 (s, 2H), 4.64-4.59 (m, 1H), 3.57 (s, 3H), 3.36 (s, 3H), 2.67-2.61 (m, 2H), 2.45-2.41 (m, 1H), 2.10-2.06 (m, 1H). LCMS $R_T$=0.587 min, m/z=425 [M+H]$^+$. LCMS (5 to 95% acetonitrile in water+0.1% formic acid over 1.5 mins) retention time 0.587 min, ESI+ found [M+H]=425.

Example 7

Method #7

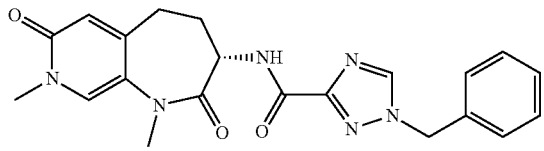 [SMILES: CN1C(=O)[C@@H](NC(=O)c2ncn(Cc3ccccc3)n2)CCc2cc(=O)n(C)cc21]

1-benzyl-N-[(3S)-1,8-dimethyl-2,7-dioxo-4,5-di-
hydro-3H-pyrido[3,4-b]azepin-3-yl]-1,2,4-triazole-3-
carboxamide

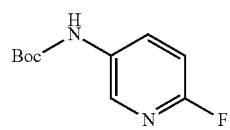 [SMILES: CC(C)(C)OC(=O)Nc1ccc(F)nc1]

Step 1: tert-butyl N-(6-fluoro-3-pyridyl)carbamate

To a solution of 6-fluoro-3-pyridinylamine (18.0 g, 160.56 mmol) in dichloromethane (10 mL) was added pyridine (25.4 g, 321.11 mmol) and di-tert-butyldicarbonate (42.1 g, 192.67 mmol). The reaction mixture was stirred at 20° C. for 2 h and subsequently concentrated under reduced pressure. The residue was purified by column chromatography (silica gel, 100-200 mesh, 0 to 10% ethyl acetate in petroleum ether) to give tert-butyl N-(6-fluoro-3-pyridyl)carbamate (19.0 g, 56%) as a white solid, used as is in the next step.

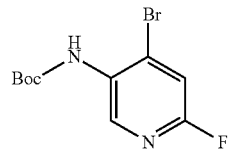 [SMILES: CC(C)(C)OC(=O)Nc1cnc(F)cc1Br]

Step 2: tert-butyl N-(4-bromo-6-fluoro-3-pyridyl)carbamate

To a solution of tert-butyl N-(6-fluoro-3-pyridyl)carbamate (8.0 g, 37.7 mmol) in tetrahydrofuran (100 mL) was added tert-butyllithium (1.3 M in Hexanes, 120 mL, 156.0 mmol) at −78° C. under nitrogen atmosphere. The reaction mixture was stirred at −40° C. for 1 h and subsequently 1,2-dibromoethane (35.41 g, 188.5 mmol) was added. The resulting mixture was stirred at −78° C. for 2 h and warmed to 25° C. over 16 h. The reaction mixture was quenched by addition of saturated aqueous ammonium chloride (300 mL) and extracted with ethyl acetate (3×150 mL). The combined organic layers were washed with water (150 mL), brine (150 mL), dried over sodium sulfate and concentrated under reduced pressure. The residue was purified by column chromatography (silica gel, 100-200 mesh, 0 to 10% ethyl acetate in petroleum ether) to tert-butyl N-(4-bromo-6-fluoro-3-pyridyl)carbamate (3.0 g, 27%) as yellow oil. $^1$H NMR (400 MHz, DMSO-d$_6$) 8.95 (s, 1H), 8.21 (s, 1H), 7.68 (d, J=4.0 Hz, 1H), 1.45 (s, 9H).

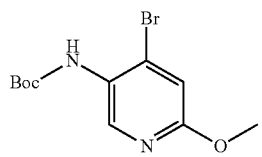 [SMILES: COc1cc(Br)c(NC(=O)OC(C)(C)C)cn1]

Step 3: tert-butyl N-(4-bromo-6-methoxy-3-pyridyl)carbamate

To a solution of tert-butyl N-(4-bromo-6-fluoro-3-pyridyl)carbamate (2.5 g, 8.59 mmol) in methanol (5 mL) was added sodium methoxide (2.3 g, 42.94 mmol). The resulting mixture was stirred at 25° C. for 16 h and then quenched by addition of water (50 mL). The mixture was extracted with ethyl acetate (3×50 mL). The combined organic layers were washed with water (50 mL), brine (50 mL), dried over sodium sulfate and concentrated under reduced pressure to afford crude tert-butyl N-(4-bromo-6-methoxy-3-pyridyl)carbamate (2.5 g, 96%) as yellow oil, used in the next step without further purification.

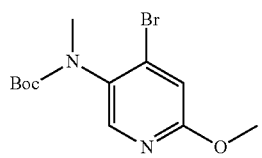 [SMILES: COc1cc(Br)c(N(C)C(=O)OC(C)(C)C)cn1]

Step 4: tert-butyl N-(4-bromo-6-methoxy-3-pyridyl)-N-methyl-carbamate

To a solution of tert-butyl N-(4-bromo-6-methoxy-3-pyridyl)carbamate (2.5 g, 8.25 mmol) in N,N-dimethylformamide (40 mL) was added iodomethane (3.3 g, 23.18 mmol) and cesium carbonate (5.4 g, 16.49 mmol). The reaction mixture was stirred at 25° C. for 2 h and then diluted with water (20 mL). The mixture was extracted with ethyl acetate (3×30 mL). The combined organic layers were washed with water (20 mL), brine (20 mL), dried over sodium sulfate and concentrated under reduced pressure to afford crude tert-butyl N-(4-bromo-6-methoxy-3-pyridyl)-N-methyl-carbamate (2.5 g, 96%) as yellow oil, used in the next step without further purification. LCMS R$_T$=0.873 min, m/z=302.8 [M+H]$^+$. LCMS (5 to 95% acetonitrile in water+ 0.1% formic acid over 1.5 mins) retention time 0.873 min, ESI+ found [M+H]=302.8.

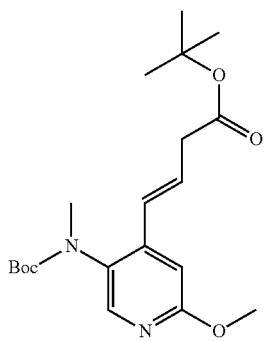 [SMILES: COc1cc(/C=C/CC(=O)OC(C)(C)C)c(N(C)C(=O)OC(C)(C)C)cn1]

Step 5: tert-butyl (E)-4-[5-[tert-butoxycarbonyl (methyl)amino]-2-methoxy-4-pyridyl]but-3-enoate A mixture of tert-butyl N-(4-bromo-6-methoxy-3-pyridyl)-N-methyl-carbamate (2.5 g, 7.88 mmol), tert-butyl but-3-enoate (2.24 g, 15.76 mmol), sodium bicarbonate (2.0 g, 23.65 mmol) and dicyclohexyl-[2-(2,4,6-triisopropyl-3-phenyl-phenyl)phenyl]phosphane dichloropalladium (1.0 g, 0.79 mmol) in N,N-dimethylformamide (5 mL) was heated at 100° C. for 3 h. After cooled, the mixture was diluted with water (40 mL) and extracted with ethyl acetate (3×30 mL). The combined organic layers were washed with water (20 mL), brine (20 mL), dried over sodium sulfate and concentrated under reduced pressure to afford crude tert-butyl (E)-4-[5-[tert-butoxycarbonyl(methyl)amino]-2-methoxy-4-pyridyl]but-3-enoate (2.0 g, 67%) as yellow oil, used in the next step without further purification. LCMS $R_T$=0.906 min, m/z=379.0 [M+H]$^+$. LCMS (5 to 95% acetonitrile in water+0.1% formic acid over 1.5 mins) retention time 0.906 min, ESI+ found [M+H]=379.0.

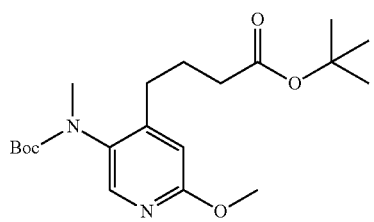 [SMILES: COc1cc(CCCC(=O)OC(C)(C)C)c(N(C)C(=O)OC(C)(C)C)cn1]

Step 6: tert-butyl 4-[5-[tert-butoxycarbonyl(methyl) amino]-2-methoxy-4-pyridyl]butanoate A mixture of tert-butyl (E)-4-[5-[tert-butoxycarbonyl (methyl)amino]-2-methoxy-4-pyridyl]but-3-enoate (2.0 g, 5.28 mmol) and Palladium (10% on carbon, 562 mg) in ethyl acetate (60 mL) was hydrogenated (15 psi) at 25° C. for 16 h and subsequently filtered. The filtrate was concentrated under reduced pressure to afford crude tert-butyl 4-[5-[tert-butoxycarbonyl(methyl)amino]-2-methoxy-4-pyridyl]butanoate (2.0 g, 99.5%) as a yellow oil, used in the next step without further purification.

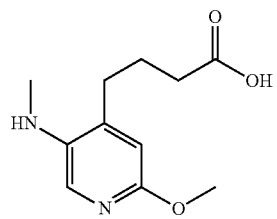 [SMILES: CNc1cnc(OC)cc1CCCC(=O)O]

Step 7: 4-[2-methoxy-5-(methylamino)-4-pyridyl] butanoic Acid

To a solution of tert-butyl 4-[5-[tert-butoxycarbonyl (methyl)amino]-2-methoxy-4-pyridyl]butanoate (2.0 g, 5.26 mmol) in 1,4-dioxane (10 mL) was added hydrochloric acid (4.0 M in dioxane, 40 mL, 160.0 mmol). The reaction mixture was stirred at 25° C. for 2 h and concentrated under reduced pressure to afford crude 4-[2-methoxy-5-(methylamino)-4-pyridyl]butanoic acid (1.15 g, 98%) as a yellow oil, used in the next step without further purification.

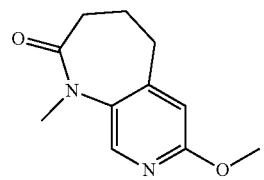

Step 8: 7-methoxy-1-methyl-4,5-dihydro-3H-pyrido [3,4-b]azepin-2-one

To a solution of 4-[2-methoxy-5-(methylamino)-4-pyridyl]butanoic acid (1.15 g, 5.13 mmol) in N,N-dimethylformamide (100 mL) was added N,N-diisopropylethylamine (663 mg, 5.13 mmol) and 2-(3H-[1,2,3]triazolo[4,5-b]pyridin-3-yl)-1,1,3,3-tetramethylisouronium hexafluorophosphate (V) (1.95 g, 5.13 mmol). The reaction mixture was stirred at 25° C. for 2 h and then diluted with water (100 mL). The mixture was extracted with ethyl acetate (3×50 mL). The combined organic layers were washed with water (50 mL), brine (50 mL), dried over sodium sulfate and concentrated under reduced pressure. The residue was purified by column chromatography (silica gel, 100-200 mesh, 0 to 30% ethyl acetate in petroleum ether) to afford 7-methoxy-1-methyl-4,5-dihydro-3H-pyrido [3,4-b]azepin-2-one (800 mg, 76%) as a yellow solid. LCMS $R_T$=0.601 min, m/z=207.0 [M+H]$^+$. LCMS (5 to 95% acetonitrile in water+0.1% formic acid over 1.5 mins) retention time 0.601 min, ESI+ found [M+H]=207.0.

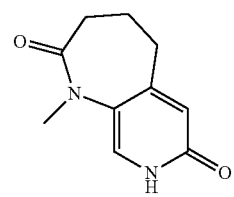

Step 9: 1-methyl-3,4,5,8-tetrahydropyrido[3,4-]azepine-2,7-dione

To a solution of 7-methoxy-1-methyl-4,5-dihydro-3H-pyrido[3,4-b]azepin-2-one (400 mg, 1.94 mmol) in acetonitrile (20 mL) was added potassium iodide (966 mg, 5.82 mmol) and chlorotrimethylsilane (632 mg, 5.82 mmol). The reaction mixture was heated at 70° C. for 3 h and filtered. The filtrate was concentrated under reduced pressure and the residue was purified by column chromatography (silica gel, 100-200 mesh, 0 to 10% methanol in dichloromethane) to afford 1-methyl-3,4,5,8-tetrahydropyrido[3,4-b]azepine-2,7-dione (350 mg, 94%) as a yellow oil, used as is in the next step.

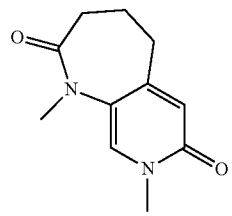

Step 10: 1,8-dimethyl-4,5-dihydro-3H-pyrido[3,4-]azepine-2,7-dione

To a solution of 1-methyl-3,4,5,8-tetrahydropyrido[3,4-b]azepine-2,7-dione (350 mg, 1.82 mmol) in N,N-dimethylformamide (15 mL) was added iodomethane (388 mg, 2.73 mmol) and cesium carbonate (1.19 g, 3.64 mmol). The reaction mixture was stirred at 25° C. for 3 h and filtered. The filtrate was concentrated under reduced pressure. The residue was purified by column chromatography (silica gel, 100-200 mesh, 0 to 10% methanol in dichloromethane) to afford 1,8-dimethyl-4,5-dihydro-3H-pyrido[3,4-b]azepine-2,7-dione (300 mg, 80%) as a yellow solid, used as is in the next step.

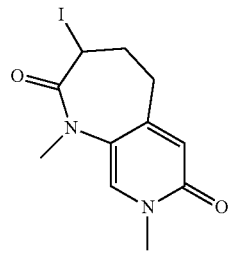 [SMILES: CN1C(=O)C(I)CCc2cc(=O)n(C)cc21]

Step 11: 3-iodo-1,8-dimethyl-4,5-dihydro-3H-pyrido[3,4-]azepine-2,7-dione

To a solution of 1,8-dimethyl-4,5-dihydro-3H-pyrido[3,4-b]azepine-2,7-dione (150 mg, 0.73 mmol) in dichloromethane (15 mL) was added $N^1,N^1,N^2,N^2$-tetramethylethane-1,2-diamine (845 mg, 7.27 mmol) and iodotrimethylsilane (1.48 g, 7.27 mmol) at −15° C. After addition, the mixture was stirred at −15° C. for 2 h and then iodine (738 mg, 2.91 mmol) was added. The reaction mixture was allowed to warm to 0° C. and stirred for 2 h. The mixture was quenched by addition of saturated aqueous sodium thiosulfate (10 mL). The resulting mixture was extracted with dichloromethane (3×20 mL). The combined organic layers were washed with water (20 mL), brine (20 mL), dried over sodium sulfate and concentrated under reduced pressure. The residue was purified by column chromatography (silica gel, 100-200 mesh, 0 to 5% methanol in dichloromethane) to afford 3-iodo-1,8-dimethyl-4,5-dihydro-3H-pyrido[3,4-b]azepine-2,7-dione (220 mg, 91%) as yellow oil, used as is in the next step.

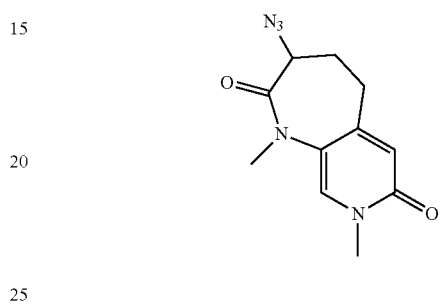

Step 12: 3-azido-1,8-dimethyl-4,5-dihydro-3H-pyrido[3,4-b]azepine-2,7-dione

To a solution of 3-iodo-1,8-dimethyl-4,5-dihydro-3H-pyrido[3,4-b]azepine-2,7-dione (220 mg, 0.66 mmol) in dichloromethane (15 mL) was added sodium azide (2.65 g, 40.76 mmol). The reaction mixture was stirred at 25° C. for 2 h and then diluted with water (20 mL). The mixture was extracted with dichloromethane (3×20 mL). The combined organic layers were washed with water (20 mL), brine (20 mL), dried over sodium sulfate and concentrated under reduced pressure to afford 3-azido-1,8-dimethyl-4,5-dihydro-3H-pyrido[3,4-b]azepine-2,7-dione (150 mg, 92%) as a yellow oil, used in the next step without further purification.

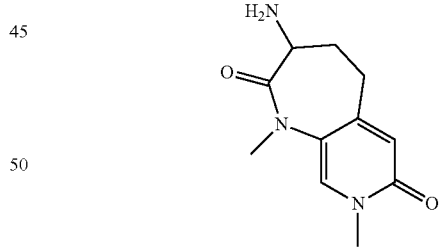

Step 13: 3-amino-1,8-dimethyl-4,5-dihydro-3H-pyrido[3,4-b]azepine-2,7-dione

A mixture of 3-azido-1,8-dimethyl-4,5-dihydro-3H-pyrido[3,4-b]azepine-2,7-dione (150 mg, 0.73 mmol) and palladium (10% on carbon, 155 mg) in methanol (15 mL) was hydrogenated (15 psi) at 25° C. for 2 h and filtered. The filtrate was concentrated under reduced pressure to afford crude 3-amino-1,8-dimethyl-4,5-dihydro-3H-pyrido[3,4-b]azepine-2,7-dione (120 mg, 75%) as colorless oil, used in the next step without further purification.

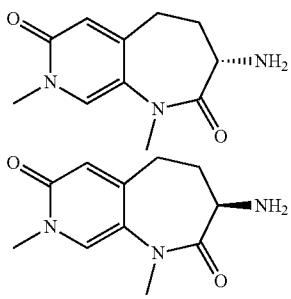

Step 14: (3S)-3-amino-1,8-dimethyl-4,5-dihydro-3H-pyrido[3,4-b]azepine-2,7-dione and (3R)-3-amino-1,8-dimethyl-4,5-dihydro-3H-pyrido[3,4-b]azepine-2,7-dione 3-amino-1,8-dimethyl-4,5-dihydro-3H-pyrido[3,4-b]azepine-2,7-dione (120 mg, 0.54 mmol) was separated by chiral SFC to give arbitrarily assigned (3R)-3-amino-1,8-dimethyl-4,5-dihydro-3H-pyrido[3,4-b]azepine-2,7-dione (peak 1, retention time 3.528 min) (45 mg, 38%) and (3S)-3-amino-1,8-dimethyl-4,5-dihydro-3H-pyrido[3,4-b]azepine-2,7-dione (peak 2, retention time, 4.999 min) (45 mg, 38%) (45 mg, 38%) as yellow oils.

SFC condition: Column: Chiralpak AS-3 150×4.6 mm I.D., 3 μm Mobile phase: A: $CO_2$ B: methanol (0.05% DEA) Gradient: from 5% to 40% of B in 5 min and hold 40% for 2.5 min, then 5% of B for 2.5 min Flow rate: 2.5 mL/min Column temp.: 35° C.

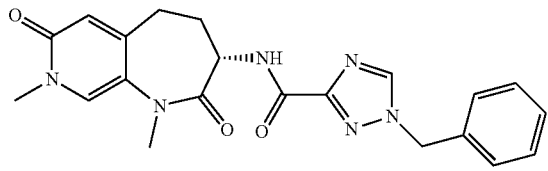 [SMILES: CN1C(=O)[C@@H](NC(=O)c2ncn(Cc3ccccc3)n2)CCc2cc(=O)n(C)cc21]

Step 15: (S)-1-benzyl-N-(1,8-dimethyl-2,7-dioxo-2,3,4,5,7,8-hexahydro-1H-pyrido[3,4-b]azepin-3-yl)-1H-1,2,4-triazole-3-carboxamide A mixture of (3S)-3-amino-1,8-dimethyl-4,5-dihydro-3H-pyrido[3,4-b]azepine-2,7-dione (15 mg, 0.07 mmol), 1-(3-dimethylaminopropyl)-3-ethylcarbodiimidehydrochloride (16 mg, 0.08 mmol), 1-hydroxybenzotriazole (11 mg, 0.08 mmol) and 1-benzyl-1,2,4-triazole-3-carboxylic acid (17 mg, 0.08 mmol) in N,N-dimethylformamide (3 mL) was stirred at 25° C. for 2 h. The mixture was concentrated under reduced pressure and the residue was purified by RP-HPLC (acetonitrile 20-50%/0.05% ammonium hydroxide in water) to afford arbitrarily assigned (S)-1-benzyl-N-(1,8-dimethyl-2,7-dioxo-2,3,4,5,7,8-hexahydro-1H-pyrido[3,4-b]azepin-3-yl)-1H-1,2,4-triazole-3-carboxamide (22.2 mg, 78%) as a white solid. $^1$H NMR (400 MHz, $CD_3OD$) 8.56 (s, 1H), 7.87 (s, 1H), 7.37-7.33 (m, 5H), 6.49 (s, 1H), 5.46 (s, 2H), 4.71-4.65 (m, 1H), 3.59 (s, 3H), 3.32 (s, 3H), 2.74-2.68 (m, 2H), 2.45-2.38 (m, 1H), 2.13-2.08 (m, 1H). LCMS $R_T$=0.697 min, m/z=407.1 [M+H]$^+$. LCMS (5 to 95% acetonitrile in water+0.1% formic acid over 1.5 mins) retention time 0.697 min, ESI+ found [M+H]=407.1.

Example 8

Method #8

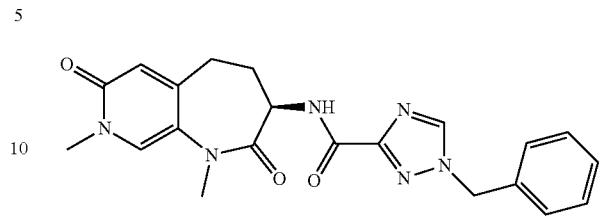

Step 1: (R)-1-benzyl-N-(1,8-dimethyl-2,7-dioxo-2,3,4,5,7,8-hexahydro-1H-pyrido[3,4-b]azepin-3-yl)-1H-1,2,4-triazole-3-carboxamide A mixture of (3R)-3-amino-1,8-dimethyl-4,5-dihydro-3H-pyrido[3,4-b]azepine-2,7-dione (15 mg, 0.07 mmol), 1-hydroxybenzotriazole (11 mg, 0.08 mmol), 1-(3-dimethylaminopropyl)-3-ethylcarbodiimidehydrochloride (16 mg, 0.08 mmol) and 1-benzyl-1,2,4-triazole-3-carboxylic acid (17 mg, 0.08 mmol) in N,N-dimethylformamide (3 mL) was stirred at 25° C. for 2 h. The mixture was concentrated under reduced pressure and the residue was purified by RP-HPLC (acetonitrile 20-50%/0.05% ammonium hydroxide in water) to afford arbitrarily assigned (R)-1-benzyl-N-(1,8-dimethyl-2,7-dioxo-2,3,4,5,7,8-hexahydro-1H-pyrido[3,4-b]azepin-3-yl)-1H-1,2,4-triazole-3-carboxamide (21.2 mg, 76%) as a white solid. $^1$H NMR (400 MHz, $CD_3OD$) 8.56 (s, 1H), 7.87 (s, 1H), 7.37-7.33 (m, 5H), 6.49 (s, 1H), 5.47 (s, 2H), 4.71-4.65 (m, 1H), 3.59 (s, 3H), 3.33 (s, 3H), 2.74-2.69 (m, 2H), 2.45-2.38 (m, 1H), 2.13-2.08 (m, 1H). LCMS $R_T$=0.702 min, m/z=407.1 [M+H]$^+$. LCMS (5 to 95% acetonitrile in water+0.1% formic acid over 1.5 mins) retention time 0.702 min, ESI+ found [M+H]=407.1.

Example 9

Method #9

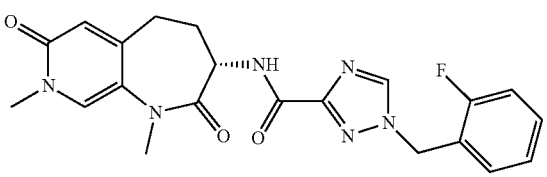 [SMILES: CN1C(=O)[C@@H](NC(=O)c2ncn(Cc3ccccc3F)n2)CCc2cc(=O)n(C)cc21]

(S)—N-(1,8-dimethyl-2,7-dioxo-2,3,4,5,7,8-hexahydro-1H-pyrido[3,4-b]azepin-3-yl)-1-(2-fluorobenzyl)-1H-1,2,4-triazole-3-carboxamide Amide coupling was prepared in a similar fashion to Method #1. The crude was purified by RP-HPLC (acetonitrile 18-48%/0.05% ammonium hydroxide in water) to afford arbitrarily assigned (S)—N-(1,8-dimethyl-2,7-dioxo-2,3,4,5,7,8-hexahydro-1H-pyrido[3,4-b]azepin-3-yl)-1-(2-fluorobenzyl)-1H-1,2,4-triazole-3-carboxamide (12.3 mg, 43%) as a white solid. $^1$H NMR (400 MHz, $CD_3OD$) 8.57 (s, 1H), 7.87 (s, 1H), 7.40-7.35 (m, 2H), 7.21-7.14 (m, 2H), 6.49 (s, 1H), 5.45 (s, 2H), 4.71-4.65 (m, 1H), 3.59 (s, 3H), 3.32 (s, 3H), 2.74-2.69 (m, 2H), 2.45-2.38 (m, 1H), 2.13-

2.08 (m, 1H). LCMS R$_T$=0.708 min, m/z=425.1 [M+H]$^+$. LCMS (5 to 95% acetonitrile in water+0.1% formic acid over 1.5 mins) retention time 0.708 min, ESI+ found [M+H]= 425.1.

Example 10

Method #10

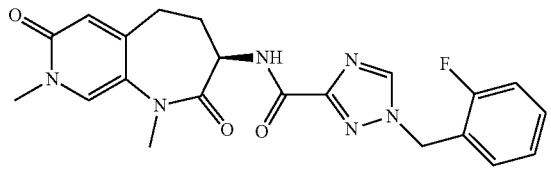 [SMILES: CN1C(=O)[C@H](NC(=O)c2ncn(Cc3ccccc3F)n2)CCc2cc(=O)n(C)cc21]

(R)—N-(1,8-dimethyl-2,7-dioxo-2,3,4,5,7,8-hexahydro-1H-pyrido[3,4-b]azepin-3-yl)-1-(2-fluorobenzyl)-1H-1,2,4-triazole-3-carboxamide Amide coupling was prepared in a similar fashion to Method #2. The crude was purified by RP-HPLC (acetonitrile 18-48%/0.05% ammonium hydroxide in water) to afford arbitrarily assigned (R)—N-(1,8-dimethyl-2,7-dioxo-2,3,4,5,7,8-hexahydro-1H-pyrido[3,4-b]azepin-3-yl)-1-(2-fluorobenzyl)-1H-1,2,4-triazole-3-carboxamide (14.4 mg, 49%) as a white solid. $^1$H NMR (400 MHz, CD$_3$OD) 8.57 (s, 1H), 7.87 (s, 1H), 7.40-7.35 (m, 2H), 7.21-7.14 (m, 2H), 6.49 (s, 1H), 5.45 (s, 2H), 4.71-4.65 (m, 1H), 3.59 (s, 3H), 3.32 (s, 3H), 2.74-2.69 (m, 2H), 2.45-2.38 (m, 1H), 2.13-2.08 (m, 1H). LCMS R$_T$=0.702 min, m/z=425.1 [M+H]$^+$. LCMS (5 to 95% acetonitrile in water+0.1% formic acid over 1.5 mins) retention time 0.702 min, ESI+ found [M+H]= 425.1.

Example 11

Method #11

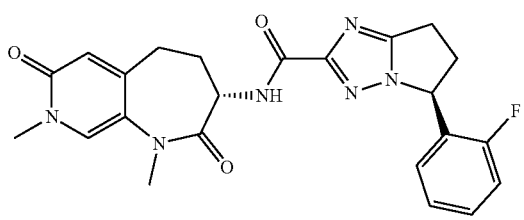 [SMILES: CN1C(=O)[C@@H](NC(=O)c2nc3n(n2)[C@H](c2ccccc2F)CC3)CCc2cc(=O)n(C)cc21]

(5S)-5-(2-fluorophenyl)-N-[(3S)-1,8-dimethyl-2,7-dioxo-4,5-dihydro-3H-pyrido[3,4-b]azepin-3-yl]-6,7-dihydro-5H-pyrrolo[1,2-b][1,2,4]triazole-2-carboxamide

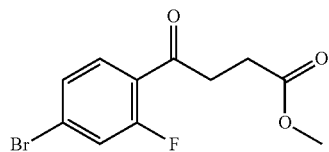 [SMILES: COC(=O)CCC(=O)c1ccc(Br)cc1F]

Step 1: methyl 4-(4-bromo-2-fluorophenyl)-4-oxobutanoate

To a solution of 1-bromo-3-fluorobenzene (22 g, 125.71 mmol) in 1,2-dichloroethane (300 mL) was added aluminum chloride (67 g, 502.86 mmol) portion-wise, followed by methyl 4-chloro-4-oxobutyrate (38 g, 251.43 mmol) at 25° C. The mixture was stirred at 70° C. for 12 h and then quenched by addition of aqueous sodium hydroxide (10%, 150 mL). The formed solid was removed by filtration and the filtrate was extracted with ethyl acetate (3×200 mL). The combined organic layers were washed with water (150 mL), brine (150 mL), dried over sodium sulfate and concentrated under reduced pressure. The residue was purified by column chromatography (silica gel, 100-200 mesh, 0 to 6% ethyl acetate in petroleum ether) to afford methyl 4-(4-bromo-2-fluoro-phenyl)-4-oxo-butanoate (12.5 g, 34%) as a yellow solid. $^1$H NMR (400 MHz, CDCl$_3$) δ 7.79 (t, J=8.4 Hz, 1H), 7.38 (t, J=10.8 Hz, 2H), 3.71 (s, 3H), 3.31-3.27 (m, 2H), 2.75 (t, J=6.4 Hz, 2H).

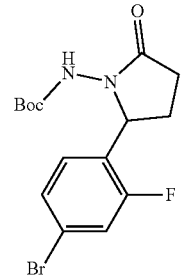 [SMILES: CC(C)(C)OC(=O)NN1C(=O)CCC1c1ccc(Br)cc1F]

Step 2: tert-butyl (2-(4-bromo-2-fluorophenyl)-5-oxopyrrolidin-1-yl)carbamate

To a solution of methyl 4-(4-bromo-2-fluoro-phenyl)-4-oxo-butanoate (12.0 g, 41.52 mmol) in acetic acid (60 mL) and tetrahydrofuran (120 mL) was added tert-butyl hydrazinecarboxylate (24.7 g, 186.79 mmol). The mixture was stirred 53° C. for 16 h. After cooling to 25° C., to the reaction mixture was added sodium cyanoborohydride (11.7 g, 186.79 mmol) and heated at 53° C. for another 7 h. The solvent was removed under reduced pressure and to the residue was added aqueous saturated sodium bicarbonate (300 mL). The resulting mixture was extracted with ethyl acetate (2×200 mL). The combined organic layers were washed with brine (2×100 mL), dried over sodium sulfate and concentrated under reduce pressure. The residue was purified by column chromatography (silica gel, 100-200 mesh, 0 to 30% ethyl acetate in petroleum ether) to afford tert-butyl N-[2-(4-bromo-2-fluoro-phenyl)-5-oxo-pyrrolidin-1-yl]carbamate (18.8 g, 86%, 70% purity) as a white solid. LCMS RT=0.871 min, m/z=318.8 [M−56]$^+$. LCMS (5 to 95% acetonitrile in water+0.03% trifluoroacetic acid over 1.5 mins) retention time 0.871 min, ESI+ found [M−56]= 318.8.

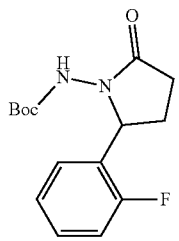 [SMILES: CC(C)(C)OC(=O)NN1C(=O)CCC1c1ccccc1F]

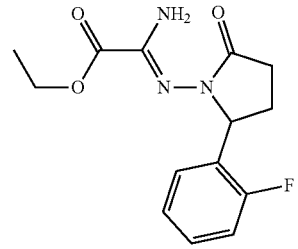

Step 3: tert-butyl (2-(2-fluorophenyl)-5-oxopyrrolidin-1-yl)carbamate

A mixture of tert-butyl N-[2-(4-bromo-2-fluoro-phenyl)-5-oxo-pyrrolidin-1-yl]carbamate (15.1 g, 40.47 mmol) and palladium (10% on carbon, 4.3 g) in methanol (300 mL) was hydrogenated (15 psi) at 25° C. for 6 h and subsequently filtered. The filtrate was concentrated under reduced pressure to give crude tert-butyl N-[2-(2-fluorophenyl)-5-oxo-pyrrolidin-1-yl]carbamate (11.76 g, 98%) as a white solid. LCMS RT=0.797 min, m/z=238.9 [M−56]+.

LCMS (5 to 95% acetonitrile in water+0.03% trifluoroacetic acid over 1.5 mins) retention time 0.797 min, ESI+ found [M−56]=238.9.

Step 5: ethyl (2Z)-2-amino-2-[2-(2-fluorophenyl)-5-oxo-pyrrolidin-1-yl]imino-acetate To a solution of 1-amino-5-(2-fluorophenyl) pyrrolidin-2-one (6.6 g, 33.98 mmol) in ethanol (50 mL) was added ethyl 2-ethoxy-2-imino-acetate (24.7 g, 169.92 mmol). The mixture was stirred at 90° C. for 16 h and concentrated under reduce pressure to afford crude ethyl (2Z)-2-amino-2-[2-(2-fluorophenyl)-5-oxo-pyrrolidin-1-yl] imino acetate (9.0 g, 90%) as brown oil, used in the next step without further purification. LCMS RT=1.498 min, m/z=294.2 [M+H]+. LCMS (0 to 60% acetonitrile in water+0.03% trifluoroacetic acid over 3.0 mins) retention time 1.498 min, ESI+ found [M+H]=294.2.

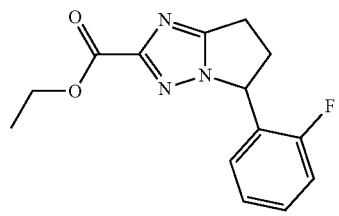

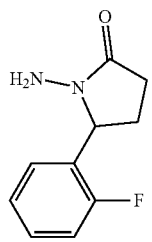 [SMILES: NN1C(=O)CCC1c1ccccc1F]

Step 4: 1-amino-5-(2-fluorophenyl)pyrrolidin-2-one

To a solution of tert-butyl N-[2-(2-fluorophenyl)-5-oxo-pyrrolidin-1-yl]carbamate (11.4 g, 38.74 mmol) in ethyl acetate (30 mL) was slowly added hydrochloric acid (4.0 M in ethyl acetate, 50 mL, 200 mmol). The mixture was stirred at 25° C. for 5 h and filtered. The collected solid was washed with ethyl acetate (30 mL) and dissolved in water (20 mL). The solution was adjusted to pH=10 by addition of saturated aqueous sodium bicarbonate (50 mL). The resulting mixture was extracted with dichloromethane (4×50 mL). The combined organic layers were washed with brine (2×100 mL), dried over sodium sulfate and concentrated under reduced pressure to afford crude 1-amino-5-(2-fluorophenyl)pyrrolidin-2-one (6.6 g, 88%) as a white solid, used in the next step without further purification. LCMS RT=1.349 min, m/z=195.2 [M+H]+. LCMS (0 to 60% acetonitrile in water+0.03% trifluoroacetic acid over 3.0 mins) retention time 1.349 min, ESI+ found [M+H]=195.2.

Step 6: ethyl 5-(2-fluorophenyl)-6,7-dihydro-5H-pyrrolo[1,2-b][1,2,4]triazole-2-carboxylate A mixture of ethyl (2Z)-2-amino-2-[2-(2-fluorophenyl)-5-oxo-pyrrolidin-1-yl]imino acetate (8.6 g, 29.33 mmol) in phosphorus oxychloride (35 mL) was heated at 120° C. for 1 h and then poured into water (200 mL) carefully. The resulting mixture was extracted with dichloromethane (4×50 mL). The combined organic layers were washed with saturated to sodium bicarbonate (80 mL), brine (50 mL), dried over sodium sulfate and concentrated under reduce pressure. The residue was purified by column chromatography (silica gel, 100-200 mesh, 0 to 3% methanol in dichloromethane) to afford ethyl 5-(2-fluorophenyl)-6,7-dihydro-5H-pyrrolo[1,2-b][1,2,4]triazole-2-carboxylate (7.1 g, 88%) as brown oil. LCMS RT=1.682 min, m/z=276.2 [M+H]+. LCMS (0 to 60% acetonitrile in water+0.03% trifluoroacetic acid over 3.0 mins) retention time 1.682 min, ESI+ found [M+H]=276.2.

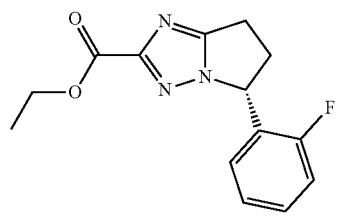 [SMILES: CCOC(=O)c1nc2n(n1)C(c1ccccc1F)CC2]

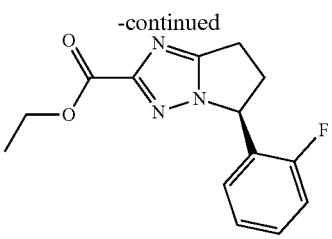

Step 7: (R)-ethyl 5-(2-fluorophenyl)-6,7-dihydro-5H-pyrrolo[1,2-b][1,2,4]triazole-2-carboxylate and (S)-ethyl 5-(2-fluorophenyl)-6,7-dihydro-5H-pyrrolo[1,2-b][1,2,4]triazole-2-carboxylate Racemic ethyl 5-(2-fluorophenyl)-6,7-dihydro-5H-pyrrolo[1,2-b][1,2,4]triazole-2-carboxylate (7.1 g, 25.79 mmol) was separated by chiral SFC to afford arbitrarily assigned:

(R)-ethyl 5-(2-fluorophenyl)-6,7-dihydro-5H-pyrrolo[1,2-b][1,2,4]triazole-2-carboxylate (Peak 1, Retention time=3.325 min) (3.0 g, 42%) as yellow oil.

(S)-ethyl 5-(2-fluorophenyl)-6,7-dihydro-5H-pyrrolo[1,2-b][1,2,4]triazole-2-carboxylate (Peak 2, Retention time=3.560 min) (2.8 g, 39%) as yellow oil.

SFC condition: Column: ChiralPak AD-3 150×4.6 mm I.D., 3 μm Mobile phase: A: CO2 B: Ethanol (0.05% DEA) Gradient: from 5% to 40% of B in 5.5 min and hold 40% for 3 min, then 5% of B for 1.5 min Flow rate: 2.5 mL/min Column temperature: 40° C.

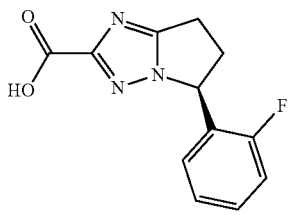 [SMILES: O=C(O)c1nc2n(n1)[C@H](c1ccccc1F)CC2]

Step 8: (S)-5-(2-fluorophenyl)-6,7-dihydro-5H-pyrrolo[1,2-b][1,2,4]triazole-2-carboxylic Acid To a solution of ethyl (5S)-5-(2-fluorophenyl)-6,7-dihydro-5H-pyrrolo[1,2-b][1,2,4]triazole-2-carboxylate (2.0 g, 7.27 mmol) in tetrahydrofuran (50 mL) and water (10 mL) was added lithium hydroxide hydrate (1.7 g, 72.65 mmol). The reaction mixture was stirred at 25° C. for 12 h and subsequently concentrated under reduce pressure. The residue was diluted with ice water (20 mL) and adjusted to pH=3 by addition of aqueous hydrochloric acid (4 M). The solid product was collected by filtration, washed with water (20 mL) and dried under reduced pressure to afford (5S)-5-(2-fluorophenyl)-6,7-dihydro-5H-pyrrolo[1,2-b][1,2,4]triazole-2-carboxylic acid (1.6 g, 89%) as a white solid, used as in the next step without further purification. $^1$H NMR (400 MHz, DMSO) δ 13.19 (br s, 1H), 7.48-7.40 (m, 1H), 7.31-7.20 (m, 3H), 5.80-5.76 (m, 1H), 3.25-3.17 (m, 1H), 3.11-2.97 (m, 2H), 2.64-2.58 (m, 1H). LCMS RT=0.586 min, m/z=248.0 [M+H]$^+$. LCMS (5 to 95% acetonitrile in water+0.03% trifluoroacetic acid over 1.5 mins) retention time 0.586 min, ESI+ found [M+H]=248.0.

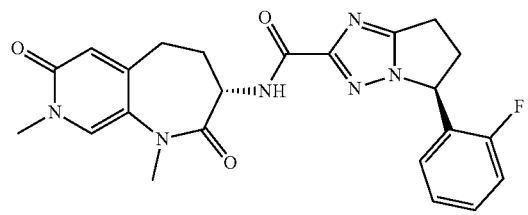 [SMILES: CN1C(=O)[C@@H](NC(=O)c2nc3n(n2)[C@H](c2ccccc2F)CC3)CCc2cc(=O)n(C)cc21]

(S)—N—((S)-1,8-dimethyl-2,7-dioxo-2,3,4,5,7,8-hexahydro-1H-pyrido[3,4-b]azepin-3-yl)-5-(2-fluorophenyl)-6,7-dihydro-5H-pyrrolo[1,2-b][1,2,4]triazole-2-carboxamide Amide coupling was prepared in a similar fashion to Method #1. The crude was purified by RP-HPLC (acetonitrile 25-55%/0.05% ammonium hydroxide in water) to afford arbitrarily assigned (S)—N—((S)-1,8-dimethyl-2,7-dioxo-2,3,4,5,7,8-hexahydro-1H-pyrido[3,4-b]azepin-3-yl)-5-(2-fluorophenyl)-6,7-dihydro-5H-pyrrolo[1,2-b][1,2,4]triazole-2-carboxamide (20.2 mg, 64%) as a white solid. $^1$H NMR (400 MHz, CD$_3$OD) 7.87 (s, 1H), 7.43-7.39 (m, 1H), 7.20-7.13 (m, 3H), 6.49 (s, 1H), 5.79-5.75 (m, 1H), 4.69-4.64 (m, 1H), 3.59 (s, 3H), 3.35-3.29 (m, 4H), 3.14-3.07 (m, 2H), 2.74-2.68 (m, 3H), 2.42-2.36 (m, 1H), 2.13-2.07 (m, 1H). LCMS R$_T$=0.727 min, m/z=451.1 [M+H]$^+$. LCMS (5 to 95% acetonitrile in water+0.1% formic acid over 1.5 mins) retention time 0.727 min, ESI+ found [M+H]=451.1.

Example 12

Method #12

Step 9: (S)—N—((R)-1,8-dimethyl-2,7-dioxo-2,3,4,5,7,8-hexahydro-1H-pyrido[3,4-b]azepin-3-yl)-5-(2-fluorophenyl)-6,7-dihydro-5H-pyrrolo[1,2-b][1,2,4]triazole-2-carboxamide Amide coupling was prepared in a similar fashion to Method #2. The crude was purified by RP-HPLC (acetonitrile 25-55%/0.05% ammonium hydroxide in water) to afford arbitrarily assigned (S)—N—((R)-1,8-dimethyl-2,7-dioxo-2,3,4,5,7,8-hexahydro-1H-pyrido[3,4-b]azepin-3-yl)-5-(2-fluorophenyl)-6,7-dihydro-5H-pyrrolo[1,2-b][1,2,4]triazole-2-carboxamide (8.8 mg, 28%) as a white solid. $^1$H NMR (400 MHz, CD$_3$OD) 7.87 (s, 1H), 7.43-7.39 (m, 1H), 7.20-7.13 (m, 3H), 6.49 (s, 1H), 5.79-5.75 (m, 1H), 4.69-4.64 (m, 1H), 3.59 (s, 3H), 3.35-3.29 (m, 4H), 3.14-3.07 (m, 2H), 2.74-2.68 (m, 3H), 2.42-2.36 (m, 1H), 2.13-2.07 (m, 1H). LCMS R$_T$=0.729 min, m/z=451.1 [M+H]$^+$. LCMS (5 to 95% acetonitrile in water+0.1% formic acid over 1.5 mins) retention time 0.729 min, ESI+ found [M+H]=451.1.

Example 13

Method #13

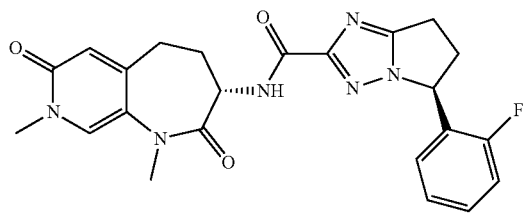 [SMILES: CN1C(=O)[C@@H](NC(=O)c2nc3n(n2)[C@H](c2ccccc2F)CC3)CCc2cc(=O)n(C)cc21]

(5S)-5-(2-fluorophenyl)-N-[(3S)-1,7-dimethyl-2,8-dioxo-4,5-dihydro-3H-pyrido[4,3-b]azepin-3-yl]-6,7-dihydro-5H-pyrrolo[1,2-b][1,2,4]triazole-2-carboxamide A mixture of (3S)-3-amino-1,7-dimethyl-4,5-dihydro-3H-pyrido[4,3-b]azepine-2,8-dione (15 mg, 0.07 mmol), 1-(3-dimethylaminopropyl)-3-ethylcarbodiimidehydrochloride (13 mg, 0.07 mmol), 1-hydroxybenzotriazole (9 mg, 0.07 mmol) and (5S)-5-(2-fluorophenyl)-6,7-dihydro-5H-pyrrolo[1,2-b][1,2,4]triazole-2-carboxylic acid (17 mg, 0.07 mmol) in N,N-dimethylformamide (5 mL) was stirred at 25° C. for 2 h. The mixture was concentrated under reduced pressure and the residue was purified by RP-HPLC (acetonitrile 21-51%/0.05% ammonium hydroxide in water) to afford arbitrarily assigned (5S)—N-[(3S)-1,7-dimethyl-2,8-dioxo-4,5-dihydro-3H-pyrido[4,3-b]azepin-3-yl]-5-(2-fluorophenyl)-6,7-dihydro-5H-pyrrolo[1,2-b][1,2,4]triazole-2-carboxamide (11.5 mg, 37%) as a white solid. $^1$H NMR (400 MHz, CD$_3$OD) $^1$H NMR (400 MHz, CD$_3$OD) 7.62 (s, 1H), 7.43-7.39 (m, 1H), 7.20-7.13 (m, 3H), 6.46 (s, 1H), 5.79-5.75 (m, 1H), 4.66-4.60 (m, 1H), 3.56 (s, 3H), 3.35-2.29 (m, 4H), 3.14-3.07 (m, 2H), 2.65-2.59 (m, 3H), 2.43-2.38 (m, 1H), 2.10-2.05 to (m, 1H). LCMS R$_T$=0.743 min, m/z=451.1 [M+H]$^+$. LCMS (5 to 95% acetonitrile in water+0.1% formic acid over 1.5 mins) retention time 0.743 min, ESI+ found [M+H]=451.1.

Examples 14-23

Prepared According to the Methods Provided Below

Method #14

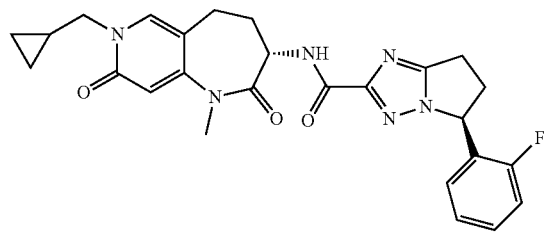 [SMILES: CN1C(=O)[C@@H](NC(=O)c2nc3n(n2)[C@H](c2ccccc2F)CC3)CCc2cn(CC3CC3)c(=O)cc21]

(5S)-5-(2-fluorophenyl)-N-[(3S)-7-(cyclopropylmethyl)-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide

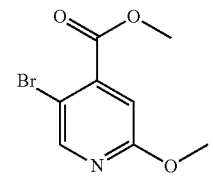

Step 1: methyl 5-bromo-2-methoxy-pyridine-4-carboxylate

To a solution of methyl 5-bromo-2-hydroxy-pyridine-4-carboxylate (20.0 g, 86.2 mmol) in toluene (200 mL) was added silver carbonate (30.9 g, 112.1 mmol) and iodomethane (18.4 g, 129.3 mmol). The reaction mixture was stirred at 50° C. for 15 h and filtered. The filtrate was concentrated under reduced pressure. The residue was purified by column chromatography (silica gel, 100-200 mesh, 0 to 30% ethyl acetate in petroleum ether) to give methyl 5-bromo-2-methoxy-pyridine-4-carboxylate (16.4 g, 77%) as a white solid, used as is in the next step.

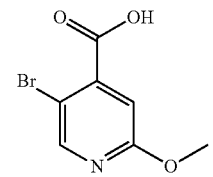

Step 2: 5-bromo-2-methoxy-pyridine-4-carboxylic Acid

A mixture of lithium hydroxide monohydrate (13.98 g, 333.25 mmol) and methyl 5-bromo-2-methoxy-pyridine-4-carboxylate (16.40 g, 66.65 mmol) in tetrahydrofuran (30 mL)/water (6 mL) was stirred at 25° C. for 2 h. The mixture was concentrated under reduced pressure. The aqueous residue was diluted with water (10 mL) and adjusted to pH=4 by addition of hydrochloric acid (2 M, 80 mL). The mixture was extracted with ethyl acetate (3×10 mL). The combined organic layers were dried over sodium sulfate and concentrated under reduced pressure to afford crude 5-bromo-2-methoxy-pyridine-4-carboxylic acid (9.62 g, to 62%) as brown oil. LCMS R$_T$=0.448 min, m/z=231.9 [M+H]$^+$.

LCMS (5 to 95% acetonitrile in water+0.03% trifluoacetic acid over 1.5 mins) retention time 0.448 min, ESI+ found [M+H]=231.9.

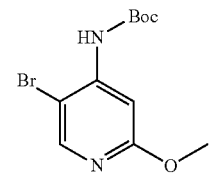 [SMILES: COc1cc(NC(=O)OC(C)(C)C)c(Br)cn1]

Step 3: tert-butyl N-(5-bromo-2-methoxy-4-pyridyl)carbamate

Diphenyl phosphoryl azide (655 mg, 2.37 mmol) was slowly added a solution of 5-bromo-2-methoxy-pyridine-4-carboxylic acid (8.4 g, 36.2 mmol) and triethylamine (3.7 g, 36.2 mmol) in 2-butanol (90 mL) at 80° C. After addition, the mixture was heated to reflux for 12 h and then added slowly to ice water (200 mL). The resulting mixture was extracted with dichloromethane (3×200 mL). The combined organic layers were dried over sodium sulfate and concentrated under reduced pressure. The residue was purified by column chromatography (silica gel, 100-200 mesh, 0 to 30% ethyl acetate in petroleum ether) to give tert-butyl N-(5-bromo-2-methoxy-4-pyridyl)carbamate (6.90 g, 63%) as a pale yellow solid, used as is in the next step.

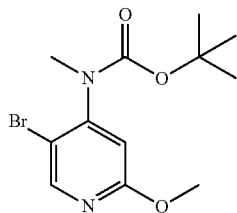 [SMILES: COc1cc(N(C)C(=O)OC(C)(C)C)c(Br)cn1]

Step 4: tert-butyl N-(5-bromo-2-methoxy-4-pyridyl)-N-methyl-carbamate

To a solution of tert-butyl N-(5-bromo-2-methoxy-4-pyridyl)carbamate (6.9 g, 22.76 mmol) in N,N-dimethylformamide (70 mL) was added cesium carbonate (14.8 g, 45.52 mmol) and iodomethane (3.9 g, 37.31 mmol). The reaction mixture was stirred at 25° C. for 2 h and then diluted with water (30 mL). The mixture was extracted with ethyl acetate (3×50 mL). The combined organic layers were washed with water (20 mL), brine (20 mL), dried over sodium sulfate and concentrated under reduced pressure. The residue was purified by column chromatography (silica gel, 100-200 mesh, 0 to 10% ethyl acetate in petroleum ether) to give tert-butyl N-(5-bromo-2-methoxy-4-pyridyl)-N-methyl-carbamate (6.5 g, 90%) as a white solid. LCMS: $R_T$=0.858 min, m/z=318.9 [M+H]$^+$.

LCMS (5 to 95% acetonitrile in water+0.03% trifluoacetic acid over 1.5 mins) retention time 0.858 min, ESI+ found [M+H]=318.9.

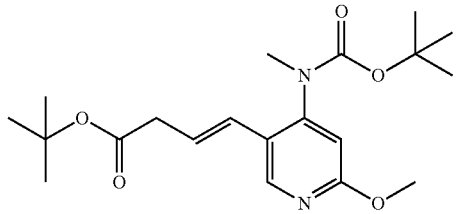 [SMILES: COc1cc(N(C)C(=O)OC(C)(C)C)c(/C=C/CC(=O)OC(C)(C)C)cn1]

Step 5: tert-butyl (E)-4-[4-[tert-butoxycarbonyl(methyl)amino]-6-methoxy-3-pyridyl]but-3-enoate A mixture of tert-butyl N-(5-bromo-2-methoxy-4-pyridyl)-N-methyl-carbamate (6.4 g, 20.18 mmol), tert-butyl-3-butenoate (5.7 g, 40.36 mmol), bis(tri-tert-butylphosphine)palladium(0) (1.2 g, 2.28 mmol) and N,N-diisopropylethylamine (10.0 mL, 60.53 mmol) in N,N-dimethylformamide (80 mL) was heated at 130° C. for 19 h under nitrogen atmosphere. After cooled, the reaction was diluted with water (40 mL) and extracted with ethyl acetate (3×30 mL). The combined organic layers were washed with water (20 mL), brine (20 mL), dried over sodium sulfate and concentrated under reduced pressure. The residue was purified by column chromatography (silica gel, 100-200 mesh, 0 to 10% ethyl acetate in petroleum ether) to give tert-butyl (E)-4-[4-[tert-butoxycarbonyl(methyl)amino]-6-methoxy-3-pyridyl]but-3-enoate (4.8 g, 63%) as a white solid. LCMS $R_T$=0.920 min, m/z=379.1 [M+H]$^+$.

LCMS (5 to 95% acetonitrile in water+0.03% trifluoacetic acid over 1.5 mins) retention time 0.920 min, ESI+ found [M+H]=379.1.

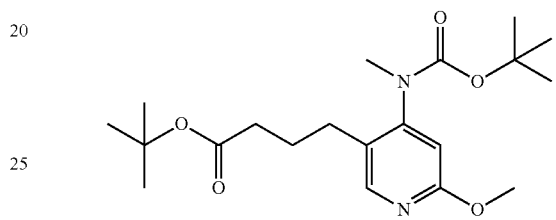

Step 6: tert-butyl 4-[4-[tert-butoxycarbonyl(methyl)amino]-6-methoxy-3-pyridyl]butanoate A mixture of tert-butyl (E)-4-[4-[tert-butoxycarbonyl(methyl)amino]-6-methoxy-3-pyridyl]but-3-enoate (4.8 g, 12.68 mmol) and Palladium (10% on carbon, 2.97 g) in ethyl acetate (200 mL) was hydrogenated (15 psi) at 25° C. for 5 h and filtered. The filtrate was concentrated under reduced pressure to afford crude tert-butyl 4-[4-[tert-butoxycarbonyl(methyl)amino]-6-methoxy-3-pyridyl]butanoate (4.4 g, 91%) as a white solid. LCMS $R_T$=0.903 min, m/z=381.0 [M+H]$^+$.

LCMS (5 to 95% acetonitrile in water+0.03% trifluoacetic acid over 1.5 mins) retention time 0.903 min, ESI+ found [M+H]=381.0.

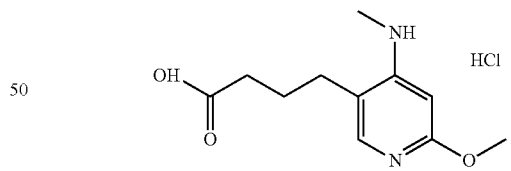

Step 7: 4-(6-methoxy-4-(methylamino)pyridin-3-yl)butanoic Acid hydrochloride To a solution of tert-butyl 4-[4-[tert-butoxycarbonyl(methyl)amino]-6-methoxy-3-pyridyl]butanoate (4.3 g, 11.3 mmol) in 1,4-dioxane (50 mL) was added hydrochloric acid (4 M in 1,4-dioxane, 50 mL, 200 mmol). The reaction mixture was stirred at 25° C. for 2 h and concentrated under reduced pressure to afford crude 4-(6-methoxy-4-(methylamino)pyridin-3-yl)butanoic acid hydrochloride (2.9 g, 100%) as a yellow oil.

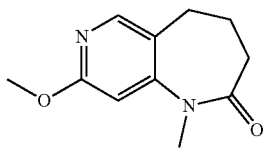

Step 8: 8-methoxy-1-methyl-4,5-dihydro-3H-pyrido[4,3-b]azepin-2-one

A mixture of 4-(6-methoxy-4-(methylamino)pyridin-3-yl)butanoic acid hydrochloride (2.90 g, 11.15 mmol) and 1-(3-dimethylaminopropyl)-3-ethylcarbodiimide hydrochloride (3.01 g, 15.75 mmol) in N,N-dimethylformamide (3 mL) was stirred at 25° C. for 15 h and then concentrated under reduced pressure. The residue was purified by column chromatography (silica gel, 100-200 mesh, 0 to 10% ethyl acetate in petroleum ether) to give 8-methoxy-1-methyl-4,5-dihydro-3H-pyrido[4,3-b]azepin-2-one (650 mg, 24%) as a white solid. LCMS $R_T$=0.533 min, m/z=207.0 [M+H]$^+$.

LCMS (5 to 95% acetonitrile in water+0.03% trifluoacetic acid over 1.5 mins) retention time 0.533 min, ESI+ found [M+H]=207.0.

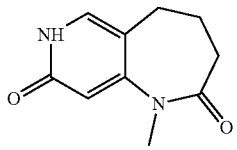

Step 9: 1-methyl-3,4,5,7-tetrahydropyrido[4,3-b]azepine-2,8-dione

To a solution of 8-methoxy-1-methyl-4,5-dihydro-3H-pyrido[4,3-b]azepin-2-one (550 mg, 2.67 mmol) in acetonitrile (6 mL) was added potassium iodide (1.77 g, 10.67 mmol) and chlorotrimethylsilane (1.16 g, 10.67 mmol). The reaction mixture was heated at 80° C. for 3 h and concentrated under reduced pressure to give the crude product. The residue was purified by column chromatography (silica gel, 100-200 mesh, 0 to 10% methyl alcohol in dichloromethane) to give 1-methyl-3,4,5,7-tetrahydropyrido[4,3-b]azepine-2,8-dione (475 mg, 93%) as a yellow oil. LCMS $R_T$=1.020 min, m/z=193.1 [M+H]$^+$.

LCMS (0 to 60% acetonitrile in water+0.03% ammonium bicarbonate over 3.0 mins) retention time 1.020 min, ESI+ found [M+H]=193.1.

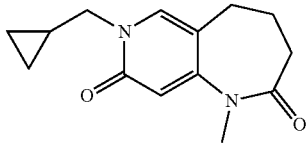 [SMILES: CN1C(=O)CCCc2cn(CC3CC3)c(=O)cc21]

Step 10: 7-(cyclopropylmethyl)-1-methyl-4,5-dihydro-1H-pyrido[4,3-b]azepine-2,8(3H,7H)-dione To a solution of 1-methyl-3,4,5,7-tetrahydropyrido[4,3-b]azepine-2,8-dione (200 mg, 1.04 mmol) in N,N-dimethylformamide (10 mL) was added potassium bis(trimethylsilyl)amide (1 M in tetrahydrofuran, 1.25 mL, 1.25 mmol) and cyclopropylmethyl bromide (169 mg, 1.25 mmol). The mixture was stirred at 25° C. for 16 h and then concentrated under reduced pressure. The residue was purified by column chromatography (silica gel, 100-200 mesh, 0 to 5% methyl alcohol in dichloromethane) to afford 7-(cyclopropylmethyl)-1-methyl-4,5-dihydro-1H-pyrido[4,3-b]azepine-2,8(3H,7H)-dione (130 mg, 51%) as a white solid. LCMS $R_T$=0.776 min, m/z=247.3 [M+H]$^+$.

LCMS (10 to 80% acetonitrile in water+0.03% trifluoacetic acid over 2.0 mins) retention time 0.776 min, ESI+ found [M+H]=247.3.

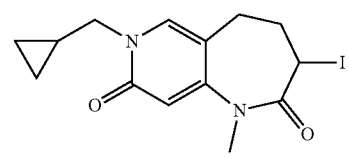 [SMILES: CN1C(=O)C(I)CCc2cn(CC3CC3)c(=O)cc21]

Step 11: 7-(cyclopropylmethyl)-3-iodo-1-methyl-4,5-dihydro-1H-pyrido[4,3-b]azepine-2,8(3H,7H)-dione To a solution of 7-(cyclopropylmethyl)-1-methyl-4,5-dihydro-3H-pyrido[4,3-b]azepine-2,8-dione (120 mg, 0.49 mmol) in dichloromethane (10 mL) was added $N^1,N^1,N^2,N^2$-tetramethylethane-1,2-diamine (1132 mg, 9.74 mmol) and iodotrimethylsilane (1170 mg, 5.85 mmol) at −15° C. The mixture was stirred at −15° C. for 1.5 h and iodine (742 mg, 2.92 mmol) was added. The resulting mixture was stirred for 3 h and quenched by addition of aqueous sodium thiosulfate (50%, 10 mL). The mixture was extracted with dichloromethane (3×20 mL). The combined organic layers were washed with brine (20 mL), dried over sodium sulfate and concentrated to afford 7-(cyclopropylmethyl)-3-iodo-1-methyl-4,5-dihydro-3H-pyrido[4,3-b]azepine-2,8-dione (100 mg, 55%) as a brown oil. LCMS $R_T$=0.933 min, m/z=373.2 [M+H]$^+$.

LCMS (10 to 80% acetonitrile in water+0.03% trifluoacetic acid over 2.0 mins) retention time 0.933 min, ESI+ found [M+H]=373.2.

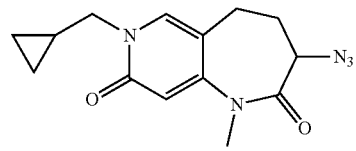 [SMILES: CN1C(=O)C(N=[N+]=[N-])CCc2cn(CC3CC3)c(=O)cc21]

Step 12: 3-azido-7-(cyclopropylmethyl)-1-methyl-4,5-dihydro-1H-pyrido[4,3-b]azepine-2,8(3H,7H)-dione A mixture of 7-(cyclopropylmethyl)-3-iodo-1-methyl-4,5-dihydro-3H-pyrido[4,3-b]azepine-2,8-dione (100 mg, 0.27 mmol) and sodium azide (35 mg, 0.54 mmol) in N,N-dimethylformamide (15 mL) was stirred at 25° C. for 12 h. The reaction mixture was diluted with water (10 mL) and extracted with dichloromethane (2×6 mL). The combined organic layers were dried over sodium sulfate and concentrated under reduced pressure to afford crude 7-azido- 1,5-dimethyl-8,9-dihydro-7H-pyrido[3,2-b]azepine-2,6-dione (70 mg, 91%) as a brown oil. LCMS R$_T$=0.532 min, m/z=288.0 [M+H]$^+$.

LCMS (5 to 95% acetonitrile in water+0.03% trifluoacetic acid over 1.5 mins) retention time 0.532 min, ESI+ found [M+H]=288.0.

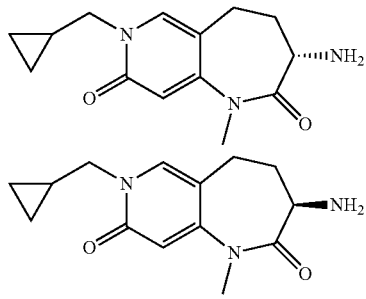

Step 13: (S)-3-amino-7-(cyclopropylmethyl)-1-methyl-4,5-dihydro-1H-pyrido[4,3-b]azepine-2,8 (3H,7H)-dione and (R)-3-amino-7-(cyclopropylmethyl)-1-methyl-4,5-dihydro-1H-pyrido[4,3-b]azepine-2,8(3H,7H)-dione To a solution of 7-azido-1,5-dimethyl-8,9-dihydro-7H-pyrido[3,2-b]azepine-2,6-dione (70 mg, 0.24 mmol) in tetrahydrofuran (10 mL) and water (2 mL) was added triphenylphosphine (128 mg, 0.49 mmol). The reaction mixture was stirred at 25° C. for 12 h and filtered. The filtrate was concentrated under reduced pressure. The residue was purified by preparative TLC (10% methanol in dichloromethane, R$_f$=0.2) to afford 3-amino-7-(cyclopropylmethyl)-1-methyl-4,5-dihydro-1H-pyrido[4,3-b]azepine-2,8(3H,7H)-dione (37 mg, 56%) as a white solid.

The racemate (37 mg, 0.14 mmol) was further separated by chiral SFC to afford arbitrarily assigned:

(3S)-3-amino-7-(cyclopropylmethyl)-1-methyl-4,5-dihydro-3H-pyrido[4,3-b]azepine-2,8-dione (peak 1, retention time=4.105 min) (18 mg, 49%) as a yellow oil. (3R)-3-amino-7-(cyclopropylmethyl)-1-methyl-4,5-dihydro-3H-pyrido[4,3-b]azepine-2,8-dione (peak 2, retention time=5.430 min) (19 mg, 51%) as a yellow oil.

SFC condition: Column Chiralcel OD-3 150×4.6 mm I.D., 3 um, Mobile phase: A: CO$_2$ B: ethanol (0.05% DEA), Gradient: from 5% to 40% of B in 5 min and hold 40% for 2.5 min, then 5% of B for 2.5 min, Flow rate: 2.5 mL/min Column temperature.: 35° C.

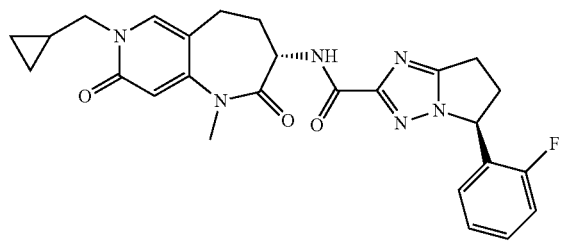 [SMILES: CN1C(=O)[C@@H](NC(=O)c2nc3n(n2)[C@H](c2ccccc2F)CC3)CCc2cn(CC3CC3)c(=O)cc21]

Step 14: (5S)-5-(2-fluorophenyl)-N-[(3S)-7-(cyclopropylmethyl)-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide A mixture of (5S)-5-(2-fluorophenyl)-6,7-dihydro-5H-pyrrolo[1,2-b][1,2,4]triazole-2-carboxylic acid (8.5 mg, 0.03 mmol), (3S)-3-amino-7-(cyclopropylmethyl)-1-methyl-4,5-dihydro-3H-pyrido[4,3-b]azepine-2,8-dione (10 mg, 0.03 mmol), 1-(3-dimethylaminopropyl)-3-ethylcarbodiimidehydrochloride (10 mg, 0.05 mmol) and 1-hydroxybenzotriazole (5 mg, 0.04 mmol) in N,N-dimethylformamide (2 mL) was stirred at 25° C. for 18 h. The mixture was concentrated under reduced pressure and the residue was purified by RP-HPLC (acetonitrile 26-56%/0.05% ammonium hydroxide in water) to afford arbitrarily assigned (5S)-5-(2-fluorophenyl)-N-[(3S)-7-(cyclopropylmethyl)-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide (7.3 mg, 44%) as a white solid. $^1$H NMR (400 MHz, CD$_3$OD) δ 7.67 (s, 1H), 7.41-7.36 (m, 1H), 7.22-7.13 (m, 3H), 6.46 (s, 1H), 5.80-5.74 (m, 1H), 4.68-4.63 (m, 1H), 3.87-3.82 (m, 2H), 3.36 (s, 3H), 3.30-3.26 (m, 1H), 3.13-3.06 (m, 2H), 2.70-2.61 (m, 3H), 2.44-2.41 (m, 1H), 2.10-2.07 (m, 1H), 1.33-1.30 (m, 1H), 0.62-0.56 (m, 2H), 0.48-0.43 (m, 2H). LCMS R$_T$=0.806 min, m/z=491.2 [M+H]$^+$.

LCMS (5 to 95% acetonitrile in water+0.1% formic acid over 1.5 mins) retention time 0.806 min, ESI+ found [M+H]= 491.2.

Method #15

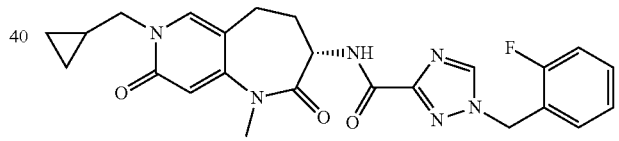

1-[(2-fluorophenyl)methyl]-N-[(3S)-7-(cyclopropylmethyl)-1-methyl-2,8-dioxo-4,5-dihydro-3H-pyrido[4,3-b]azepin-3-yl]-1,2,4-triazole-3-carboxamide Amide coupling was prepared in a similar fashion to Method #14. The crude was purified by RP-HPLC (acetonitrile 25-55%/0.05% ammonium hydroxide in water) to afford arbitrarily assigned 1-[(2-fluorophenyl)methyl]-N-[(3S)-7-(cyclopropylmethyl)-1-methyl-2,8-dioxo-4,5-dihydro-3H-pyrido[4,3-b]azepin-3-yl]-1,2,4-triazole-3-carboxamide (7.5 mg, 45%) as a white solid. $^1$H NMR (400 MHz, CD$_3$OD) δ 8.58 (s, 1H), 7.68 (s, 1H), 7.40-7.36 (m, 2H), 7.23-7.12 (m, 2H), 6.46 (s, 1H), 5.55 (s, 2H), 4.68-4.64 (m, 1H), 3.91-3.79 (m, 2H), 3.37 (s, 3H), 2.71-2.62 (m, 2H), 2.45-2.38 (m, 1H), 2.15-2.03 (m, 1H), 1.38-1.26 (m, 1H), 0.63-0.56 (m, 2H), 0.49-0.41 (m, 2H). LCMS R$_T$=0.782 min, m/z=465.1 [M+H]$^+$.

LCMS (5 to 95% acetonitrile in water+0.1% formic acid over 1.5 mins) retention time 0.782 min, ESI+ found [M+H]= 465.1.

Method #16

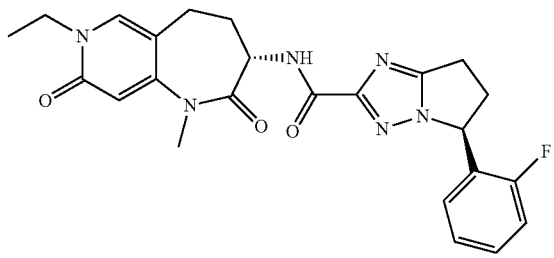 [SMILES: CCn1cc2c(cc1=O)N(C)C(=O)[C@@H](NC(=O)c1nc3n(n1)[C@H](c1ccccc1F)CC3)CC2]

(5S)-5-(2-fluorophenyl)-N-[(3S)-7-ethyl-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide

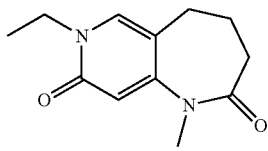 [SMILES: CCn1cc2c(cc1=O)N(C)C(=O)CCC2]

Step 1: 7-ethyl-1-methyl-4,5-dihydro-1H-pyrido[4,3-b]azepine-2,8(3H,7H)-dione

To a solution of 1-methyl-4,5-dihydro-1H-pyrido[4,3-b]azepine-2,8(3H,7H)-dione (100 mg, 0.52 mmol) in tetrahydrofuran (10 mL) was added potassium bis(trimethylsilyl)amide (1 M in tetrahydrofuran, 0.62 mL, 0.62 mmol) and iodoethane (97 mg, 0.62 mmol). The resulting mixture was stirred at 25° C. for 18 h and concentrated under reduced pressure. The residue was purified by column chromatography (silica gel, 100-200 mesh, 0 to 5% methanol in dichloromethane) to afford 7-ethyl-1-methyl-4,5-dihydro-1H-pyrido[4,3-b]azepine-2,8(3H,7H)-dione (71 mg, 62%) as a white solid, used as is in the next step.

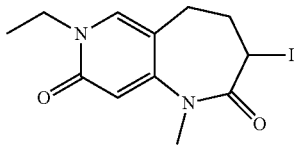 [SMILES: CCn1cc2c(cc1=O)N(C)C(=O)C(I)CC2]

Step 2: 7-ethyl-3-iodo-1-methyl-4,5-dihydro-1H-pyrido[4,3-b]azepine-2,8(3H,7H)-dione To a solution of 7-ethyl-1-methyl-4,5-dihydro-1H-pyrido[4,3-b]azepine-2,8(3H,7H)-dione (71 mg, 0.32 mmol) in dichloromethane (3 mL) was added $N^1,N^1,N^2,N^2$-tetramethylethane-1,2-diamine (456 mg, 3.92 mmol) and iodotrimethylsilane (654 mg, 3.27 mmol) at 0° C. under nitrogen atmosphere. The resulting mixture was stirred at 0° C. for 1 h and iodine (415 mg, 1.63 mmol) was added. The mixture was stirred at 0° C. for another 2 h and then quenched by addition of aqueous sodium thiosulfate (50%, 10 mL). The resulting mixture was extracted with dichloromethane (3×20 mL). The combined organic layers were washed with brine (20 mL), dried over sodium sulfate and concentrated under reduced pressure to afford crude 7-ethyl-3-iodo-1-methyl-4,5-dihydro-1H-pyrido[4,3-b]azepine-2,8(3H,7H)-dione (100 mg, 88%) as a brown oil, used as is in the next step.

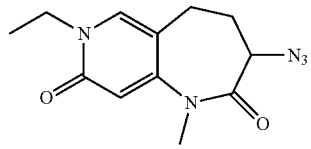 [SMILES: CCn1cc2c(cc1=O)N(C)C(=O)C(N=[N+]=[N-])CC2]

Step 3: 3-azido-7-ethyl-1-methyl-4,5-dihydro-1H-pyrido[4,3-b]azepine-2,8(3H,7H)-dione A mixture of 7-ethyl-3-iodo-1-methyl-4,5-dihydro-1H-pyrido[4,3-b]azepine-2,8(3H,7H)-dione (100 mg, 0.29 mmol) and sodium azide (38 mg, 0.58 mmol) in N,N-dimethylformamide (2 mL) was stirred at 25° C. for 6 h and then diluted with water (10 mL). The mixture was extracted with dichloromethane (2×6 mL). The combined organic layers were dried over sodium sulfate and concentrated under reduced pressure to afford crude 3-azido-7-ethyl-1-methyl-4,5-dihydro-1H-pyrido[4,3-b]azepine-2,8(3H,7H)-dione (70 mg, 93%) as a brown oil. LCMS $R_T$=0.722 min, m/z=266.2 [M+H]$^+$.

LCMS (10 to 80% acetonitrile in water+0.03% trifluoacetic acid over 2.0 mins) retention time 0.722 min, ESI+ found [M+H]=266.2.

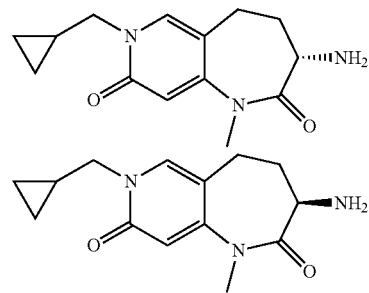

Step 4: (S)-3-amino-7-ethyl-1-methyl-4,5-dihydro-1H-pyrido[4,3-b]azepine-2,8(3H,7H)-dione and (R)-3-amino-7-ethyl-1-methyl-4,5-dihydro-1H-pyrido[4,3-b]azepine-2,8(3H,7H)-dione To a solution of 3-azido-7-ethyl-1-methyl-4,5-dihydro-1H-pyrido[4,3-b]azepine-2,8(3H,7H)-dione (70 mg, 0.27 mmol) in water (1 mL) and tetrahydrofuran (5 mL) was added triphenylphosphine (141 mg, 0.54 mmol). The reaction mixture was stirred at 25° C. for 18 h and then concentrated under reduced pressure. The residue was purified by preparative TLC (10% methanol in dichloromethane, $R_f$=0.2) to afford 3-amino-7-ethyl-1-methyl-4,5-dihydro-1H-pyrido[4,3-b]azepine-2,8(3H,7H)-dione (40 mg, 55%) as a brown oil.

The racemate (40 mg, 0.17 mmol) was further separated by chiral SFC to afford arbitrarily assigned:

(S)-3-amino-7-ethyl-1-methyl-4,5-dihydro-1H-pyrido[4,3-b]azepine-2,8(3H,7H)-dione (peak 1, retention time=2.846 min) (17 mg, 41%) as a yellow oil and (R)-3- amino-7-ethyl-1-methyl-4,5-dihydro-1H-pyrido[4,3-b]azepine-2,8(3H,7H)-dione (peak 2, retention time=4.009 min) (23 mg, 48%) as a yellow oil.

SFC condition: Column: Chiralcel OD-3 100×4.6 mm I.D., 3 μm, Mobile phase: A: CO2 B: ethanol (0.05% DEA), Gradient: from 5% to 40% of B in 4.5 min and hold 40% for 2.5 min, then 5% of B for 1 min, Flow rate: 2.8 mL/min, Column temperature: 40° C.

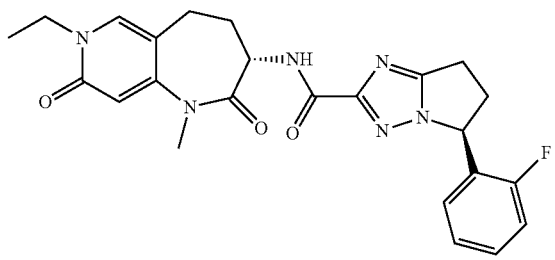 [SMILES: CCn1cc2c(cc1=O)N(C)C(=O)[C@@H](NC(=O)c1nc3n(n1)[C@H](c1ccccc1F)CC3)CC2]

Step 5: (5S)-5-(2-fluorophenyl)-N-[(3S)-7-ethyl-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide A mixture of (5S)-5-(2-fluorophenyl)-6,7-dihydro-5H-pyrrolo[1,2-b][1,2,4]triazole-2-carboxylic acid (9 mg, 0.04 mmol), (3S)-3-amino-7-ethyl-1-methyl-4,5-dihydro-3H-pyrido[4,3-b]azepine-2,8-dione (9 mg, 0.04 mmol), 1-(3-dimethylaminopropyl)-3-ethylcarbodiimidehydrochloride (11 mg, 0.05 mmol) and 1-hydroxybenzotriazole (5 mg, 0.04 mmol) in N,N-dimethylformamide (2 mL) was stirred at 25° C. for 18 h. The mixture was concentrated under reduced pressure and the residue was purified by RP-HPLC (acetonitrile 10-40%/0.05% ammonium hydroxide in water) to afford arbitrarily assigned (5S)-5-(2-fluorophenyl)-N-[(3S)-7-ethyl-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide (4.6 mg, 26%) as a white solid. $^1$H NMR (400 MHz, CD$_3$OD) δ 7.64 (s, 1H), 7.45-7.36 (m, 1H), 7.22-7.13 (m, 3H), 6.45 (s, 1H), 5.81-5.763 (m, 1H), 4.66-4.62 (m, 1H), 4.06-4.00 (m, 2H), 3.35 (s, 3H), 3.26 (s, 1H), 3.18-3.10 (m, 2H), 2.75-2.61 (m, 3H), 2.50-2.34 (m, 1H), 2.15-2.01 (m, 1H), 1.35 (t, J=7.2 Hz, 3H). LCMS RT=0.967 min, m/z=465.3 [M+H]+.

LCMS (10 to 80% acetonitrile in water+0.1% formic acid over 2.0 mins) retention time 0.967 min, ESI+ found [M+H]= 465.3.

Method #17

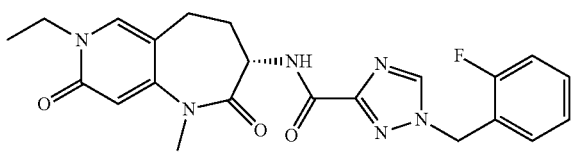 [SMILES: CCn1cc2c(cc1=O)N(C)C(=O)[C@@H](NC(=O)c1ncn(Cc3ccccc3F)n1)CC2]

1-[(2-fluorophenyl)methyl]-N-[(3S)-7-ethyl-1-methyl-2,8-dioxo-4,5-dihydro-3H-pyrido[4,3-b]azepin-3-yl]-1,2,4-triazole-3-carboxamide Amide coupling was prepared in a similar fashion to Method #16. The crude was purified by RP-HPLC (acetonitrile 20-50%/0.05% ammonium hydroxide in water) to afford arbitrarily assigned 1-[(2-fluorophenyl)methyl]-N-[(3S)-7-ethyl-1-methyl-2,8-dioxo-4,5-dihydro-3H-pyrido[4,3-b]azepin-3-yl]-1,2,4-triazole-3-carboxamide (1.92 mg, 12%) as a white solid. $^1$H NMR (400 MHz, CD$_3$OD) δ 8.58 (s, 1H), 7.64 (s, 1H), 7.44-7.34 (m, 2H), 7.23-7.11 (m, 2H), 6.45 (s, 1H), 5.55 (s, 2H), 4.66-4.63 (m, 1H), 4.06-4.01 (m, 2H), 3.36 (s, 3H), 2.70-2.60 (m, 2H), 2.51-2.35 (m, 1H), 2.15-1.97 (m, 1H), 1.36 (t, J=7.2 Hz, 3H). LCMS R$_T$=0.920 min, m/z=439.3 [M+H]$^+$.

LCMS (10 to 80% acetonitrile in water+0.1% formic acid over 2.0 mins) retention time 0.920 min, ESI+ found [M+H]= 439.3.

Method #18

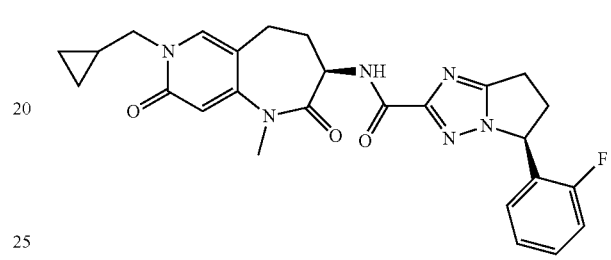

(5S)-5-(2-fluorophenyl)-N-[(3R)-7-(cyclopropylmethyl)-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide Amide coupling was prepared in a similar fashion to Method #14. The crude was purified by RP-HPLC (acetonitrile 25-55%/0.05% ammonium hydroxide in water) to afford arbitrarily assigned (5S)-5-(2-fluorophenyl)-N-[(3R)-7-(cyclopropylmethyl)-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide (6.2 mg, 33%) as a white solid. $^1$H NMR (400 MHz, CD$_3$OD) δ 7.67 (s, 1H), 7.44-7.37 (m, 1H), 7.22-7.13 (m, 3H), 6.46 (s, 1H), 5.79-5.76 (m, 1H), 4.68-4.63 (m, 1H), 3.89-3.82 (m, 2H), 3.36 (s, 3H), 3.30-3.25 (m, 1H), 3.19-3.05 (m, 2H), 2.74-2.59 (m, 3H), 2.48-2.37 (m, 1H), 2.08-2.06 (m, 1H), 1.35-1.26 (m, 1H), 0.61-0.55 (m, 2H), 0.50-0.42 (m, 2H). LCMS R$_T$=0.811 min, m/z=491.2 [M+H]$^+$.

LCMS (5 to 95% acetonitrile in water+0.1% formic acid over 1.5 mins) retention time 0.811 min, ESI+ found [M+H]= 491.2.

Method #19

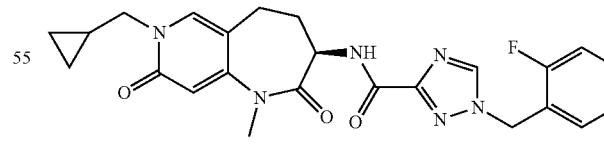

1-[(2-fluorophenyl)methyl]-N-[(3R)-7-(cyclopropylmethyl)-1-methyl-2,8-dioxo-4,5-dihydro-3H-pyrido[4,3-b]azepin-3-yl]-1,2,4-triazole-3-carboxamide Amide coupling was prepared in a similar fashion to Method #14. The crude was purified by RP-HPLC (acetonitrile 25-55%/0.05% ammonium hydroxide in water) to afford arbitrarily assigned 1-[(2-fluorophenyl)methyl]-N-[(3R)-7-(cyclopropylmethyl)-1-methyl-2,8-dioxo-4,5-dihydro-3H-pyrido[4,3-b]azepin-3-yl]-1,2,4-triazole-3-carboxamide (7.5 mg, 43%) as a white solid. $^1$H NMR (400 MHz, CD$_3$OD) δ 8.57 (s, 1H), 7.66 (s, 1H), 7.41-7.32 (m, 2H), 7.22-7.10 (m, 2H), 6.45 (s, 1H), 5.54 (s, 2H), 4.67-4.62 (m, 1H), 3.90-3.78 (m, 2H), 3.36 (s, 3H), 2.69-2.59 (m, 2H), 2.44-2.42 (m, 1H), 2.09-2.07 (m, 1H), 1.33-1.31 (m, 1H), 0.61-0.55 (m, 2H), 0.46-0.42 (m, 2H). LCMS R$_T$=0.789 min, m/z=465.1 [M+H]$^+$.

LCMS (5 to 95% acetonitrile in water+0.1% formic acid over 1.5 mins) retention time 0.789 min, ESI+ found [M+H]= 465.1.

Method #20

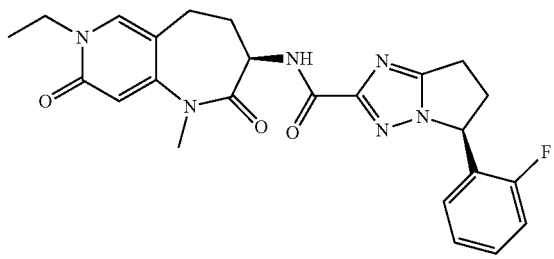 [SMILES: CCn1cc2c(cc1=O)N(C)C(=O)[C@H](NC(=O)c1nc3n(n1)[C@H](c1ccccc1F)CC3)CC2]

(5S)-5-(2-fluorophenyl)-N-[(3R)-7-ethyl-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide Amide coupling was prepared in a similar fashion to Method #16. The crude was purified by RP-HPLC (acetonitrile 20-50%/0.05% ammonium hydroxide in water) to afford arbitrarily assigned (5S)-5-(2-fluorophenyl)-N-[(3R)-7-ethyl-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide (3.6 mg, 20%) as a white solid. $^1$H NMR (400 MHz, CD$_3$OD) δ 7.63 (s, 1H), 7.44-7.35 (m, 1H), 7.22-7.14 (m, 3H), 6.44 (s, 1H), 5.82-5.74 (m, 1H), 4.66-4.62 (m, 1H), 4.06-4.00 (m, 2H), 3.36 (s, 3H), 3.30-3.26 (m, 1H), 3.20-3.03 (m, 2H), 2.75-2.61 (m, 3H), 2.49-2.36 (m, 1H), 2.13-2.01 (m, 1H), 1.35 (t, J=7.2 Hz, 3H). LCMS R$_T$=0.954 min, m/z=465.3 [M+H]$^+$.

LCMS (10 to 80% acetonitrile in water+0.1% formic acid over 2 mins) retention time 0.954 min, ESI+ found [M+H]= 465.3.

Method #21

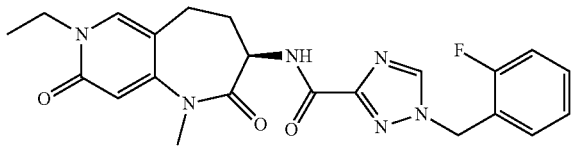 [SMILES: CCn1cc2c(cc1=O)N(C)C(=O)[C@H](NC(=O)c1ncn(Cc3ccccc3F)n1)CC2]

1-[(2-fluorophenyl)methyl]-N-[(3R)-7-ethyl-1-methyl-2,8-dioxo-4,5-dihydro-3H-pyrido[4,3-b]azepin-3-yl]-1,2,4-triazole-3-carboxamide Amide coupling was prepared in a similar fashion to Method #16. The crude was purified by RP-HPLC (acetonitrile 25-55%/0.05% ammonium hydroxide in water) to afford arbitrarily assigned 1-[(2-fluorophenyl)methyl]-N-[(3R)-7-ethyl-1-methyl-2,8-dioxo-4,5-dihydro-3H-pyrido[4,3-b]azepin-3-yl]-1,2,4-triazole-3-carboxamide (7.55 mg, 46%) as a white solid. $^1$H NMR (400 MHz, CD$_3$OD) δ 8.56 (s, 1H), 7.62 (s, 1H), 7.41-7.33 (m, 2H), 7.20-7.10 (m, 2H), 6.43 (s, 1H), 5.53 (s, 2H), 4.64-4.61 (m, 1H), 4.04-3.98 (m, 2H), 3.34 (s, 3H), 2.68-2.57 (m, 2H), 2.47-2.36 (m, 1H), 2.11-2.02 (m, 1H), 1.35-1.33 (t, J=7.2 Hz, 3H). LCMS R$_T$=0.917 min, m/z=439.3 [M+H]$^+$.

LCMS (10 to 80% acetonitrile in water+0.1% formic acid over 2.0 mins) retention time 0.917 min, ESI+ found [M+H]= 439.3.

Example 24

RIP1 Kinase Inhibition Assays (Biochemical Assay)

The compounds of the present invention were tested for their capacity to inhibit RIP1K activity as described below.

Enzyme assay: The ability of the receptor interacting protein kinase (RIPK1) to catalyze the hydrolysis of adenosine-5'-triphosphate (ATP) is monitored using the Transcreener ADP (adenosine-5'-diphosphate) assay (BellBrook Labs). Purified human RIP1 kinase domain (2-375) (50 nM) derived from a baculovirus-infected insect cell expression system is incubated with test compounds for 2 hours in 50 mM Hepes buffer (pH 7.5) containing 30 mM MgCl$_2$, 1 mM dithiothreitol, 50 μM ATP, 0.002% Brij-35, and 0.5% dimethyl sulfoxide (DMSO). Reactions are quenched by the addition of 1× Bell Brooks Stop buffer B (20 mM Hepes (ph 7.5), 40 mM ethylenediaminetetraacetic acid and 0.02% Brij-35) containing an additional 12 mM EDTA and 55 μg/mL ADP2 antibody and 4 nM ADP-AlexaFluor® 633 tracer. The tracer bound to the antibody is displaced by the ADP generated during the RIP1K reaction, which causes a decrease in fluorescence polarization that is measured by laser excitation at 633 nm with a FP microplate reader M1000. Fractional activity was plotted against test article concentration. Using Genedata Screener software (Genedata; Basel, Switzerland), the data were fit to the tight-binding apparent inhibition constant (K$_i^{app}$) Morrison equation [Williams, J. W. and Morrison, J. F. (1979) The kinetics of reversible tight-binding inhibition. *Methods Enzymol* 63: 437-67]. The following equation was used to calculate fractional activity and K$_i^{app}$:

Fractional activity =

$$\frac{v_i}{v_o} = 1 - \frac{([E]_T + [I]_T + K_i^{app}) - \sqrt{([E]_T + [I]_T + K_i^{app})^2 - 4[E]_T[I]_T}}{2[E]_T}$$

where [E]$_T$ and [I]$_T$ are the total concentrations of active enzyme and test article, respectively.

Exemplary compounds of the present invention are provided in the following Tables along with their physiochemical characterization and in vitro RIP1 kinase inhibitory activity data. "Method" in the first column of each table refers to the synthetic method(s) used to prepare each compound as shown in the Examples above. In certain examples, chiral column retention times (min) are provided for certain stereoisomers.

TABLE 1

| Compound Example # Method | RIP1 Ki (μM) | Structure and Name | ¹H NMR Data | MS (m/z) |
|---|---|---|---|---|
| Example 1 Method #1 | 0.233 | (S)-1-benzyl-N-(1,5-dimethyl-2,6-dioxo-2,5,6,7,8,9-hexahydro-1H-pyrido[3,2-b]azepin-7-yl)-1H-1,2,4-triazole-3-carboxamide | ¹H NMR (400 MHz, CD$_3$OD) δ 8.56 (s, 1H), 7.58 (d, J = 9.6 Hz, 1H), 7.37-7.33 (m, 5H), 6.57 (d, J = 10.0 Hz, 1H), 5.47 (s, 2H), 4.67-4.62 (m, 1H), 3.68 (s, 3H), 3.29 (s, 3H), 3.10-3.05 (m, 1H), 2.88-2.86 (m, 1H), 2.75-2.72 (m, 1H), 2.27-2.22 (m, 1H). | 407.2 1.202 min |
| Example 2 Method #2 | 0.156 | (S)-N-(1,5-dimethyl-2,6-dioxo-2,5,6,7,8,9-hexahydro-1H-pyrido[3,2-b]azepin-7-yl)-1-(2-fluorobenzyl)-1H-1,2,4-triazole-3-carboxamide | ¹H NMR (400 MHz, CD$_3$OD) δ 8.58 (s, 1H), 7.58 (d, J = 10.0 Hz, 1H), 7.40-7.36 (m, 2H), 7.22-7.15 (m, 2H), 6.57 (d, J = 9.6 Hz, 1H), 5.55 (s, 2H), 4.66-4.62 (m, 1H), 3.68 (s, 3H), 3.28 (s, 3H), 3.08-3.04 (m, 1H), 2.88-2.84 (m, 1H), 2.74-2.71 (m, 1H), 2.24-2.21 (m, 1H). | 425.0 0.710 min |
| Example 3 Method #3 | 0.489 | 1-benzyl-N-[(3S)-1-methyl-2,7-dioxo-4,5-dihydro-3H-pyrido[1,2-a][1,3]diazepin-3-yl]-1,2,4-triazole-3-carboxamide | ¹H NMR (400 MHz, CD$_3$OD) δ 8.57 (s, 1H), 7.64-7.56 (m, 1H), 7.47-7.25 (m, 5H), 6.53 (d, J = 9.2 Hz, 1H), 6.46 (d, J = 7.2 Hz, 1H), 5.47 (s, 2H), 5.07-5.03 (m, 1H), 4.61-4.55 (m, 1H), 3.71-3.63 (m, 1H), 3.39 (s, 3H), 2.68-2.60 (m, 1H), 2.19-2.12 (m, 1H). | 393.2 1.177 min |
| Example 4 Method #4 | 0.290 | 1-[(2-fluorophenyl)methyl]-N-[(3S)-1-methyl-2,7-dioxo-4,5-dihydro-3H-pyrido[1,2-a][1,3]diazepin-3-yl]-1,2,4-triazole-3-carboxamide | ¹H NMR (400 MHz, CD$_3$OD) δ 8.58 (s, 1H), 7.62-7.57 (m, 1H), 7.44-7.34 (m, 2H), 7.22-7.12 (m, 2H), 6.52 (d, J = 9.2 Hz, 1H), 6.45 (d, J = 7.6 Hz, 1H), 5.55 (s, 2H), 5.06-5.01 (m, 1H), 4.60-4.55 (m, 1H), 3.69-3.62 (m, 1H), 3.39 (s, 3H), 2.67-2.59 (m, 1H), 2.19-2.11 (m, 1H). | 411.1 1.201 min |
| Example 5 Method #5 | 0.079 | 1-benzyl-N-[(3S)-1,7-dimethyl-2,8-dioxo-4,5-dihydro-3H-pyrido[4,3-b]azepin-3-yl]-1,2,4-triazole-3-carboxamide | ¹H NMR (400 MHz, CD$_3$OD) δ 8.57 (s, 1H), 7.63 (s, 1H), 7.38-7.32 (m, 5H), 6.46 (s, 1H), 5.47 (s, 2H), 4.64-4.59 (m, 1H), 3.57 (s, 3H), 3.36 (s, 3H), 2.67-2.61 (m, 2H), 2.45-2.41 (m, 1H), 2.10-2.06 (m, 1H). | 407.1 0.582 min |

TABLE 1-continued

| Compound Example # Method | RIP1 Ki (μM) | Structure and Name | ¹H NMR Data | MS (m/z) |
|---|---|---|---|---|
| Example 6 Method #6 | 0.049 | 1-[(2-fluorophenyl)methyl]-N-[(3S)-1,7-dimethyl-2,8-dioxo-4,5-dihydro-3H-pyrido[4,3-b]azepin-3-yl]-1,2,4-triazole-3-carboxamide | ¹H NMR (400 MHz, CD$_3$OD) δ 8.58 (s, 1H), 7.63 (s, 1H), 7.41-7.36 (m, 2H), 7.22-7.15 (m, 2H), 6.46 (s, 1H), 5.55 (s, 2H), 4.64-4.59 (m, 1H), 3.57 (s, 3H), 3.36 (s, 3H), 2.67-2.61 (m, 2H), 2.45-2.41 (m, 1H), 2.10-2.06 (m, 1H). | 425.0 0.587 min, |
| Example 7 Method #7 | 0.173 | (S)-1-benzyl-N-(1,8-dimethyl-2,7-dioxo-2,3,4,5,7,8-hexahydro-1H-pyrido[3,4-b]azepin-3-yl)-1H-1,2,4-triazole-3-carboxamide | ¹H NMR (400 MHz, CD$_3$OD) 8.56 (s, 1H), 7.87 (s, 1H), 7.37-7.33 (m, 5H), 6.49 (s, 1H), 5.46 (s, 2H), 4.71-4.65 (m, 1H), 3.59 (s, 3H), 3.32 (s, 3H), 2.74-2.68 (m, 2H), 2.45-2.38 (m, 1H), 2.13-2.08 (m, 1H). | 407.1 0.697 min |
| Example 8 Method #8 | >10 | (R)-1-benzyl-N-(1,8-dimethyl-2,7-dioxo-2,3,4,5,7,8-hexahydro-1H-pyrido[3,4-b]azepin-3-yl)-1H-1,2,4-triazole-3-carboxamide | ¹H NMR (400 MHz, CD$_3$OD) 8.56 (s, 1H), 7.87 (s, 1H), 7.37-7.33 (m, 5H), 6.49 (s, 1H), 5.47 (s, 2H), 4.71-4.65 (m, 1H), 3.59 (s, 3H), 3.33 (s, 3H), 2.74-2.69 (m, 2H), 2.45-2.38 (m, 1H), 2.13-2.08 (m, 1H). | 407.1 0.702 min |
| Example 9 Method #9 | 0.111 | (S)-N-(1,8-dimethyl-2,7-dioxo-2,3,4,5,7,8-hexahydro-1H-pyrido[3,4-b]azepin-3-yl)-1-(2-fluorobenzyl)-1H-1,2,4-triazole-3-carboxamide | ¹H NMR (400 MHz, CD$_3$OD) 8.57 (s, 1H), 7.87 (s, 1H), 7.40-7.35 (m, 2H), 7.21-7.14 (m, 2H), 6.49 (s, 1H), 5.45 (s, 2H), 4.71-4.65 (m, 1H), 3.59 (s, 3H), 3.32 (s, 3H), 2.74-2.69 (m, 2H), 2.45-2.38 (m, 1H), 2.13-2.08 (m, 1H). | 425.1 0.708 min |
| Example 10 Method #10 | >10 | (R)-N-(1,8-dimethyl-2,7-dioxo-2,3,4,5,7,8-hexahydro-1H-pyrido[3,4-b]azepin-3-yl)-1-(2-fluorobenzyl)-1H-1,2,4-triazole-3-carboxamide | ¹H NMR (400 MHz, CD$_3$OD) 8.57 (s, 1H), 7.87 (s, 1H), 7.40-7.35 (m, 2H), 7.21-7.14 (m, 2H), 6.49 (s, 1H), 5.45 (s, 2H), 4.71-4.65 (m, 1H), 3.59 (s, 3H), 3.32 (s, 3H), 2.74-2.69 (m, 2H), 2.45-2.38 (m, 1H), 2.13-2.08 (m, 1H). | 425.1 0.702 min |
| Example 11 Method #11 | 0.231 | (S)-N-((S)-1,8-dimethyl-2,7-dioxo-2,3,4,5,7,8-hexahydro-1H-pyrido[3,4-b]azepin-3-yl)-5-(2-fluorophenyl)-6,7-dihydro-5H-pyrrolo[1,2-b][1,2,4]triazole-2-carboxamide | ¹H NMR (400 MHz, CD$_3$OD) 7.87 (s, 1H), 7.43-7.39 (m, 1H), 7.20-7.13 (m, 3H), 6.49 (s, 1H), 5.79-5.75 (m, 1H), 4.69-4.64 (m, 1H), 3.59 (s, 3H), 3.35-3.29 (m, 4H), 3.14-3.07 (m, 2H), 2.74-2.68 (m, 3H), 2.42-2.36 (m, 1H), 2.13-2.07 (m, 1H). | 451.1 0.727 min |

TABLE 1-continued

| Compound Example # Method | RIP1 Ki (μM) | Structure and Name | 1H NMR Data | MS (m/z) |
|---|---|---|---|---|
| Example 12 Method #12 | >10 | 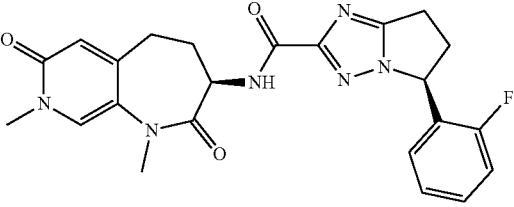<br>(S)-N-((R)-1,8-dimethyl-2,7-dioxo-2,3,4,5,7,8-hexahydro-1H-pyrido[3,4-b]azepin-3-yl)-5-(2-fluorophenyl)-6,7-dihydro-5H-pyrrolo[1,2-b][1,2,4]triazole-2-carboxamide | 1H NMR (400 MHz, CD3OD) 7.87 (s, 1H), 7.43-7.39 (m, 1H), 7.20-7.13 (m, 3H), 6.49 (s, 1H), 5.79-5.75 (m, 1H), 4.69-4.64 (m, 1H), 3.59 (s, 3H), 3.35-3.29 (m, 4H), 3.14-3.07 (m, 2H), 2.74-2.68 (m, 3H), 2.42-2.36 (m, 1H), 2.13-2.07 (m, 1H). | 451.1 0.729 min |
| Example 13 Method #13 | 0.0811 | 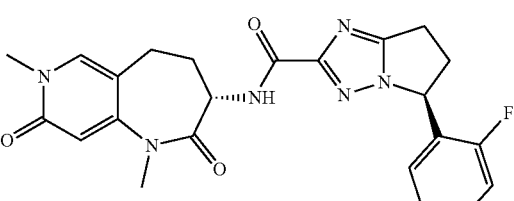<br>(5S)-5-(2-fluorophenyl)-N-[(3S)-1,7-dimethyl-2,8-dioxo-4,5-dihydro-3H-pyrido[4,3-b]azepin-3-yl]-6,7-dihydro-5H-pyrrolo[1,2-b][1,2,4]triazole-2-carboxamide | 1H NMR (400 MHz, CD3OD) 7.62 (s, 1H), 7.43-7.39 (m, 1H), 7.20-7.13 (m, 3H), 6.46 (s, 1H), 5.79-5.75 (m, 1H), 4.66-4.60 (m, 1H), 3.56 (s, 3H), 3.35-2.29 (m, 4H), 3.14-3.07 (m, 2H), 2.65-2.59 (m, 3H), 2.43-2.38 (m, 1H), 2.10-2.05 (m, 1H). | 451.1 0.743 min |
| Example 14 Method #14 | 0.056 | 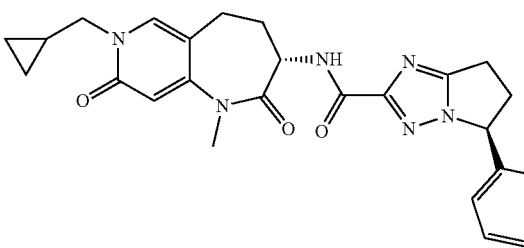<br>(5S)-5-(2-fluorophenyl)-N-[(3S)-7-(cyclopropylmethyl)-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide | 1H NMR (400 MHz, CD3OD) δ 7.67 (s, 1H), 7.41-7.36 (m, 1H), 7.22-7.13 (m, 3H), 6.46 (s, 1H), 5.80-5.74 (m, 1H), 4.68-4.63 (m, 1H), 3.87-3.82 (m, 2H), 3.36 (s, 3H), 3.30-3.26 (m, 1H), 3.13-3.06 (m, 2H), 2.70-2.61 (m, 3H), 2.44-2.41 (m, 1H), 2.10-2.07 (m, 1H), 1.33-1.30 (m, 1H), 0.62-0.56 (m, 2H), 0.48-0.43 (m, 2H). | 491.2 0.806 min |
| Example 15 Method #15 | 0.039 | 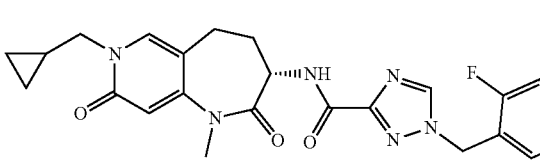<br>1-[(2-fluorophenyl)methyl]-N-[(3S)-7-(cyclopropylmethyl)-1-methyl-2,8-dioxo-4,5-dihydro-3H-pyrido[4,3-b]azepin-3-yl]-1,2,4-triazole-3-carboxamide | 1H NMR (400 MHz, CD3OD) δ 8.58 (s, 1H), 7.68 (s, 1H), 7.40-7.36 (m, 2H), 7.23-7.12 (m, 2H), 6.46 (s, 1H), 5.55 (s, 2H), 4.68-4.64 (m, 1H), 3.91-3.79 (m, 2H), 3.37 (s, 3H), 2.71-2.62 (m, 2H), 2.45-2.38 (m, 1H), 2.15-2.03 (m, 1H), 1.38-1.26 (m, 1H), 0.63-0.56 (m, 2H), 0.49-0.41 (m, 2H). | 465.1 0.782 min |
| Example 16 Method #18 | 6.9 | 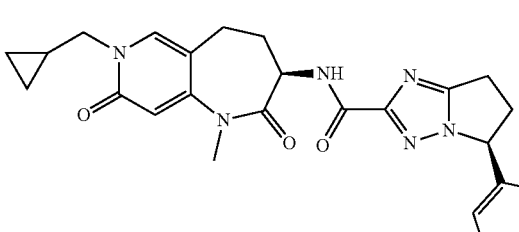<br>(5S)-5-(2-fluorophenyl)-N-[(3R)-7-(cyclopropylmethyl)-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide | 1H NMR (400 MHz, CD3OD) δ 7.67 (s, 1H), 7.44-7.37 (m, 1H), 7.22-7.13 (m, 3H), 6.46 (s, 1H), 5.79-5.76 (m, 1H), 4.68-4.63 (m, 1H), 3.89-3.82 (m, 2H), 3.36 (s, 3H), 3.30-3.25 (m, 1H), 3.19-3.05 (m, 2H), 2.74-2.59 (m, 3H), 2.48-2.37 (m, 1H), 2.08-2.06 (m, 1H), 1.35-1.26 (m, 1H), 0.61-0.55 (m, 2H), 0.50-0.42 (m, 2H). | 491.2 0.811 min |

TABLE 1-continued

| Compound Example # Method | RIP1 Ki (μM) | Structure and Name | ¹H NMR Data | MS (m/z) |
|---|---|---|---|---|
| Example 17 Method #19 | 6.9 | 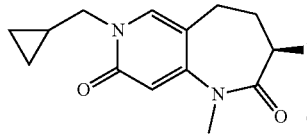<br>1-[(2-fluorophenyl)methyl]-N-[(3R)-7-(cyclopropylmethyl)-1-methyl-2,8-dioxo-4,5-dihydro-3H-pyrido[4,3-b]azepin-3-yl]-1,2,4-triazole-3-carboxamide | ¹H NMR (400 MHz, CD₃OD) δ 8.57 (s, 1H), 7.66 (s, 1H), 7.41-7.32 (m, 2H), 7.22-7.10 (m, 2H), 6.45 (s, 1H), 5.54 (s, 2H), 4.67-4.62 (m, 1H), 3.90-3.78 (m, 2H), 3.36 (s, 3H), 2.69-2.59 (m, 2H), 2.44-2.42 (m, 1H), 2.09-2.07 (m, 1H), 1.33-1.31 (m, 1H), 0.61-0.55 (m, 2H), 0.46-0.42 (m, 2H). | 465.1 0.789 min |
| Example 18 Method #16 | 0.11 | 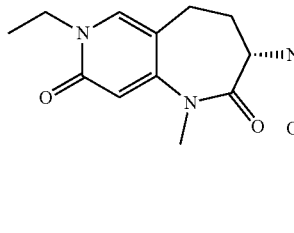<br>(5S)-5-(2-fluorophenyl)-N-[(3S)-7-ethyl-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide | ¹H NMR (400 MHz, CD₃OD) δ 7.64 (s, 1H), 7.45-7.36 (m, 1H), 7.22-7.13 (m, 3H), 6.45 (s, 1H), 5.81-5.763 (m, 1H), 4.66-4.62 (m, 1H), 4.06-4.00 (m, 2H), 3.35 (s, 3H), 3.26 (s, 1H), 3.18-3.10 (m, 2H), 2.75-2.61 (m, 3H), 2.50-2.34 (m, 1H), 2.15-2.01 (m, 1H), 1.35 (t, J = 7.2 Hz, 3H). | 465.3 0.967 min |
| Example 19 Method #17 | 0.11 | 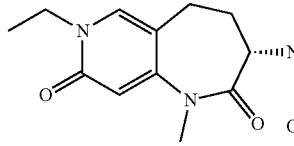<br>1-[(2-fluorophenyl)methyl]-N-[(3S)-7-ethyl-1-methyl-2,8-dioxo-4,5-dihydro-3H-pyrido[4,3-b]azepin-3-yl]-1,2,4-triazole-3-carboxamide | ¹H NMR (400 MHz, CD₃OD) δ 8.58 (s, 1H), 7.64 (s, 1H), 7.44-7.34 (m, 2H), 7.23-7.11 (m, 2H), 6.45 (s, 1H), 5.55 (s, 2H), 4.66-4.63 (m, 1H), 4.06-4.01 (m, 2H), 3.36 (s, 3H), 2.70-2.60 (m, 2H), 2.51-2.35 (m, 1H), 2.15-1.97 (m, 1H), 1.36 (t, J = 7.2 Hz, 3H). | 439.3 0.920 min |
| Example 20 Method #20 | >10 | 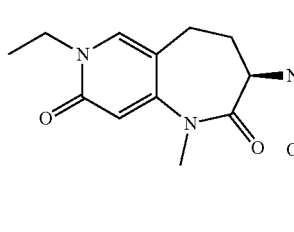<br>(5S)-5-(2-fluorophenyl)-N-[(3R)-7-ethyl-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide | ¹H NMR (400 MHz, CD₃OD) δ 7.63 (s, 1H), 7.44-7.35 (m, 1H), 7.22-7.14 (m, 3H), 6.44 (s, 1H), 5.82-5.74 (m, 1H), 4.66-4.62 (m, 1H), 4.06-4.00 (m, 2H), 3.36 (s, 3H), 3.30-3.26 (m, 1H), 3.20-3.03 (m, 2H), 2.75-2.61 (m, 3H), 2.49-2.36 (m, 1H), 2.13-2.01 (m, 1H), 1.35 (t, J = 7.2 Hz, 3H). | 465.3 0.954 min, |
| Example 21 Method #21 | >10 | 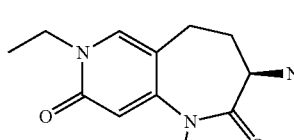<br>1-[(2-fluorophenyl)methyl]-N-[(3R)-7-ethyl-1-methyl-2,8-dioxo-4,5-dihydro-3H-pyrido[4,3-b]azepin-3-yl]-1,2,4-triazole-3-carboxamide | ¹H NMR (400 MHz, CD₃OD) δ 8.56 (s, 1H), 7.62 (s, 1H), 7.41-7.33 (m, 2H), 7.20-7.10 (m, 2H), 6.43 (s, 1H), 5.53 (s, 2H), 4.64-4.61 (m, 1H), 4.04-3.98 (m, 2H), 3.34 (s, 3H), 2.68-2.57 (m, 2H), 2.47-2.36 (m, 1H), 2.11-2.02 (m, 1H), 1.35-1.33 (t, J = 7.2 Hz, 3H). | 439.3 0.917 min, |

TABLE 1-continued

| Compound Example # Method | RIP1 Ki (μM) | Structure and Name | ¹H NMR Data | MS (m/z) |
|---|---|---|---|---|
| Example 22 Method #2 | >10 | 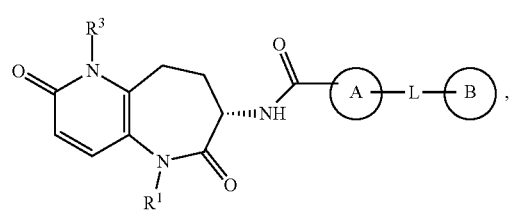  1-[(2-fluorophenyl)methyl]-N-[(7R)-1,5-dimethyl-2,6-dioxo-8,9-dihydro-7H-pyrido[3,2-b]azepin-7-yl]-1,2,4-triazole-3-carboxamide | ¹H NMR (400 MHz, CD₃OD) δ 8.58 (s, 1H), 7.58 (d, J = 9.6 Hz, 1H), 7.40-7.38 (m, 2H), 7.22-7.15 (m, 2H), 6.57 (d, J = 9.6 Hz, 1H), 5.55 (s, 2H), 4.66-4.62 (m, 1H), 3.68 (s, 3H), 3.28 (s, 3H), 3.08-3.04 (m, 1H), 2.88-2.84 (m, 1H), 2.74-2.71 (m, 1H), 2.23-2.22 (m, 1H). | 425.1 0.702 min |
| Example 23 Method #1 | >10 | 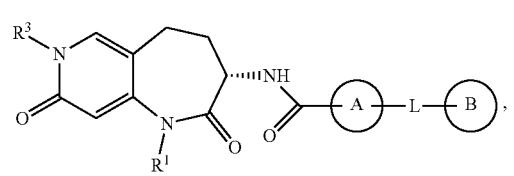  1-benzyl-N-[(7R)-1,5-dimethyl-2,6-dioxo-8,9-dihydro-7H-pyrido[3,2-b]azepin-7-yl]-1,2,4-triazole-3-carboxamide | ¹H NMR (400 MHz, CD₃OD) δ 8.56 (s, 1H), 7.58 (d, J = 10.0 Hz, 1H), 7.36-7.34 (m, 5H), 6.57 (d, J = 9.2 Hz, 1H), 5.47 (s, 2H), 4.67-4.62 (m, 1H), 3.68 (s, 3H), 3.29 (s, 3H), 3.06-3.05 (m, 1H), 2.88-2.84 (m, 1H), 2.75-2.72 (m, 1H), 2.27-2.22 (m, 1H). | 407.1 0.695 min |

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

I claim:

1. The compound of formula (Ia), (Ib), (Ic) or (Id):

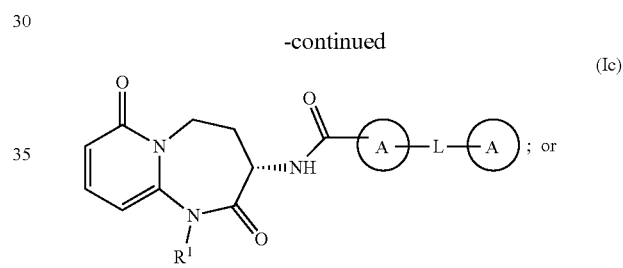

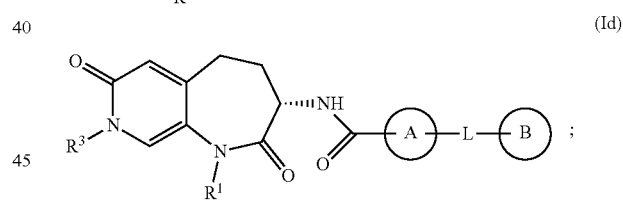

or a pharmaceutically acceptable salt thereof, wherein:
$R^1$ is selected from the group consisting of H, $C_1$-$C_4$ alkyl, and $C_1$-$C_4$ haloalkyl;
the A ring is tetrazolyl or a 5 or 6 membered heteroaryl having 1 to 3 heteroatoms selected from the group consisting of nitrogen, oxygen and sulfur; wherein the A ring is optionally substituted with 1 to 2 substituents selected from the group consisting of halogen, $C_1$-$C_4$ alkyl, $C_3$-$C_4$ cycloalkyl, $C_1$-$C_4$ haloalkyl, $C_1$-$C_4$ alkoxy, $C_1$-$C_4$ haloalkoxy and cyano; and wherein if a nitrogen atom in the A ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom;
the B ring is selected from the group consisting of phenyl, 5 or 6 membered heteroaryl, 3 to 7 membered cycloalkyl, and 4 to 7 membered heterocyclyl; wherein the B ring is optionally substituted with:
(a) 1 to 4 substituents selected from the group consisting of halogen, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, cyano, phenyl, benzyl, $CH_2$—($C_3$-$C_6$ cycloalkyl), and $CH_2CH_2$—($C_3$-$C_6$ cycloalkyl); wherein if a nitrogen atom in the C ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom;
(b) 1 to 2 substituents selected from the group consisting of $C_1$-$C_6$ alkyl, $C_1$-$C_6$ haloalkyl, $C_1$-$C_6$ alkoxy, $C_1$-$C_6$ haloalkoxy, $CH_2$-(4 to 6 membered heterocyclyl), $CH_2CH_2$-(4 to 6 membered heterocyclyl), and unsubstituted 5 or 6 membered heteroaryl; or
(c) two adjacent substituents which together form phenyl, 5 or 6 membered heteroaryl, 4 to 6 membered heterocyclyl or $C_4$-$C_6$ cycloalkyl;
L is selected from the group consisting of a bond, O, S, NH, $NCH_3$, $(CH_2)_m$, $CH(CH_3)$, $C(CH_3)_2$, $CF_2$, $CH_2O$, $CH_2S$, $CH(OH)$, $CH_2NH$, and $CH_2N(CH_3)$, or L is absent such that the A ring and the B ring are fused;
m is 1 or 2;
$R^3$ is selected from the group consisting of H, $C_1$-$C_6$ alkyl, $C_1$-$C_6$ haloalkyl, $C_1$-$C_6$ alkoxy, $C_3$-$C_6$ cycloalkyl, —$C(R^4)_2$—$C_3$-$C_6$ cycloalkyl, 4 to 6 membered heterocyclyl, and —$C(R^4)_2$-(4 to 6 membered heterocyclyl); and
each $R^4$ is independently selected from the group consisting of H, F, $C_1$-$C_6$ alkyl, $C_1$-$C_6$ alkoxy, and $C_1$-$C_6$ haloalkyl.

2. The compound of claim 1, or a pharmaceutically acceptable salt thereof, wherein $R^1$ is selected from the group consisting of H, methyl, ethyl, and isopropyl.

3. The compound of claim 1, or a pharmaceutically acceptable salt thereof, wherein $R^3$ is selected from the group consisting of H, methyl, ethyl, and —$CH_2$-cyclopropyl.

4. The compound of claim 1, or a pharmaceutically acceptable salt thereof, wherein L is $(CH_2)_m$ and m is 1 or 2.

5. The compound of claim 1, or a pharmaceutically acceptable salt thereof, wherein the A ring is a 5 or 6 membered heteroaryl having from 1 to 3 nitrogen atoms in the ring.

6. The compound of claim 1, or a pharmaceutically acceptable salt thereof, wherein L is $(CH_2)_m$; m is 1; and the B ring is phenyl substituted by 1 or 2 substituents selected from the group consisting of halogen, $C_1$-$C_4$ alkyl, and $C_1$-$C_4$ alkoxy.

7. The compound of claim 1, or a pharmaceutically acceptable salt thereof, wherein:
L is absent such that the A and B rings are fused;
the A ring is a 5 or 6 membered heteroaryl having from 1 to 3 nitrogen atoms in the ring; and
the B ring is a 5 to 7 membered heterocyclyl containing 0 to 1 heteroatoms selected from the group consisting of nitrogen, oxygen and sulfur.

8. The compound of claim 1, or a pharmaceutically acceptable salt thereof:

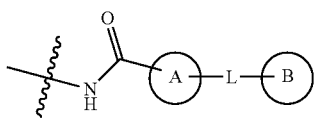

is selected from the group consisting of:

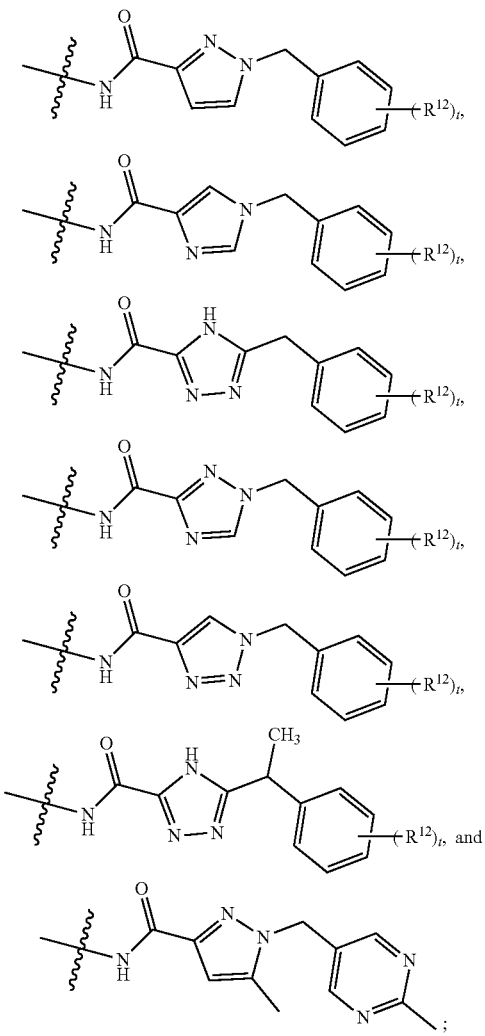

$R^{12}$ is selected from the group consisting of halogen and methyl; and
t is 0, 1 or 2.

9. The compound of claim 1, or a pharmaceutically acceptable salt thereof, wherein:

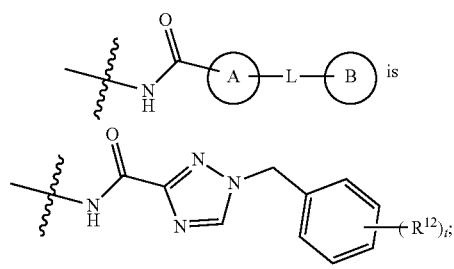

and
$R^{12}$ is fluoro and t is 0, 1 or 2.

10. The compound of claim 1, or a pharmaceutically acceptable salt thereof, wherein:

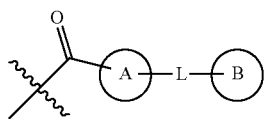

is selected from the group consisting of:

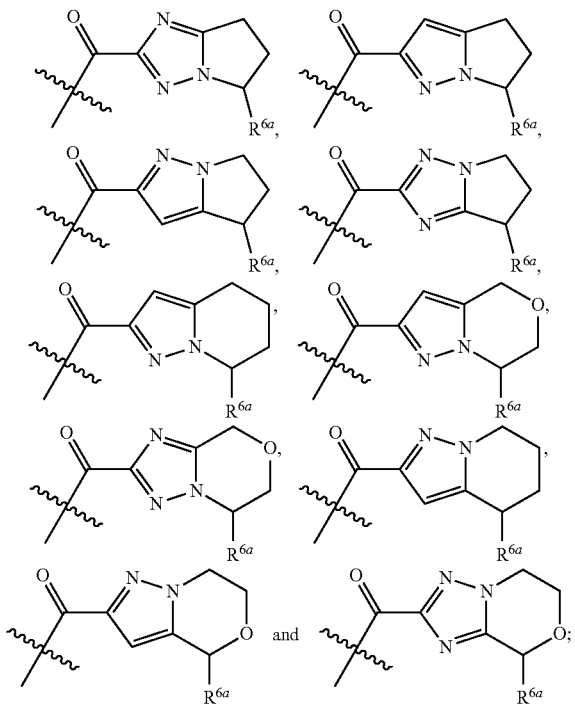

and

R$^{6a}$ is selected from the group consisting of H, C$_1$-C$_6$ alkyl, C$_3$-C$_6$ cycloalkyl, C$_1$-C$_6$ haloalkyl, phenyl and fluorophenyl.

11. The compound of claim 10, or a pharmaceutically acceptable salt thereof, wherein R$^{6a}$ is phenyl, flurophenyl, or difluorophenyl.

12. The compound of claim 8, wherein the compound is of formula (Ib):

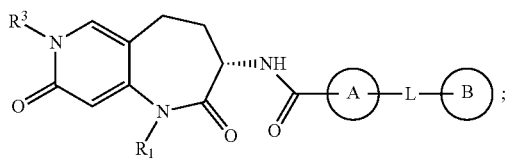

(Ib)

or a pharmaceutically acceptable salt thereof, wherein:

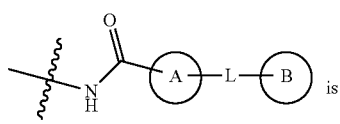

is

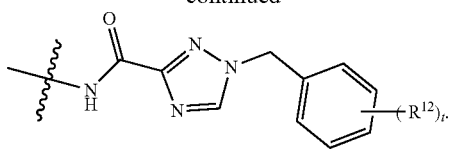

13. A compound selected from the group consisting of:

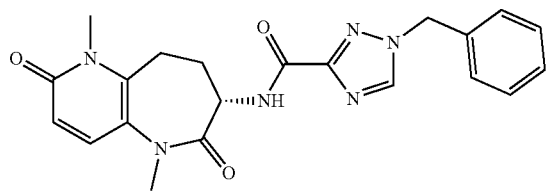 [SMILES: CN1C(=O)[C@@H](NC(=O)c2ncn(Cc3ccccc3)n2)CCc2c1ccc(=O)n2C]

1-benzyl-N-[(7S)-1,5-dimethyl-2,6-dioxo-8,9-dihydro-7H-pyrido[3,2-b]azepin-7-yl]-1,2,4-triazole-3-carboxamide;

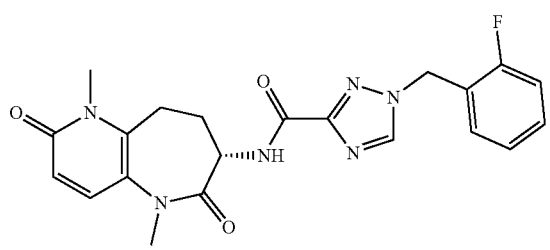 [SMILES: CN1C(=O)[C@@H](NC(=O)c2ncn(Cc3ccccc3F)n2)CCc2c1ccc(=O)n2C]

1-[(2-fluorophenyl)methyl]-N-[(7S)-1,5-dimethyl-2,6-dioxo-8,9-dihydro-7H-pyrido[3,2-b]azepin-7-yl]-1,2,4-triazole-3-carboxamide;

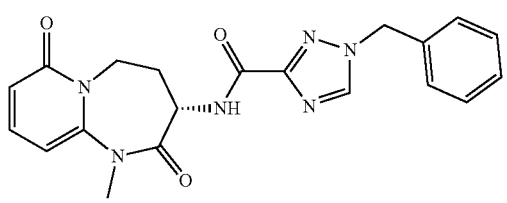 [SMILES: CN1C(=O)[C@@H](NC(=O)c2ncn(Cc3ccccc3)n2)CCn2c1cccc2=O]

1-benzyl-N-[(3S)-1-methyl-2,7-dioxo-4,5-dihydro-3H-pyrido[1,2-a][1,3]diazepin-3-yl]-1,2,4-triazole-3-carboxamide;

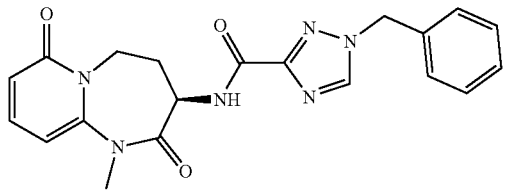 [SMILES: CN1C(=O)[C@H](NC(=O)c2ncn(Cc3ccccc3)n2)CCn2c1cccc2=O]

1-benzyl-N-[(3R)-1-methyl-2,7-dioxo-4,5-dihydro-3H-pyrido[1,2-a][1,3]diazepin-3-yl]-1,2,4-triazole-3-carboxamide;

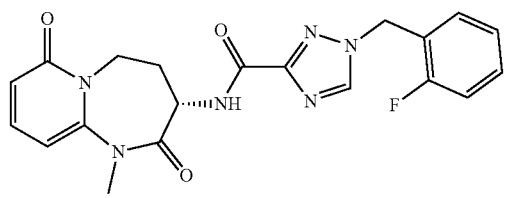 [SMILES: CN1C(=O)[C@@H](NC(=O)c2ncn(Cc3ccccc3F)n2)CCn2c1cccc2=O]

1-[(2-fluorophenyl)methyl]-N-[(3S)-1-methyl-2,7-dioxo-4,5-dihydro-3H-pyrido[1,2-a][1,3]diazepin-3-yl]-1,2,4-triazole-3-carboxamide;

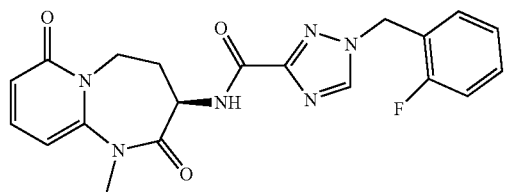 [SMILES: CN1C(=O)[C@H](NC(=O)c2ncn(Cc3ccccc3F)n2)CCn2c1cccc2=O]

1-[(2-fluorophenyl)methyl]-N-[(3R)-1-methyl-2,7-dioxo-4,5-dihydro-3H-pyrido[1,2-a][1,3]diazepin-3-yl]-1,2,4-triazole-3-carboxamide;

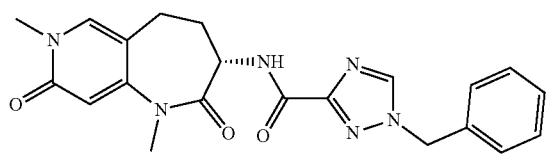 [SMILES: CN1C(=O)[C@@H](NC(=O)c2ncn(Cc3ccccc3)n2)CCc2cn(C)c(=O)cc21]

1-benzyl-N-[(3S)-1,7-dimethyl-2,8-dioxo-4,5-dihydro-3H-pyrido[4,3-b]azepin-3-yl]-1,2,4-triazole-3-carboxamide;

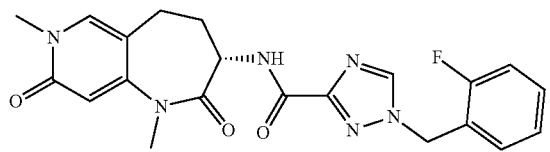 [SMILES: CN1C(=O)[C@@H](NC(=O)c2ncn(Cc3ccccc3F)n2)CCc2cn(C)c(=O)cc21]

1-[(2-fluorophenyl)methyl]-N-[(3S)-1,7-dimethyl-2,8-dioxo-4,5-dihydro-3H-pyrido[4,3-b]azepin-3-yl]-1,2,4-triazole-3-carboxamide;

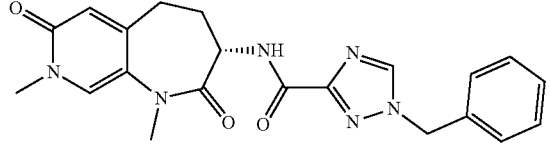 [SMILES: CN1C(=O)[C@@H](NC(=O)c2ncn(Cc3ccccc3)n2)CCc2cc(=O)n(C)cc21]

1-benzyl-N-[(3S)-1,8-dimethyl-2,7-dioxo-4,5-dihydro-3H-pyrido[3,4-b]azepin-3-yl]-1,2,4-triazole-3-carboxamide;

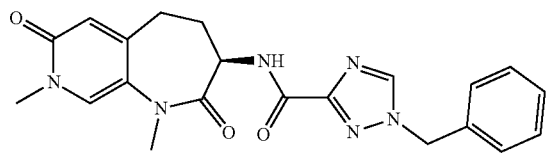 [SMILES: CN1C(=O)[C@H](NC(=O)c2ncn(Cc3ccccc3)n2)CCc2cc(=O)n(C)cc21]

1-benzyl-N-[(3R)-1,8-dimethyl-2,7-dioxo-4,5-dihydro-3H-pyrido[3,4-b]azepin-3-yl]-1,2,4-triazole-3-carboxamide;

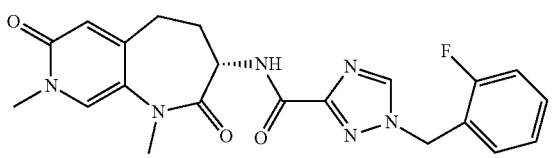 [SMILES: CN1C(=O)[C@@H](NC(=O)c2ncn(Cc3ccccc3F)n2)CCc2cc(=O)n(C)cc21]

(S)—N-(1,8-dimethyl-2,7-dioxo-2,3,4,5,7,8-hexahydro-1H-pyrido[3,4-b]azepin-3-yl)-1-(2-fluorobenzyl)-1H-1,2,4-triazole-3-carboxamide;

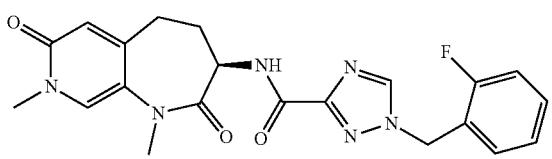 [SMILES: CN1C(=O)[C@H](NC(=O)c2ncn(Cc3ccccc3F)n2)CCc2cc(=O)n(C)cc21]

(R)—N-(1,8-dimethyl-2,7-dioxo-2,3,4,5,7,8-hexahydro-1H-pyrido[3,4-b]azepin-3-yl)-1-(2-fluorobenzyl)-1H-1,2,4-triazole-3-carboxamide;

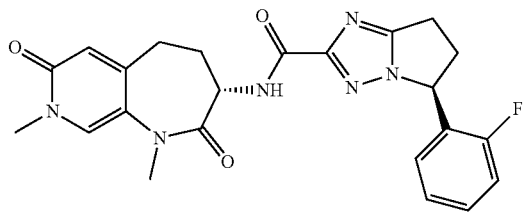 [SMILES: CN1C(=O)[C@@H](NC(=O)c2nc3n(n2)[C@H](c2ccccc2F)CC3)CCc2cc(=O)n(C)cc21]

(5S)-5-(2-fluorophenyl)-N-[(3S)-1,8-dimethyl-2,7-dioxo-4,5-dihydro-3H-pyrido[3,4-b]azepin-3-yl]-6,7-dihydro-5H-pyrrolo[1,2-b][1,2,4]triazole-2-carboxamide;

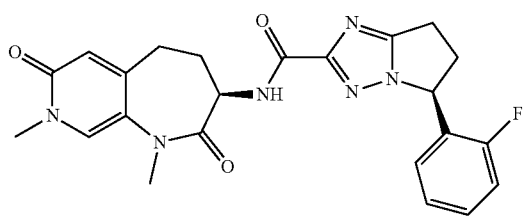 [SMILES: CN1C(=O)[C@H](NC(=O)c2nc3n(n2)[C@H](c2ccccc2F)CC3)CCc2cc(=O)n(C)cc21]

(5S)-5-(2-fluorophenyl)-N-[(3R)-1,8-dimethyl-2,7-dioxo-4,5-dihydro-3H-pyrido[3,4-b]azepin-3-yl]-6,7-dihydro-5H-pyrrolo[1,2-b][1,2,4]triazole-2-carboxamide;

101

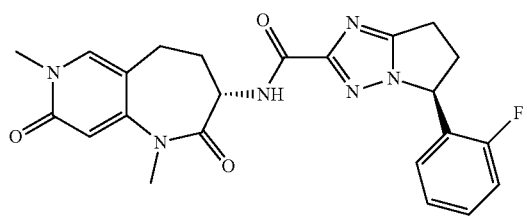 [SMILES: CN1C(=O)[C@@H](NC(=O)c2nc3n(n2)[C@H](c2ccccc2F)CC3)CCc2cn(C)c(=O)cc21]

(5S)-5-(2-fluorophenyl)-N-[(3S)-1,7-dimethyl-2,8-dioxo-4,5-dihydro-3H-pyrido[4,3-b]azepin-3-yl]-6,7-dihydro-5H-pyrrolo[1,2-b][1,2,4]triazole-2-carboxamide;

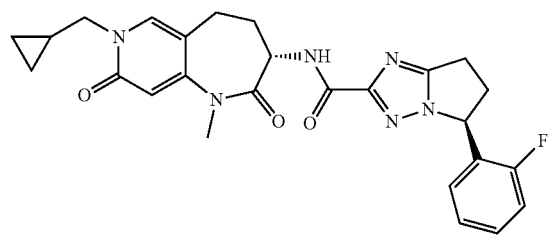 [SMILES: CN1C(=O)[C@@H](NC(=O)c2nc3n(n2)[C@H](c2ccccc2F)CC3)CCc2cn(CC3CC3)c(=O)cc21]

(5S)-5-(2-fluorophenyl)-N-[(3S)-7-(cyclopropylmethyl)-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide;

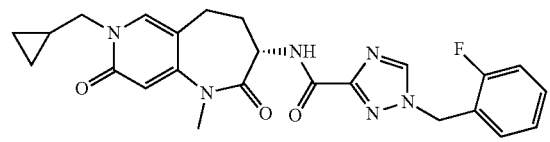 [SMILES: CN1C(=O)[C@@H](NC(=O)c2ncn(Cc3ccccc3F)n2)CCc2cn(CC3CC3)c(=O)cc21]

1-[(2-fluorophenyl)methyl]-N-[(3S)-7-(cyclopropylmethyl)-1-methyl-2,8-dioxo-4,5-dihydro-3H-pyrido[4,3-b]azepin-3-yl]-1,2,4-triazole-3-carboxamide;

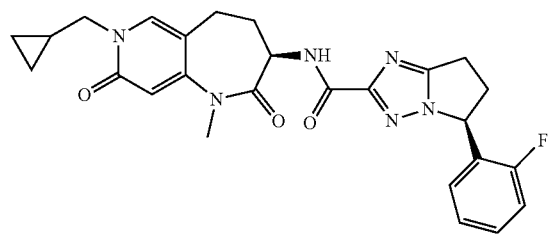 [SMILES: CN1C(=O)[C@H](NC(=O)c2nc3n(n2)[C@H](c2ccccc2F)CC3)CCc2cn(CC3CC3)c(=O)cc21]

(5S)-5-(2-fluorophenyl)-N-[(3R)-7-(cyclopropylmethyl)-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide;

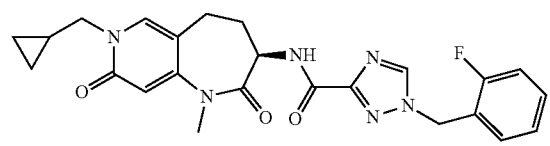 [SMILES: CN1C(=O)[C@H](NC(=O)c2ncn(Cc3ccccc3F)n2)CCc2cn(CC3CC3)c(=O)cc21]

102

1-[(2-fluorophenyl)methyl]-N-[(3R)-7-(cyclopropylmethyl)-1-methyl-2,8-dioxo-4,5-dihydro-3H-pyrido[4,3-b]azepin-3-yl]-1,2,4-triazole-3-carboxamide;

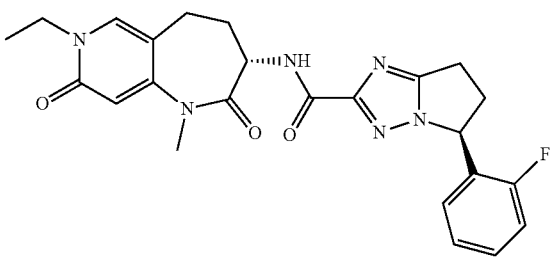 [SMILES: CCn1cc2c(cc1=O)N(C)C(=O)[C@@H](NC(=O)c1nc3n(n1)[C@H](c1ccccc1F)CC3)CC2]

(5S)-5-(2-fluorophenyl)-N-[(3S)-7-ethyl-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide;

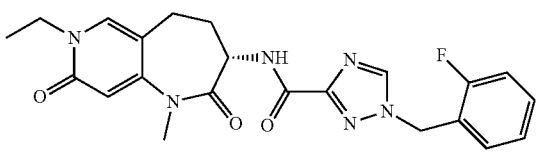 [SMILES: CCn1cc2c(cc1=O)N(C)C(=O)[C@@H](NC(=O)c1ncn(Cc3ccccc3F)n1)CC2]

1-[(2-fluorophenyl)methyl]-N-[(3S)-7-ethyl-1-methyl-2,8-dioxo-4,5-dihydro-3H-pyrido[4,3-b]azepin-3-yl]-1,2,4-triazole-3-carboxamide;

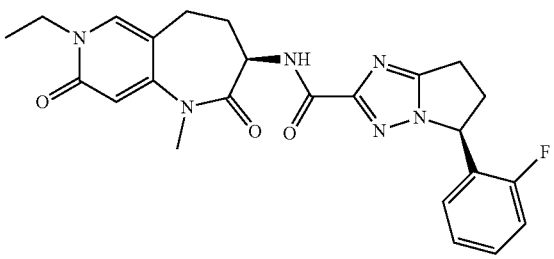 [SMILES: CCn1cc2c(cc1=O)N(C)C(=O)[C@H](NC(=O)c1nc3n(n1)[C@H](c1ccccc1F)CC3)CC2]

(5S)-5-(2-fluorophenyl)-N-[(3R)-7-ethyl-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide;

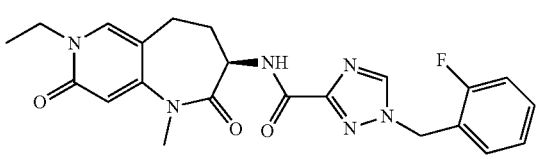 [SMILES: CCn1cc2c(cc1=O)N(C)C(=O)[C@H](NC(=O)c1ncn(Cc3ccccc3F)n1)CC2]

1-[(2-fluorophenyl)methyl]-N-[(3R)-7-ethyl-1-methyl-2,8-dioxo-4,5-dihydro-3H-pyrido[4,3-b]azepin-3-yl]-1,2,4-triazole-3-carboxamide;

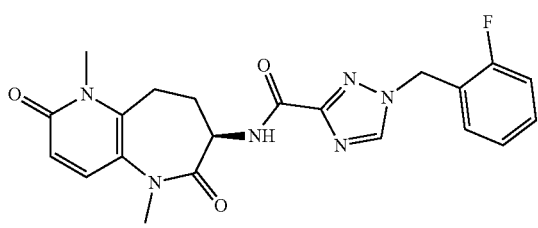 [SMILES: CN1C(=O)[C@H](NC(=O)c2ncn(Cc3ccccc3F)n2)CCc2c1ccc(=O)n2C]

1-[(2-fluorophenyl)methyl]-N-[(7R)-1,5-dimethyl-2,6-dioxo-8,9-dihydro-7H-pyrido[3,2-b]azepin-7-yl]-1,2,4-triazole-3-carboxamide; and

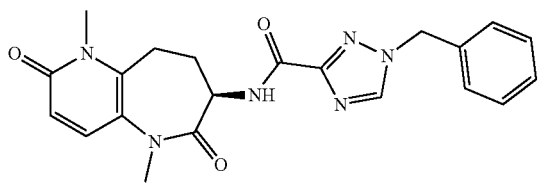 [SMILES: CN1C(=O)[C@H](NC(=O)c2ncn(Cc3ccccc3)n2)CCc2c1ccc(=O)n2C]

1-benzyl-N-[(7R)-1,5-dimethyl-2,6-dioxo-8,9-dihydro-7H-pyrido[3,2-b]azepin-7-yl]-1,2,4-triazole-3-carboxamide;

or a pharmaceutically acceptable salt thereof.

14. A pharmaceutical composition comprising a compound of claim 1, or a pharmaceutically acceptable salt thereof, and a therapeutically inert carrier.

15. The compound of claim 1, wherein the compound is:

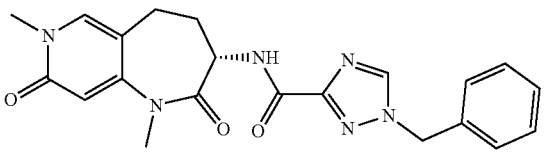 [SMILES: CN1C(=O)[C@@H](NC(=O)c2ncn(Cc3ccccc3)n2)CCc2cn(C)c(=O)cc21]

1-benzyl-N-[(3S)-1,7-dimethyl-2,8-dioxo-4,5-dihydro-3H-pyrido[4,3-b]azepin-3-yl]-1,2,4-triazole-3-carboxamide; or a pharmaceutically acceptable salt thereof.

16. The compound of claim 1, wherein the compound is:

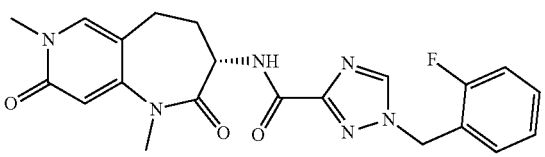 [SMILES: CN1C(=O)[C@@H](NC(=O)c2ncn(Cc3ccccc3F)n2)CCc2cn(C)c(=O)cc21]

1-[(2-fluorophenyl)methyl]-N-[(3S)-1,7-dimethyl-2,8-dioxo-4,5-dihydro-3H-pyrido[4,3-b]azepin-3-yl]-1,2,4-triazole-3-carboxamide; or a pharmaceutically acceptable salt thereof.

17. The compound of claim 1, wherein the compound is:

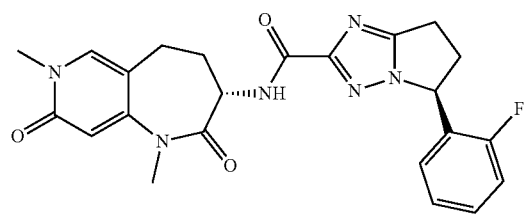 [SMILES: CN1C(=O)[C@@H](NC(=O)c2nc3n(n2)[C@H](c2ccccc2F)CC3)CCc2cn(C)c(=O)cc21]

(5S)-5-(2-fluorophenyl)-N-[(3S)-1,7-dimethyl-2,8-dioxo-4,5-dihydro-3H-pyrido[4,3-b]azepin-3-yl]-6,7-dihydro-5H-pyrrolo[1,2-b][1,2,4]triazole-2-carboxamide; or a pharmaceutically acceptable salt thereof.

18. The compound of claim 1, wherein the compound is:

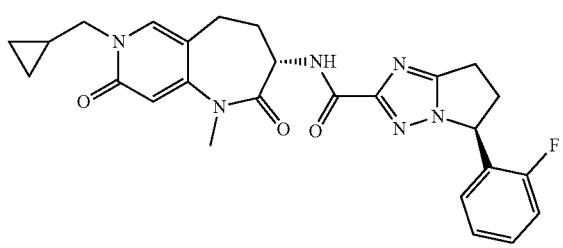 [SMILES: CN1C(=O)[C@@H](NC(=O)c2nc3n(n2)[C@H](c2ccccc2F)CC3)CCc2cn(CC3CC3)c(=O)cc21]

(5S)-5-(2-fluorophenyl)-N-[(3S)-7-(cyclopropylmethyl)-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide; or a pharmaceutically acceptable salt thereof.

19. The compound of claim 1, wherein the compound is:

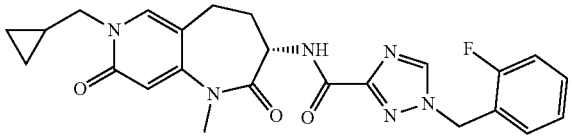 [SMILES: CN1C(=O)[C@@H](NC(=O)c2ncn(Cc3ccccc3F)n2)CCc2cn(CC3CC3)c(=O)cc21]

1-[(2-fluorophenyl)methyl]-N-[(3S)-7-(cyclopropylmethyl)-1-methyl-2,8-dioxo-4,5-dihydro-3H-pyrido[4,3-b]azepin-3-yl]-1,2,4-triazole-3-carboxamide; or a pharmaceutically acceptable salt thereof.

20. The compound of claim 1, wherein the compound is:

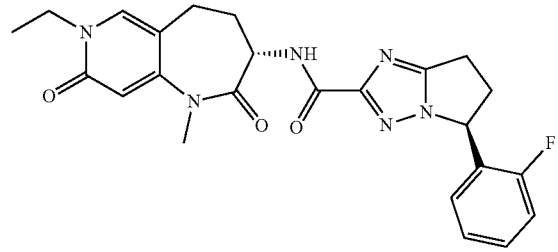 [SMILES: CCn1cc2c(cc1=O)N(C)C(=O)[C@@H](NC(=O)c1nc3n(n1)[C@H](c1ccccc1F)CC3)CC2]

(5S)-5-(2-fluorophenyl)-N-[(3S)-7-ethyl-1-methyl-2,8-dioxo-4,5-dihydro-3H-pyrido[4,3-b]azepin-3-yl]-6,7-dihydro-5H-pyrrolo[1,2-b][1,2,4]triazole-2-carboxamide; or a pharmaceutically acceptable salt thereof.

21. The compound of claim 1, wherein the compound is:

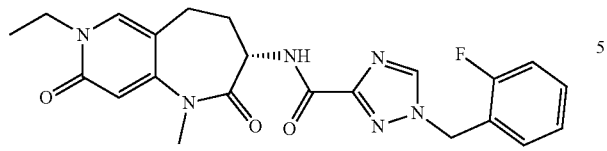

1-[(2-fluorophenyl)methyl]-N-[(3S)-7-ethyl-1-methyl-2,8-dioxo-4,5-dihydro-3H-pyrido[4,3-b]azepin-3-yl]-1,2,4-triazole-3-carboxamide; or a pharmaceutically acceptable salt thereof.

22. The compound of claim 1, or a pharmaceutically acceptable salt thereof, wherein $R^3$ is selected from the group consisting of $C_1$-$C_6$ alkyl, $C_1$-$C_6$ haloalkyl, $C_1$-$C_6$ alkoxy, $C_3$-$C_6$ cycloalkyl, —C($R^4$)$_2$—$C_3$-$C_6$ cycloalkyl, 4 to 6 membered heterocyclyl, and —C($R^4$)$_2$-(4 to 6 membered heterocyclyl).

23. A pharmaceutical composition comprising a compound of claim 13, or a pharmaceutically acceptable salt thereof, and a therapeutically inert carrier.

* * * * *